United States Patent
Ramanan et al.

(10) Patent No.: US 10,893,998 B2
(45) Date of Patent: Jan. 19, 2021

(54) COMPRESSION APPARATUS AND SYSTEMS FOR CIRCULATORY DISORDERS

(71) Applicants: ResMed Pty Ltd, Bella Vista (AU); ResMed Corp.; Virtuo Design Limited, Levin (NZ)

(72) Inventors: Dinesh Ramanan, Sydney (AU); Jose Ricardo Dos Santos, San Diego, CA (US); Blythe Guy Rees-Jones, Papamoa (NZ); Tzu-Chin Yu, Sydney (AU); Matthew John Backler, Tauranga (NZ)

(73) Assignee: INOVA LABS INC., San Diego, CA (US)

( * ) Notice: Subject to any disclaimer, the term of this patent is extended or adjusted under 35 U.S.C. 154(b) by 0 days.

(21) Appl. No.: 16/428,512

(22) Filed: May 31, 2019

(65) Prior Publication Data
US 2020/0113773 A1    Apr. 16, 2020

Related U.S. Application Data

(60) Provisional application No. 62/743,862, filed on Oct. 10, 2018, provisional application No. 62/830,189, filed on Apr. 5, 2019.

(51) Int. Cl.
*A61H 9/00* (2006.01)
*A61F 13/08* (2006.01)

(52) U.S. Cl.
CPC .......... *A61H 9/0092* (2013.01); *A61F 13/08* (2013.01); *A61H 2201/0103* (2013.01);
(Continued)

(58) Field of Classification Search
CPC ........ A61H 9/00; A61H 9/0078; A61H 9/005; A61H 9/0092
See application file for complete search history.

(56) References Cited

U.S. PATENT DOCUMENTS 3,186,405 A * 6/1965 Bailey ................ A61F 5/05816
                                                              602/13
3,811,431 A   5/1974 Apstein
(Continued)

FOREIGN PATENT DOCUMENTS

DE   19846922 A1   4/2000
FR   2682279 A1    4/1993
(Continued)

OTHER PUBLICATIONS

Motorola; "Integrated silicone Pressure Sensor On/Chip Signal Conditioned, Temperature Compensated and Calibrated"; MPX5050, MPXV5050G Series; 2002 (2 pages).
(Continued)

*Primary Examiner* — Justine R Yu
*Assistant Examiner* — Christopher E Miller
(74) *Attorney, Agent, or Firm* — Nixon Peabody LLP

(57) ABSTRACT

A garment for providing circulatory system disorder therapy includes a skin contacting layer, a backing layer, and a coupling. The backing layer is coupled to the skin contacting layer such that the skin contacting layer and the backing layer form a plurality of macro-chambers. A first one of the plurality of macro-chambers is partitioned into a plurality of micro-chambers. Each of the plurality of micro-chambers is in direct fluid communication with at least one other of the plurality of micro-chambers. The coupling is coupled to the backing layer and is configured to supply pressurized air directly into the first macro-chamber such that the pressurized air is delivered to a first one of the plurality of micro-chambers of the first macro-chamber.

25 Claims, 43 Drawing Sheets

(52) U.S. Cl.
CPC ........... *A61H 2201/1238* (2013.01); *A61H 2201/1409* (2013.01); *A61H 2201/165* (2013.01); *A61H 2201/1647* (2013.01); *A61H 2201/1695* (2013.01); *A61H 2201/5012* (2013.01); *A61H 2209/00* (2013.01)

(56) References Cited

U.S. PATENT DOCUMENTS

| | | | |
|---|---|---|---|
| 3,862,629 A * | 1/1975 | Rotta | A61H 9/0078 601/150 |
| 4,011,860 A | 3/1977 | Lee | |
| 4,011,866 A | 3/1977 | Klein | |
| 4,013,069 A | 3/1977 | Hasty | |
| 4,029,087 A * | 6/1977 | Dye | A61B 17/135 601/152 |
| 4,030,488 A * | 6/1977 | Hasty | A61H 9/0078 601/152 |
| 4,086,920 A | 5/1978 | Miniere | |
| 4,320,746 A * | 3/1982 | Arkans | A61H 9/0078 601/152 |
| 4,338,923 A | 7/1982 | Gelfer | |
| 4,424,806 A | 1/1984 | Newman | |
| 4,762,121 A | 8/1988 | Shienfeld | |
| 4,773,397 A | 9/1988 | Wright | |
| 4,865,020 A | 9/1989 | Bullard | |
| 4,922,893 A | 5/1990 | Wright | |
| 5,014,681 A | 5/1991 | Neeman | |
| 5,092,317 A | 3/1992 | Zelikovski | |
| 5,117,812 A | 6/1992 | McWhorter | |
| 5,156,629 A * | 10/1992 | Shane | A61F 2/7843 128/DIG. 20 |
| 5,179,941 A | 1/1993 | Siemssen | |
| 5,186,163 A | 2/1993 | Dye | |
| 5,263,473 A | 11/1993 | McWhorter | |
| 5,307,791 A | 5/1994 | Senoue | |
| 5,383,842 A | 1/1995 | Bertini | |
| 5,437,610 A | 8/1995 | Cariapa | |
| 5,496,262 A | 3/1996 | Johnson, Jr. | |
| 5,554,103 A | 9/1996 | Zheng | |
| 5,571,075 A | 11/1996 | Bullard | |
| 5,575,762 A | 11/1996 | Peeler | |
| 5,584,798 A | 12/1996 | Fox | |
| 5,588,955 A | 12/1996 | Johnson, Jr. | |
| 5,591,200 A | 1/1997 | Cone | |
| 5,795,312 A | 8/1998 | Dye | |
| 5,830,164 A | 11/1998 | Cone | |
| 5,840,049 A | 11/1998 | Tumey | |
| 5,843,007 A | 12/1998 | McEwen | |
| 5,891,065 A | 4/1999 | Cariapa | |
| 5,916,183 A * | 6/1999 | Reid | A61F 5/05858 601/134 |
| 5,951,502 A | 9/1999 | Peeler | |
| 5,968,073 A | 10/1999 | Jacobs | |
| 6,007,559 A | 12/1999 | Arkans | |
| 6,010,471 A | 1/2000 | Ben-Noon | |
| 6,080,120 A | 6/2000 | Sandman | |
| 6,123,681 A | 9/2000 | Brown, III | |
| 6,129,688 A | 10/2000 | Arkans | |
| 6,135,116 A | 10/2000 | Vogel | |
| 6,179,796 B1 | 1/2001 | Waldridge | |
| 6,231,532 B1 | 5/2001 | Watson | |
| 6,234,532 B1 | 5/2001 | Watson | |
| 6,290,662 B1 | 9/2001 | Morris | |
| 6,296,617 B1 | 10/2001 | Peeler | |
| 6,315,745 B1 | 11/2001 | Kloecker | |
| 6,406,445 B1 | 6/2002 | Ben-Nun | |
| 6,409,691 B1 * | 6/2002 | Dakin | A61F 5/012 128/DIG. 20 |
| 6,436,064 B1 | 8/2002 | Kloecker | |
| 6,440,093 B1 | 8/2002 | McEwen | |
| 6,494,852 B1 | 12/2002 | Barak | |
| 6,544,202 B2 | 4/2003 | McEwen | |
| 6,558,338 B1 | 5/2003 | Wasserman | |
| 6,585,669 B2 | 7/2003 | Manor | |
| 6,645,165 B2 | 11/2003 | Waldridge | |
| 6,656,141 B1 * | 12/2003 | Reid | A61B 17/1325 601/134 |
| 6,736,787 B1 | 5/2004 | McEwen | |
| 6,786,879 B1 | 9/2004 | Bolam | |
| 6,846,295 B1 | 1/2005 | Ben-Nun | |
| 6,852,089 B2 | 2/2005 | Kloecker | |
| 6,860,862 B2 | 3/2005 | Waldridge | |
| 6,884,255 B1 | 4/2005 | Newton | |
| 6,893,409 B1 | 5/2005 | Lina | |
| 6,945,944 B2 | 9/2005 | Kuiper | |
| 6,966,884 B2 | 11/2005 | Waldridge | |
| 7,048,702 B2 | 5/2006 | Hui | |
| 7,074,200 B1 | 7/2006 | Lewis | |
| 7,063,676 B2 | 8/2006 | Barak | |
| 7,398,803 B2 | 7/2008 | Newton | |
| 7,591,796 B1 * | 9/2009 | Barak | A61H 9/0078 601/152 |
| 7,637,879 B2 | 12/2009 | Barak | |
| 7,846,114 B2 | 12/2010 | Webster | |
| 7,862,525 B2 | 1/2011 | Carkner | |
| 8,052,630 B2 | 11/2011 | Kloecker | |
| 9,756,881 B2 * | 9/2017 | Grandin De L'eprevier | A41D 1/06 |
| 9,904,358 B2 * | 2/2018 | Rubin | B25J 11/003 |
| 2002/0091345 A1 | 7/2002 | Hazard | |
| 2003/0181990 A1 * | 9/2003 | Phillips | A61F 2/7843 623/37 |
| 2003/0208465 A1 | 11/2003 | Yurko | |
| 2004/0054306 A1 * | 3/2004 | Roth | A61H 9/0078 601/152 |
| 2004/0059274 A1 | 3/2004 | Kloecker | |
| 2004/0171971 A1 | 9/2004 | Ravikumar | |
| 2004/0261182 A1 | 12/2004 | Biggie | |
| 2005/0070405 A1 * | 3/2005 | Egger | A61H 9/005 482/78 |
| 2005/0070828 A1 * | 3/2005 | Hampson | A61H 9/0092 601/152 |
| 2005/0154336 A1 | 7/2005 | Kloecker | |
| 2005/0159690 A1 | 7/2005 | Barak | |
| 2005/0222526 A1 | 10/2005 | Perry | |
| 2006/0161081 A1 | 7/2006 | Barak | |
| 2006/0272719 A1 | 12/2006 | Steinberg | |
| 2007/0049853 A1 | 3/2007 | Adams | |
| 2007/0088239 A1 | 4/2007 | Roth | |
| 2007/0161933 A1 * | 7/2007 | Ravikumar | A61G 7/0755 602/13 |
| 2007/0272250 A1 | 11/2007 | Lewis | |
| 2008/0103397 A1 * | 5/2008 | Barak | A61H 9/0078 600/492 |
| 2008/0146980 A1 | 6/2008 | Rousso | |
| 2008/0281240 A1 | 11/2008 | Wright | |
| 2009/0007341 A1 | 1/2009 | Roff | |
| 2009/0056020 A1 | 3/2009 | Caminade | |
| 2009/0145234 A1 | 6/2009 | Gasbarro | |
| 2009/0177222 A1 * | 7/2009 | Brown | A61F 5/0104 606/202 |
| 2010/0137764 A1 * | 6/2010 | Eddy | A61H 1/008 601/152 |
| 2010/0249680 A1 | 9/2010 | Davis | |
| 2011/0034840 A1 * | 2/2011 | Broun (Wells) | A61H 9/0071 601/152 |
| 2012/0065561 A1 | 3/2012 | Ballas | |
| 2012/0078146 A1 | 3/2012 | Deshpande | |
| 2012/0089063 A1 * | 4/2012 | Olson | A61H 9/0078 601/152 |
| 2012/0219432 A1 | 8/2012 | Wright | |
| 2012/0277636 A1 | 11/2012 | Blondheim | |
| 2013/0125613 A1 | 5/2013 | Grotov | |
| 2013/0237889 A1 | 9/2013 | Wright | |
| 2013/0245519 A1 * | 9/2013 | Edelman | A61H 9/0092 601/152 |
| 2013/0310719 A1 * | 11/2013 | Davis | A61H 9/0085 601/149 |
| 2014/0052028 A1 | 2/2014 | Wright | |
| 2014/0303533 A1 * | 10/2014 | Zeutzius | A61H 9/0092 601/151 |

(56) References Cited

U.S. PATENT DOCUMENTS

| | | | |
|---|---|---|---|
| 2015/0080775 A1* | 3/2015 | Papadopoulos | A61H 9/0092 |
| | | | 601/151 |
| 2015/0150746 A1 | 6/2015 | Yurko | |
| 2015/0202116 A1 | 7/2015 | Wright | |
| 2015/0224012 A1 | 8/2015 | Wright | |
| 2016/0058653 A1* | 3/2016 | Oberdier | A61H 9/0078 |
| | | | 601/41 |
| 2017/0224577 A1* | 8/2017 | Cartier | A61H 9/0078 |
| 2018/0008507 A1* | 1/2018 | Saren | A61H 9/0078 |
| 2019/0125619 A1* | 5/2019 | Zeutzius | A61H 9/0092 |

FOREIGN PATENT DOCUMENTS

| | | | |
|---|---|---|---|
| GB | 2313784 A | 10/1997 | |
| WO | WO 2005/082314 A1 | 9/2005 | |
| WO | WO 2007/074451 A2 | 7/2007 | |
| WO | WO 2009/076269 A2 | 6/2009 | |
| WO | WO 2013/138307 A1 | 9/2013 | |
| WO | WO 2014/031409 A1 | 2/2014 | |
| WO | WO 2015/084312 A1 | 6/2015 | |

OTHER PUBLICATIONS

Extended European Search Report for EP 13760396, dated Sep. 30, 2015 (8 pages).

International Search Report and Written Opinion in International Patent Application No. PCT/US2019/055474, dated Mar. 20, 2020 (23 pages).

International Preliminary Report on Patentability in International Patent Application No. PCT/US2019/055474, dated Oct. 30, 2020 (51 pages).

\* cited by examiner

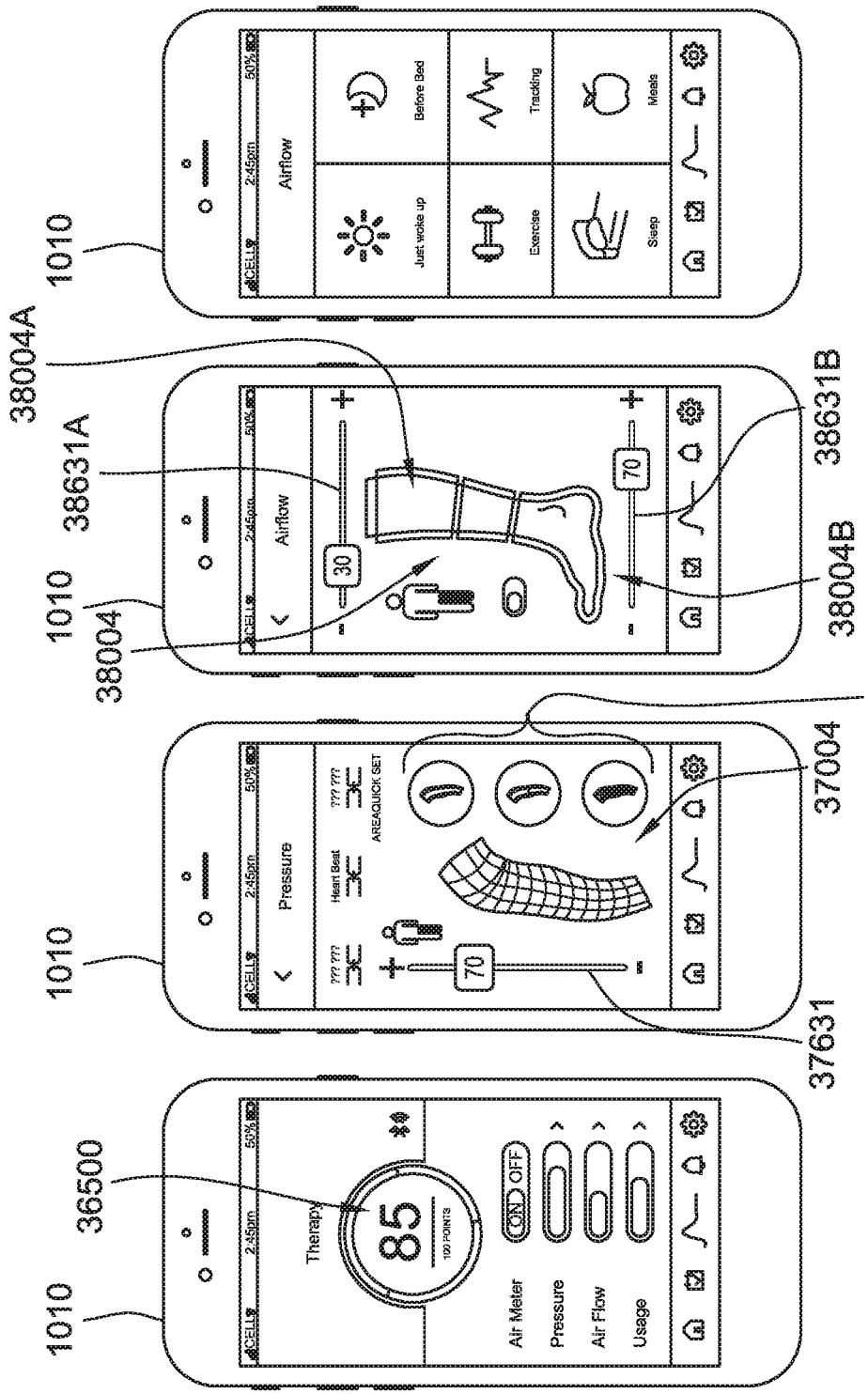

COMPRESSION APPARATUS AND SYSTEMS FOR CIRCULATORY DISORDERS

1. CROSS-REFERENCE TO RELATED APPLICATIONS

This application claims the benefit of and priority to U.S. Provisional Application No. 62/743,862, filed Oct. 10, 2018, and U.S. Provisional Application No. 62/830,189, filed Apr. 5, 2019, each of which is hereby incorporated by reference herein in its entirety.

2. FIELD OF THE PRESENT DISCLOSURE

The present technology relates to devices for the diagnosis, treatment and/or amelioration of circulatory related disorders, such as a disorder of the lymphatic system. In particular, the present technology relates to medical devices, and their components, such as for Lymphedema therapy or monitoring. Such technology may relate to components, for example, control apparatus, systems, and devices, for compression therapy such as for monitoring and/or treating the condition of a circulatory disorder.

3. BACKGROUND

The lymphatic system is crucial to keeping a body healthy. The system circulates lymph fluid throughout the body. This circulation collects bacteria, viruses, and waste products. The lymphatic system carries this fluid and the collected undesirable substances through the lymph vessels, to the lymph nodes. These wastes are then filtered out by lymphocytes existing in the lymph nodes. The filtered waste is then excreted from the body.

Lymphedema concerns swelling that may occur in the extremities, in particular, any of the arms, legs, feet, etc. The swelling of one or more limbs can result in significant physical and psychological morbidity. Lymphedema is typically caused by damage to, or removal of, lymph nodes such as in relation to a cancer therapy. The condition may result from a blockage in the lymphatic system, a part of the immune system. The blockage prevents lymph fluid from draining. Lymph fluid build-up leads to the swelling of the related extremity.

Thus, Lymphedema occurs when lymph vessels are unable to adequately drain lymph fluid, typically from an arm or leg. Lymphedema can be characterized as either primary or secondary. When it occurs independently from other conditions it is considered primary Lymphedema. Primary Lymphedema is thought to result from congenital malformation. When it is caused by another disease or condition, it is considered secondary Lymphedema. Secondary Lymphedema is more common than primary Lymphedema and typically results from damage to lymphatic vessels and/or lymph nodes.

Lymphedema is a chronic and incurable disease. If untreated, Lymphedema leads to serious and permanent consequences that are costly to treat. Many of the high-cost health consequences from Lymphedema might be prevented by early detection and access to appropriate remedial services. As there is no presently known cure for lymphedema, improvement in treating this and other circulatory related conditions, such as, for example, deep vein thrombosis, chronic venous insufficiency, and restless leg syndrome, is desired. The present disclosure is directed to solving these and other problems.

4. SUMMARY OF THE PRESENT DISCLOSURE

The present disclosure is directed towards providing medical devices, or the components thereof, for use in the management, monitoring, detection, diagnosis, amelioration, treatment, and/or prevention of circulatory related conditions having one or more of improved comfort, cost, efficacy, ease of use and manufacturability.

According to some implementations of the present disclosure, a smart, connected platform and/or system for compression therapy for treating circulatory disorders such as lymphedema, is provided. The system includes a compression garment with multiple pneumatic chambers, a valve interface, a pneumatic/electrical conduit, a compression device, a control device running a patient app, and a remote clinician portal. According to some implementations of the present disclosure, the chambers in the compression garment can be dynamically pressurised to compress a limb of interest (e.g., leg, arm, torso, foot, ankle, etc. or any combination thereof) in controlled therapeutic patterns over a therapy session. According to some implementations of the present disclosure, the chambers are high-resolution partitions and/or micro-chambers of a conventional chamber. According to some implementations of the present disclosure, the micro-chambers are interconnected by one or more channels that define one or more predetermined sequence(s) of air pressurization. When a chamber is pressurised, the micro-chambers of that chamber pressurise in the predetermined sequence(s) so as to create a micro-massage effect on the user wearing the compression garment of the system. The micro-massage can aid in stretching the skin of the user in a way that simulates natural movement of the limb and thereby assists drainage. According to some implementations of the present disclosure, sensors may be used (e.g., imbedded in the compression garment) to determine patient characteristics, such as limb girth, during a testing period and set up therapy mode and parameters before therapy (personalization or customization). According to some implementations of the present disclosure, sensors can be used in a control loop during therapy to dynamically adjust therapy parameters. According to some implementations of the present disclosure, therapy can be controlled and/or monitored using a patient application executing on a control device of the system. According to some implementations of the present disclosure, therapy data from multiple patients can be communicated to a clinician portal for population management.

According to some implementations of the present disclosure, a garment for providing circulatory system disorder therapy includes a skin contacting layer, a backing layer, and a coupling. The backing layer is coupled to the skin contacting layer such that the skin contacting layer and the backing layer form a plurality of macro-chambers. A first one of the plurality of macro-chambers is partitioned into a plurality of micro-chambers. Each of the plurality of micro-chambers is in direct fluid communication with at least one other of the plurality of micro-chambers. The coupling is coupled to the backing layer and is configured to supply pressurized air directly into the first macro-chamber such that the pressurized air is delivered to a first one of the plurality of micro-chambers of the first macro-chamber.

According to some implementations of the present disclosure, a compression garment for circulatory system disorder therapy includes a first layer, a second layer, and a pneumatic coupling. The first layer comprises an inner, skin contact layer. The second layer comprises an outer surface. The first and second layers form a garment wearable by a user. The first layer forms a plurality of interconnected micro-chambers. The pneumatic coupling is configured to directly or indirectly couple one of the plurality of interconnected micro-chambers with a pneumatic outlet of a compression pressure generation device so as to pressurise the plurality of interconnected micro-chambers in a predetermined sequence.

According to some implementations of the present disclosure, a garment for providing circulatory system disorder therapy includes a skin contacting layer, a backing layer, and a coupling. The skin contacting layer includes an elastic material such that the skin contacting layer is configured to deform under pressurization. The backing layer includes a rigid material such that the backing layer is configured to resist deformation under pressurization. The backing layer is coupled to the skin contacting layer such that the skin contacting layer and the backing layer form a plurality of micro-chambers. The coupling is coupled to the backing layer and is configured to supply pressurized air directly into a first one of the plurality of micro-chambers such that the pressurized air causes a portion of the skin contacting layer, corresponding to the first micro-chamber, to deform in a direction that is generally away from the backing layer.

The subject headings used in the detailed description are included only for the ease of reference of the reader and should not be used to limit the subject matter found throughout the disclosure or the claims. The subject headings should not be used in construing the scope of the claims or the claim limitations.

Various aspects of the described example embodiments may be combined with aspects of certain other example embodiments to realize yet further embodiments. It is to be understood that one or more features of any one example may be combinable with one or more features of the other examples. In addition, any single feature or combination of features in any example or examples may constitute patentable subject matter.

Other features of the technology will be apparent from consideration of the information contained in the following detailed description.

5. BRIEF DESCRIPTION OF THE DRAWINGS

The present technology is illustrated by way of example, and not by way of limitation, in the figures of the accompanying drawings, in which like reference numerals refer to similar elements including:

FIG. 36 is a plan view of a control device configured to graphically illustrate compression therapy scoring information, according to some implementations of the present disclosure.

FIG. 37 is a plan view of a control device configured to provide compression pressure slider controls, according to some implementations of the present disclosure.

FIG. 38 is a plan view of a control device configured to provide compression pressure slider controls for various zones of a compression garment, according to some implementations of the present disclosure.

FIG. 39 is a plan view of a control device configured to permit tagging of usage data, according to some implementations of the present disclosure.

6. DETAILED DESCRIPTION

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting. In particular, while the condition being monitored or treated is usually referred to below as Lymphedema, it is to be understood that the described technologies are also applicable to treatment and monitoring of other circulatory related disorders.

Figure 1:
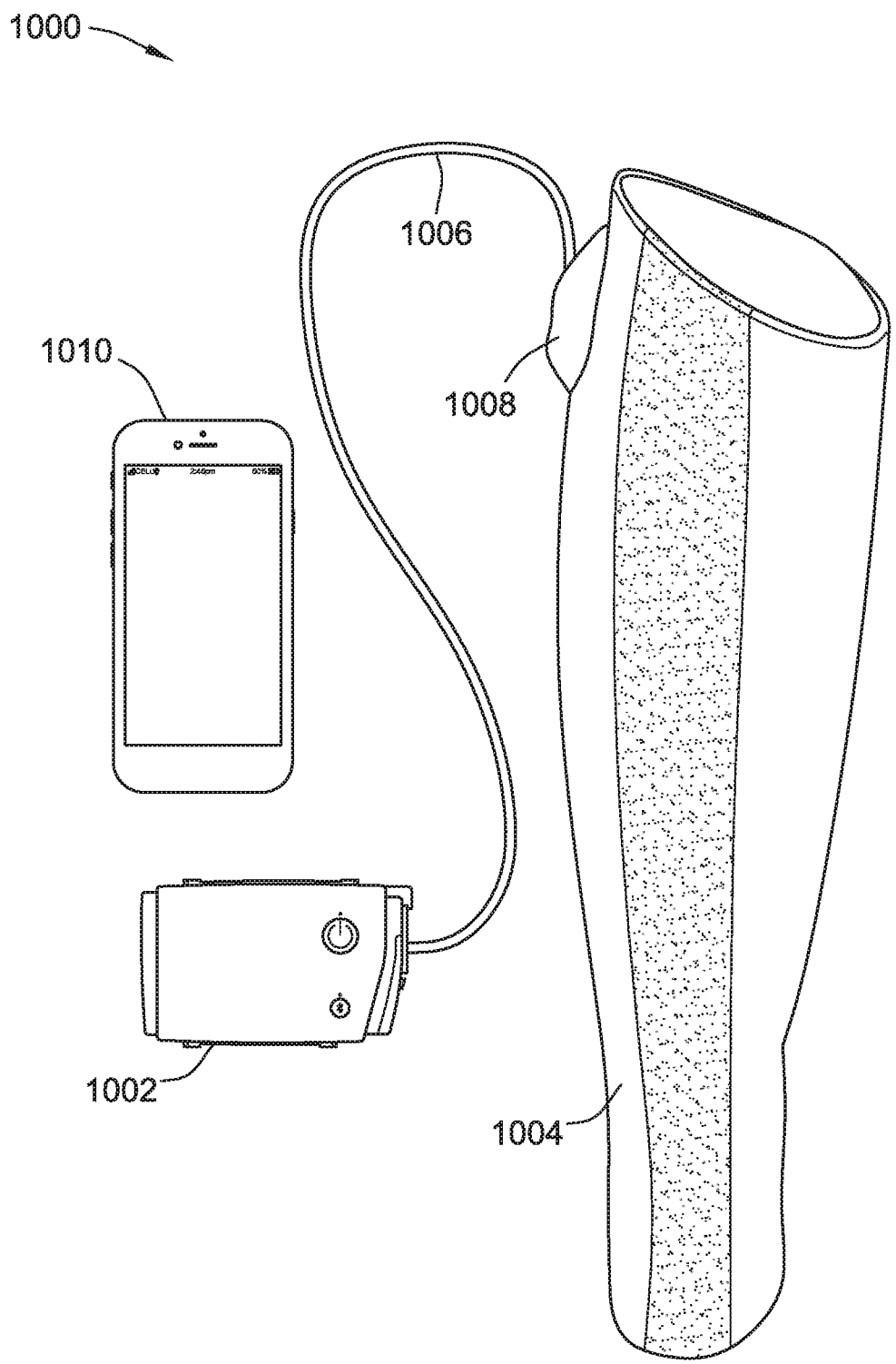
FIG. 1 is a perspective view of a compression therapy system for a compression therapy and/or circulatory system disorder monitoring including a compression pressure generator (CPG device) with a link to a compression garment and/or an optional control device, according to some implementations of the present disclosure.

Referring to FIG. 1, a compression therapy system 1000 for compression therapy and/or lymphedema monitoring is shown. The system 1000 includes a compression pressure generator (CPG) device 1002 and a compression garment 1004. A link 1006, such as to provide pneumatic and/or electrical coupling for control and/or operation of the compression garment 1004, connects the CPG device 1002 and the compression garment 1004. The link 1006 may connect with a conduit and/or valve interface 1008, such as one that is integrated with or separate from the compression garment 1004. The compression therapy system 1000 optionally includes a control device 1010, such as a mobile phone, tablet, laptop or other computing or computer device, executing an application to provide for setting the operational parameters (e.g., mode, type of therapy, pressure settings, valves, etc.) of the CPG device 1002 and/or monitoring operations and detected parameters of the CPG device 1002 and/or compression garment 1004.

Figure 2:
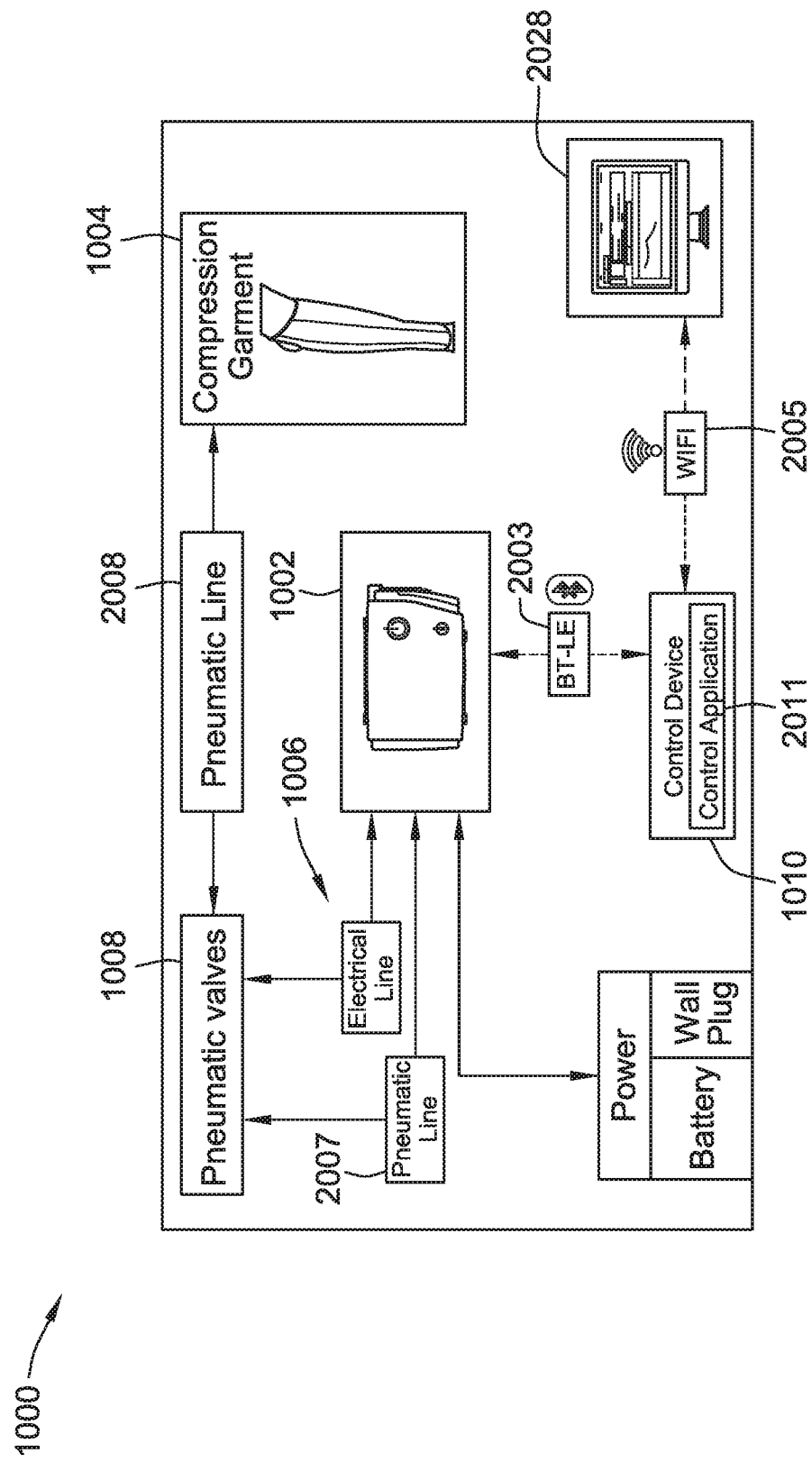
FIG. 2 is a block diagram of a compression therapy system including the components of the system of FIG. 1, according to some implementations of the present disclosure.

Referring to FIG. 2, various interactions of components of the system 1000 are shown. The system 1000 includes a portal system 2028, such as one with one or more servers, for managing a population of CPG devices. The CPG device 1002 conducts control device related communications 2003, such as wireless communications, with the control device 1010, running a control application 2011. Such communications may involve an exchange of data collected by the CPG device 1002, such as testing measurements and/or usage time, and sent to the control device 1010. Such communications may involve an exchange of control parameters for setting operations of the CPG device 1002, such as valve subset identifiers (zone) for controlling particular valves of the set of valves of the compression garment 1004, a pressure setting for the CPG device 1002, a therapy mode identifier, therapy times, a number of cycles etc. to the CPG device 1002. The wireless communications 2003 may employ a low energy wireless communications protocol such as Bluetooth LE or other.

As discussed in more detail herein, the application 2011 of the control device 1010 can be configured to provide limb, pressure, and usage feedback information to a user. The application 2011 can serve as a virtual coach such as by employing an artificial intelligence chat program. The application 2011 can serve as a social networking tool to other patients receiving similar care with a CPG device. The application 2011 can provide information to the user in relation to troubleshooting operations with the system 1000. The application 2011 can serve as a symptom tracker such as with input from the user and from the CPG device. The application 2011 can permit customization (personalization) with respect to the parameters controlling the therapy pressure waveform provided with the compression garment and the CPG device. The application 2011 can serve as an electronic store for ordering resupply components of the system (e.g., conduits, interfaces 1008, and compression garments). The application 2011 can provide informative/educational messages about disease condition (e.g., lymphedema). The application 2011 can provide user controls to start, stop and setup compression therapy sessions with the CPG device 1002 as well as run diagnostic procedures with the CPG device 1002 and compression garment 1004. The application 2011 can simplify use and setup workflow with the CPG device 1002.

The control device 1010 can be configured for portal related communications 2005, such as wireless communications (e.g., wireless protocol communications Wi-Fi), with the portal system 2028. The portal system 2028 can receive, from the control device 1010, testing measurements, therapy parameters, and/or usage time, and may communicate to the control device 1010, parameters for setting operations of the CPG device 1002, such as valve subset identifiers (zone) for controlling particular valves of the set of valves of the compression garment 1004, a pressure setting for the CPG device 1002, a therapy mode protocol, therapy times, a number of cycles, etc. Such a portal system 2028 can be managed by a clinician organization to provide actionable insights to patient condition for a population of CPG devices and their users.

For example, a clinician may provide prescriptive parameters for use of the CPG device 1002 (e.g., therapy control parameters) that may in turn be communicated to a control device 1010 and/or a CPG device 1002. Such communications, such as in relation to receiving testing measurements from the CPG device 1002 via the control device 1010, can permit therapy customization, such as by setting the prescriptive parameters based on the testing measurements. The portal system 2028 may similarly be implemented for compliance management in relation to received usage information from the CPG device 1002. The portal system 2028 may then serve as an integrated part of electronic medical records for a patient's lymphedema therapy.

The CPG device 1002 communicates with an interface 1008 via link 1006. The CPG device 1002 may generate electrical valve control signals on electric lines of a bus to the interface 1008 and receive electrical valve operation signals from the valves of the interface 1008 on the electric lines of the bus of the link 1006. The CPG device 1002 may also generate air flow such as a controlled pressure and/or flow of air to/from the interface 1008 via one or more pneumatic conduits 2007 of the link 1006. The interface 1008 may then selectively direct the pressure and/or flow to/from the chambers of the garment 1004 via any of the pneumatic lines 2008 between the interface 1008 and the compression garment 2004. Optionally, the valves of the interface 1008 and/or the pneumatic lines 2008 may be integrated (partially and/or fully) with the compression garment 1004.

6.1 CPG Device

Figure 3:
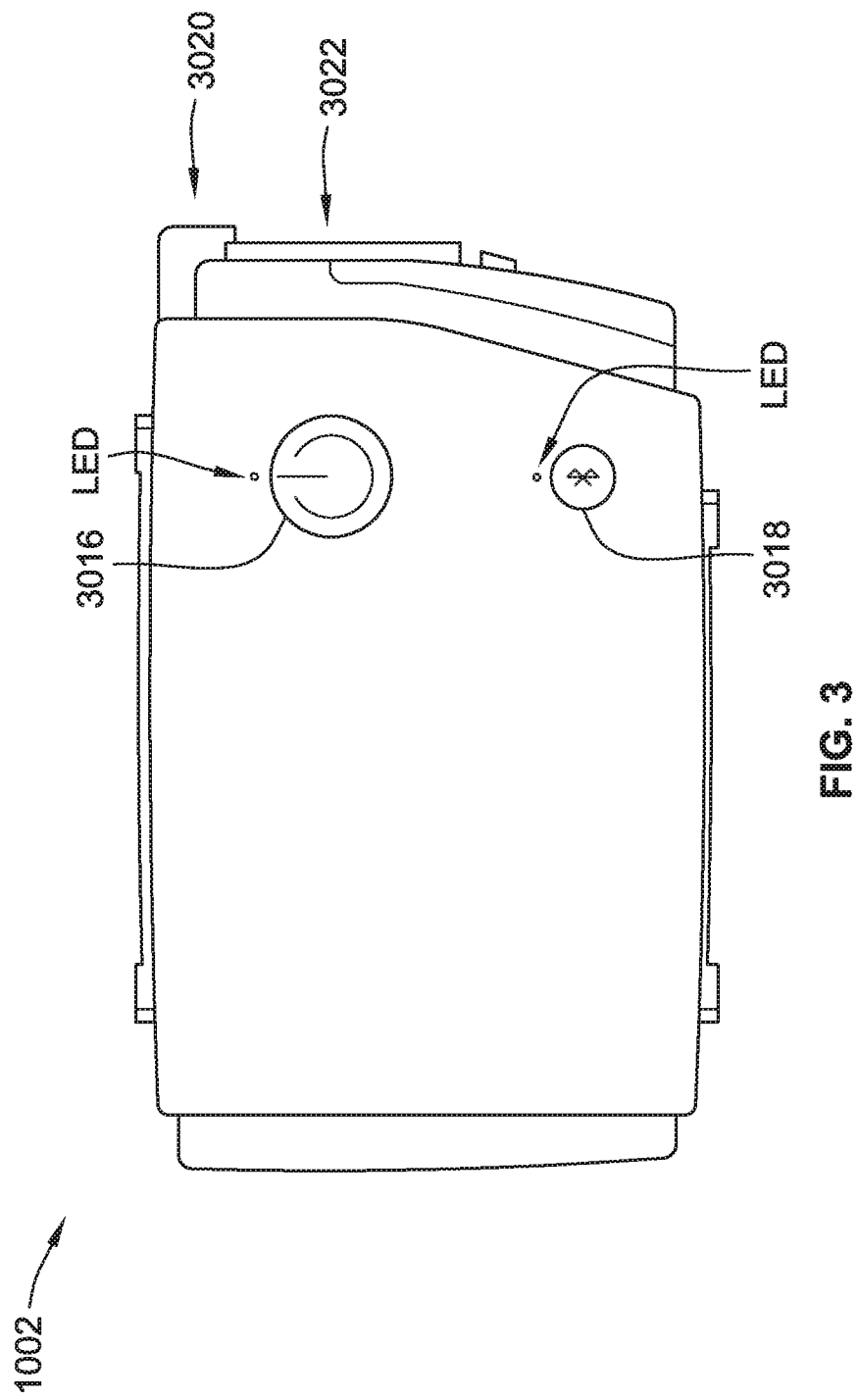
FIG. 3 is a front view of a compression pressure generator (CPG) device suitable for use in a compression therapy system, according to some implementations of the present disclosure.

The CPG device 1002 is illustrated in FIG. 3. The CPG device 1002 may have a compact and/or portable design to simplify use with a compression garment (e.g., compression garment 1004). The CPG device 1002 includes a start/stop button 3016. The CPG device 1002 also has a communications link button 3018 to aid in establishing a communications link (e.g., wireless communications) with the control device 1010 (FIG. 1). The CPG device 1002 also includes an electrical interface 3020 for electrically coupling with a valve control interface or valves of the garment 1004. The CPG device 1002 also includes a pneumatic interface 3022 (inlet/outlet) for pneumatic coupling with the compression garment 1004, such as via a set of valves.

As discussed in more detail herein, the CPG device 1002 may have a programmable controller to provide operations for compression therapies described herein and diagnostic operations. Such therapies may be provided by control of a blower of the CPG device 1002 that may produce positive pressure and/or negative pressure operations via one or more pneumatic conduits coupled to the compression garment 1004. For example, the CPG device 1002 may be configured to generate varied positive pressure for compression up to a maximum of about 50 mmHg into one or more chambers of the compression garment 1004. Similarly, the CPG device 1002 may produce negative pressure, such as to evacuate one or more pneumatic chamber of the compression garment 1004. Such a generation of positive and/or negative pressure (e.g., vacuum) may be controlled to provide compression therapy, including massage therapy, with the compression garment 1004 in relation to a set of pneumatic chambers within the compression garment 1004 that are pneumatically coupled to the blower of the CPG device 1002, such as via one or more valves and/or hoses that may be implemented with the interface 1008 (FIG. 2).

Figure 4:
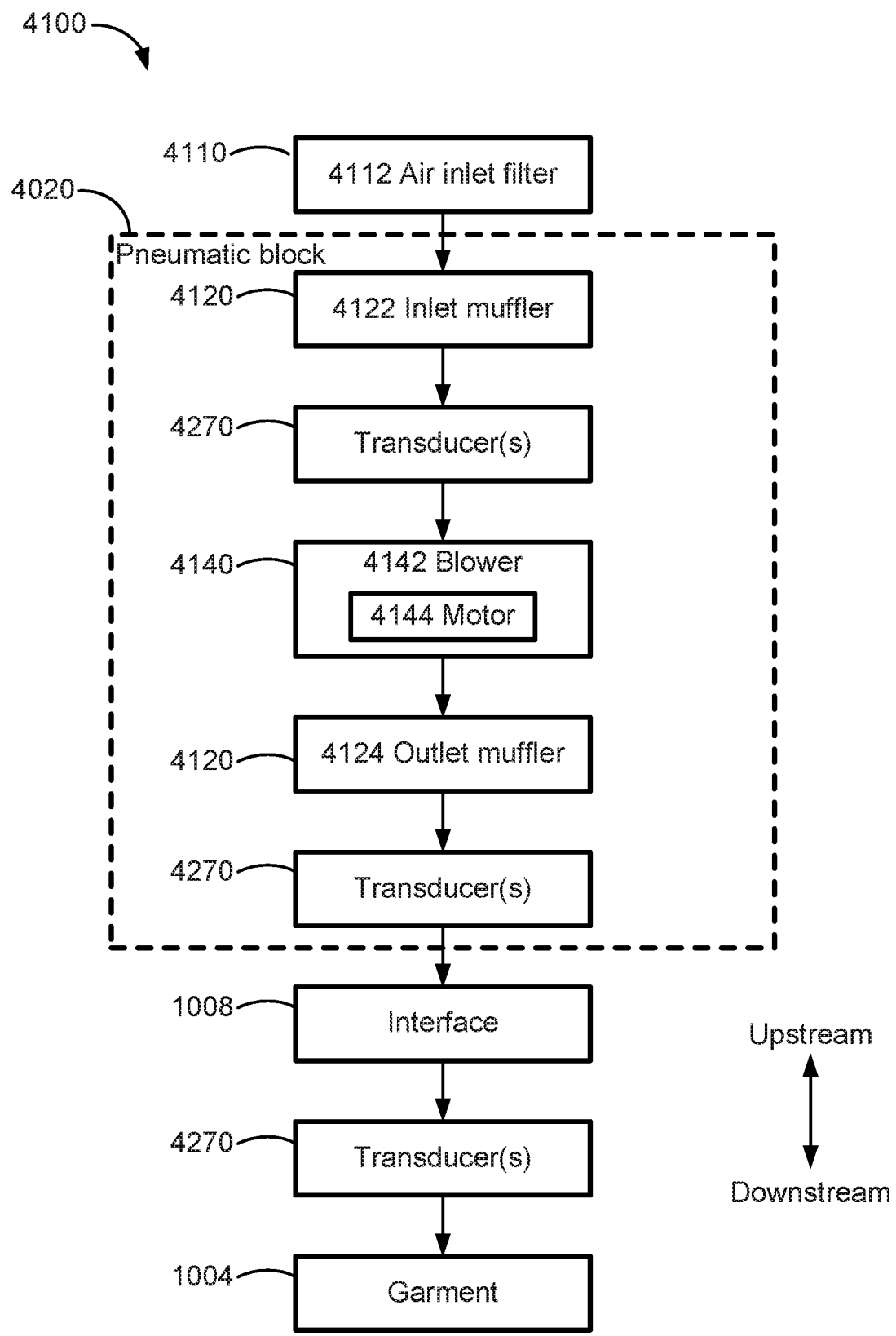
FIG. 4 is a flow chart of a pneumatic circuit of the CPG device of FIG. 3.
Figure 5:
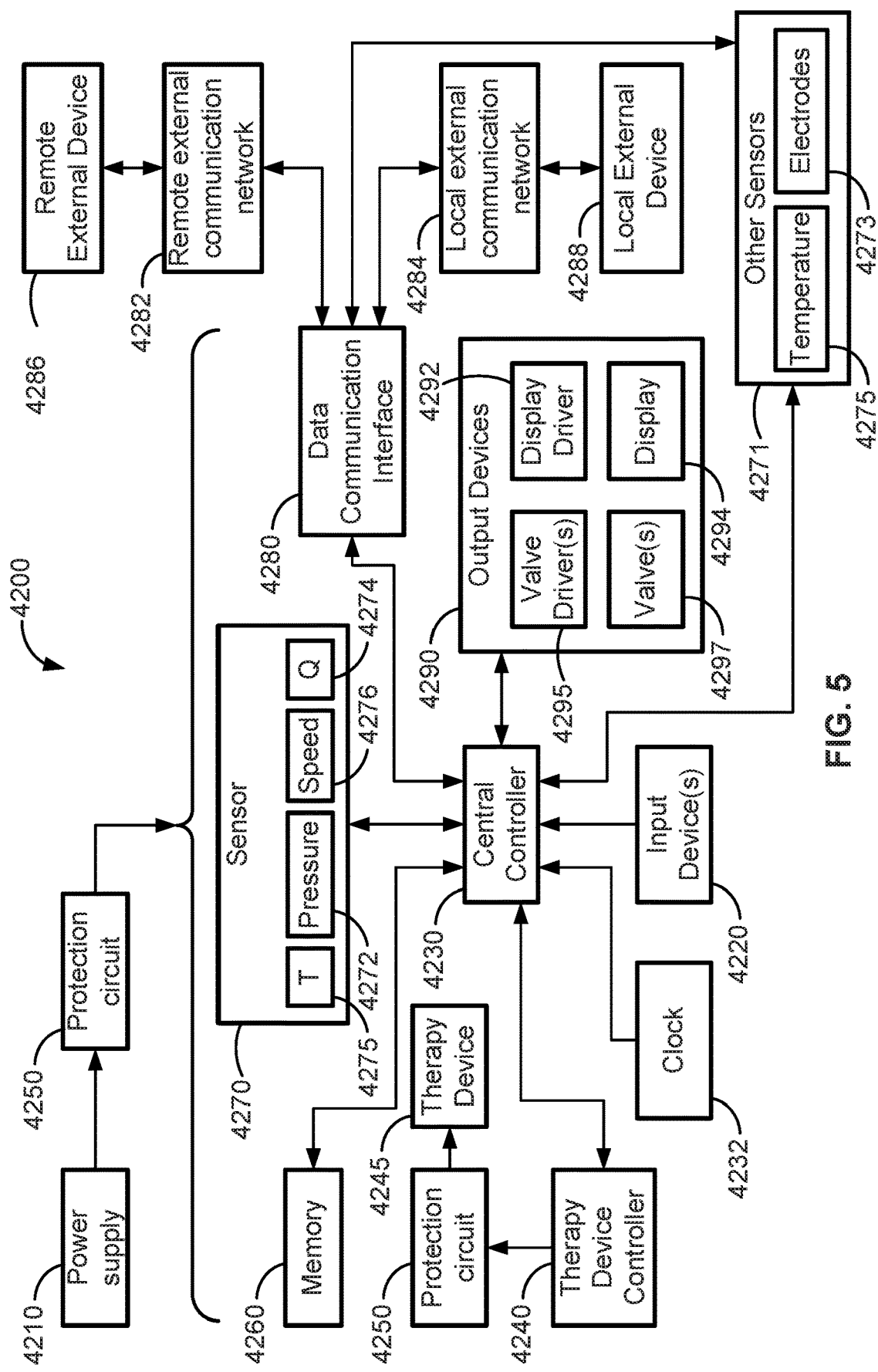
FIG. 5 is a schematic diagram of some electrical components of the CPG device of FIG. 3.

Referring to FIGS. 4 and 5, a compression pressure generator such as the CPG device 1002 may include mechanical and pneumatic components 4100 (FIG. 4), electrical components 4200 (FIG. 5) and may be programmed to execute one or more compression control algorithms. The CPG device 1002 has an external housing (see FIG. 3) that may be formed in two parts, an upper portion and a lower portion. In alternative forms, the external housing may include one or more panel(s). The CPG device 1002 may typically include a chassis that supports one or more internal components of the CPG device 1002. In one form a pneumatic block 4020 (FIG. 4) is supported by, or formed as part of the chassis. The CPG device 1002 may optionally include a handle.

Referring to FIG. 4, a pneumatic path of the CPG device 1002 may comprise any of an inlet air filter 4112, an inlet muffler 4122, a controllable flow or pressure device 4140 capable of supplying air at positive pressure (preferably a blower 4142) and/or vacuuming air at negative pressure such as by reversing operation of the blower, and an outlet muffler 4124. One or more pressure sensors and flow sensors, such as transducers 4270, may be included in the pneumatic path.

The pneumatic block 4020 may include a portion of the pneumatic path that is located within the external housing. The pneumatic path may then lead to an optional conduit or valve interface 1008, such as for controlled/selective directing of the pressurized air from the compression pressure generator to different pneumatic chambers of a compression garment 1004.

Referring to FIG. 5, electronic components 4200 of the CPG device 1002 may include an electrical power supply 4210, such as a battery power supply and/or AC main power supply converter (e.g., alternating current AC to direct current DC), one or more input devices 4220 (e.g., buttons), a central controller 4230, a therapy device controller 4240, a therapy device 4245 (e.g., blower with impeller and motor), one or more optional protection circuits 4250, memory 4260, transducers 4270, data communication interface 4280 and one or more output devices 4290 (e.g., lights, valve control). Electrical components 4200 may be mounted on a single Printed Circuit Board Assembly (PCBA). In an alternative form, the CPG device 1002 may include more than one PCBA.

The central controller 4230 of the CPG device 1002 is programmed to execute one or more compression mode control algorithms, and may include a detection module (e.g., sine wave generation control and evaluation).

6.1.1 CPG Device Mechanical & Pneumatic Components 6.1.1.1 Air Filter(s) 4110

Referring back to FIG. 4, the CPG device 1002 may include an air filter 4110, or a plurality of air filters 4110 (e.g., filter 4112). Such air filters may keep passages of the compression garment clean of air debris.

6.1.1.2 Muffler(s) 4120

The CPG device 1002 may include an inlet muffler 4122 that is located in the pneumatic path upstream of a blower 4142.

The CPG device 1002 may include an outlet muffler 4124 that is located in the pneumatic path between the blower 4142 and the compression garment 1004.

6.1.1.3 Pressure Device 4140

Referring to FIGS. 4 and 5, a flow or pressure device 4140 for producing a flow of air at positive pressure is a controllable blower 4142. For example, the blower 4142 may include a brushless DC electric motor 4144 with one or more impellers housed in a volute. The blower 4142 is capable of delivering a supply of air and/or drawing (vacuuming) a supply of air. The flow or pressure device 4140 is under the control of the therapy device controller 4240 (FIG. 5).

6.1.1.4 Transducer(s) 4270

With continued reference to FIGS. 4 and 5, the CG device 1002 may include one or more transducers 4270 (e.g., pressure, flow rate, temperature) that are located upstream of the pressure device 4140. The one or more transducers 4270 are constructed and arranged to measure properties of the air at that point in the pneumatic path.

Alternatively or additionally, one or more transducers 4270 are located downstream of the pressure device 4140, and upstream of the interface 1008. The one or more transducers 4270 are constructed and arranged to measure properties of the air at that point in the pneumatic path.

Alternatively of additionally, one or more transducers 4270 are located proximate to and/or within the compression garment 1004.

6.1.1.5 Air Conduit and/or Valve Interface 1008

As shown in FIGS. 1 and 4, an air conduit, such as via an optional conduit and valve interface 1008, in accordance with an aspect of the present technology is constructed and arranged to allow a flow of air between the pneumatic block 4020 and the compression garment 1004.

6.1.2 CPG Device Electrical Components 6.1.2.1 CPG Device 6.1.2.1.1 Power Supply 4210

Referring to FIG. 5, a power supply 4210 supplies power to the other components of the CPG device 1002, such as, the input device 4220, the central controller 4230, the therapy device 4245, and the output device 4290, valves, etc. Such a power supply may provide a DC voltage, such as 24 volts.

The power supply 4210 can be internal to the external housing of the CPG device 1002, such as in the case of a battery (e.g., a rechargeable battery). Alternatively, the power supply 4210 can be external of the external housing of the CPG device 1002. The internal or external power supply may optionally include a converter such as to provide a DC voltage converted from an AC supply (e.g., a main supply).

6.1.2.1.2 Input Device(s) 4220

Input devices 4220 (shown in FIG. 5) may include one or more of buttons, switches or dials to allow a person to interact with the CPG device 1002. The buttons, switches or dials may be physical devices, or software devices accessible via an optional touch screen of the CPG device 1002. The buttons, switches or dials may, in one form, be physically connected to the external housing, or may, in another form, be in wireless communication with a receiver that is in electrical connection to the central controller 4230.

The input device 4220 may be constructed and arranged to allow a person to select a value and/or a menu option. Alternatively, the input device 4220 may simply be configured to turn the CPG device 1002 on and/or off 6.1.2.1.3 Central Controller 4230

The central controller 4230 (shown in FIG. 5) is a dedicated electronic circuit configured to receive input signal(s) from the input device 4220, and to provide output signal(s) to the output device 4290 and/or the therapy device controller 4240 and/or a valve controller or valve interface.

The central controller 4230 can be an application-specific integrated circuit. Alternatively, the central controller 4230 can be formed with discrete electronic components.

The central controller 4230 can be a processor 4230 or a microprocessor, suitable to control the CPG device 1002 such as an x86 INTEL processor.

The central controller 4230 suitable to control the CPG device 1002 in accordance with another form of the present technology includes a processor based on ARM Cortex-M processor from ARM Holdings. For example, an STM32 series microcontroller from ST MICROELECTRONICS may be used.

In a further alternative form of the present technology, central controller 4230 may include a member selected from the family ARM9-based 32-bit RISC CPUs. For example, an STR9 series microcontroller from ST MICROELECTRONICS may be used.

In certain alternative forms of the present technology, a 16-bit RISC CPU may be used as the central controller 4230 for the CPG device 1002. For example, a processor from the MSP430 family of microcontrollers, manufactured by TEXAS INSTRUMENTS, may be used.

The central controller 4230 is configured to receive input signal(s) from one or more transducers 4270, and one or more input devices 4220. The central controller 4230 may also be configured with one or more digital and/or analog input/output ports as previously described such as for implementing the mode of operations and detection modules in conjunction with the operations of the system. For example, such input and/or output ports may provide control over or detect position of active pneumatic valves controlled by the central controller for directing compression related pressure to pneumatic chambers of the compression garment 1004.

Thus, the central controller 4230 is configured to provide output signal(s) to one or more of an output device 4290 (e.g., one or more valves of a set of valve(s)), a therapy device controller 4240, and a data communication interface 4280. Thus, the central controller 4230 may also be configured with one or more digital and/or analog output ports as previously described such as for implementing the mode of operations or detection module in conjunction with the operations of the CPG device 1002.

The central controller 4230, or multiple processors, is configured to implement the one or more methodologies described herein such as the one or more algorithms, as described in more detail herein, expressed as computer programs stored in a computer readable storage medium, such as memory 4260. In some cases, as previously discussed, such processor(s) may be integrated with the CPG device 1002. However, in some devices the processor(s) may be implemented discretely from the pressure generation components of the CPG device 1002, such as for purpose of performing any of the methodologies described herein without directly controlling delivery of a compression therapy. For example, such a processor may perform any of the methodologies described herein for purposes of determining control settings for the compression garment 1004 or monitoring of a circulatory or lymphatic system disorder by analysis of stored data such as from any of the sensors described herein. Such a processor may also perform any of the methodologies relating to the different mode of operations as described in more detail herein.

6.1.2.1.4 Therapy Device 4245

In one form of the present technology, the therapy device 4245 (shown in FIG. 5) is configured to deliver compression therapy to a user wearing the compression garment 1004 under the control of the central controller 4230. The therapy device 4245 may be the controllable flow or pressure device 4140, such as a positive and/or negative air pressure device 4140. Such a device may be implemented with a blower, such as a servo-controlled blower. Such a blower may be implemented with a motor having an impeller in a volute.

6.1.2.1.5 Therapy Device Controller 4240

In one form of the present technology, therapy device controller 4240 (shown in FIG. 5) is a therapy control module that may implement features of the compression related algorithms executed by or in conjunction with the central controller 4230. In some cases, the therapy device controller 4240 may be implemented with a motor drive. It may also optionally be implemented with a valve controller. Thus, such algorithms may generate motor control signals to operate a motor of blower to control generation of compression related pressure/flow. Such algorithms may also generate valve control signals to control operation of a set of valves for directing location of such compression related pressure/flow via one or more valves of the set of valves coupled with pneumatic chambers of the compression garment 1004.

In one form of the present technology, therapy device controller 4240 includes a dedicated motor control integrated circuit. For example, in one form a MC33035 brushless DC motor controller, manufactured by ONSEMI is used.

6.1.2.1.6 Protection Circuits 4250

The CPG device 1002 in accordance with the present technology optionally includes one or more protection circuits 4250 such as shown in FIG. 5.

One form of protection circuit 4250 in accordance with the present technology is an electrical protection circuit. Another form of protection circuit 4250 in accordance with the present technology is a temperature or pressure safety circuit.

In some versions of the present technology, a protection circuit 4250 may include a transient absorption diode circuit configured to absorb energy generated or converted from rotational kinetic energy, such as from the blower motor, which may be applied to charging a battery of the CPG device. According to another aspect of the present technology, a protection circuit 4250 may include a fault mitigation integrated circuit.

6.1.2.1.7 Memory 4260

In accordance with one form of the present technology the CPG device 1002 includes memory 4260 (shown in FIG. 5), preferably non-volatile memory. The memory 4260 may include battery powered static RAM memory, volatile RAM memory, EEPROM memory, NAND flash memory, or any combination thereof. The memory 4260 can be located on a PCBA (not shown).

Additionally or alternatively, the CPG device 1002 can include a removable form of memory 4260, for example, a memory card made in accordance with the Secure Digital (SD) standard.

The memory 4260 can act as a computer readable storage medium on which is stored computer program instructions expressing the one or more methodologies described herein, such as the one or more algorithms discussed herein.

6.1.2.1.8 Transducers 4270

Transducers 4270 (schematically shown in FIGS. 4 and 5) may be internal to the CPG device 1002, or external to the CPG device 1002. External transducers may be located on or form part of, for example, the CPG device 1002, the conduit or valve interface 1008, and/or the compression garment 1004.

6.1.2.1.8.1 Flow

A flow transducer 4274 (shown in FIG. 5) in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element.

In use, a signal representing a total flow rate Q from the flow transducer 4274 is received by the central controller 4230. However, other sensors for producing such a flow rate signal or estimating flow rate may be implemented. For example, a mass flow sensor, such as a hot wire mass flow sensor, may be implemented to generate a flow rate signal in some embodiments. Optionally, flow rate may be estimated from one or more signals of other sensors described herein (e.g., speed and pressure sensor).

6.1.2.1.8.2 Pressure

A pressure transducer 4272 (shown in FIG. 5) in accordance with the present technology is located in fluid communication with the pneumatic circuit. An example of a suitable pressure transducer is a sensor from the HONEYWELL ASDX series. An alternative suitable pressure transducer is a sensor from the NPA Series from GENERAL ELECTRIC.

In use, a signal from the pressure transducer 4272 is received by the central controller 4230. In one form, the signal from the pressure transducer 4272 is filtered prior to being received by the central controller 4230.

6.1.2.1.8.3 Motor Speed

In one form of the present technology a motor speed signal from a motor speed transducer 4276 (shown in FIG. 5) is generated. A motor speed signal is preferably provided by therapy device controller 4240. Motor speed may, for example, be generated by a speed sensor, such as a Hall Effect sensor.

6.1.2.1.8.4 Temperature

The temperature transducer(s) 4275 (shown in FIG. 5) may measure temperature of the gas in the pneumatic circuit and/or in the compression garment 1004. One example of the temperature transducer 4275 is a thermocouple or a resistance temperature detector (RTD).

6.1.2.1.9 Other Sensors

With continued reference to FIG. 5, in one form of the present technology, additional sensors 4271 may be coupled (e.g., wirelessly or wired) to the CPG device 1002 (e.g., via link 1006 or data communications interface) such as for detection of bio-related conditions within the compression garment. For example, as discussed in more detail herein, one or more sets of electrodes 4273 may be contained within the compression garment and provide measurements to the CPG device 1002 (e.g., central controller 4230). Such electrodes may be implemented to measure biopotential from the skin or skin impedance of the user in one or more zones of the compression garment 1004. Such electrode-based measurements may be evaluated, such as by the central controller 4230 or control device or other portal system, to determine body composition as an indication of condition of Lymphedema. Similarly, as previously mentioned, one or more temperature sensors 4275 may be located in zones of the compression garment 1004 to measure a temperature associated with the zone to provide an indication of a skin temperature of the user in the particular zone. Such measurements may be provided, such as via a bus to the central controller 4230 such as for creating a log of measurements and/or providing an adjustment to a compression protocol based on the measurements such as for the particular zone. The central controller 4230 or control device may also generate warnings (e.g., communications) to report a temperature, such as one exceeding a threshold, to inform a user or clinician (e.g., via a portal system) of a need for treatment (e.g., antibiotic for an infection). As discussed in more detail herein, in some versions, tension or strain gauge sensor(s) may also be implemented for detection of compression strain within the compression garment 1004, such as for detecting limb girth or volume.

6.1.2.1.10 Data Communication Systems

A data communication interface 4280 (shown in FIG. 5) can be provided and connected to the central controller 4230. The data communication interface 4280 may be connectable to remote external communication network 4282. The data communication interface 4280 can be connectable to a local external communication network 4284. The remote external communication network 4282 is connectable to a remote external device 4286, such as a population management server communicating with multiple CPG devices. The local external communication network 4284 is connectable to the local external device 4288, such as control device 1010. The data communications interface 4280 may optionally include a wireless communications interface (e.g., a transceiver using a wireless protocol such as Bluetooth, WIFI, Bluetooth LE etc.), such as for communications with the control device 1010, such as when it serves as the local external device 4288. Optionally, such a data communications interface 4280 may communicate, e.g., wirelessly, with one or more sensors of the compression garment 1004 and/or one or more active valves of, or coupled to, the compression garment 1004.

In one form, data communication interface 4280 is part of the central controller 4230. In another form, data communication interface 4280 is an integrated circuit that is separate from the central controller 4230.

In one form, the remote external communication network 4282 is a wide area network such as the Internet. The data communication interface 4280 may use wired communication (e.g. via Ethernet, or optical fibre) or a wireless protocol to connect to the Internet.

In one form, local external communication network 4284 utilises one or more communication standards, such as Bluetooth, or a consumer infrared protocol.

In one form, the remote external device 4286 is one or more computers, for example a cluster of networked computers. In one form, the remote external device 4286 may be virtual computers, rather than physical computers. In either case, such remote external device 4286 may be accessible to an appropriately authorised person such as a clinician.

The local external device 4288 can be a personal computer, mobile phone, tablet or remote control.

6.1.2.1.11 Output Devices Including Optional Display, Alarms, Active Valves

An output device 4290 (shown in FIG. 5) in accordance with an example of present technology may optionally take the form of one or more of a visual, audio, haptic unit(s) and/or a valve driver for a set of active valves such as the pneumatic valves of the interface 1008, which may be integrated with the CPG device 1002, the compression garment 1004 and/or a discrete device board serving as the interface 1008. Each of such active valves may be a pneumatic valve configured to receive a control signal to directionally gate and/or proportionally permit transfer of air selectively through the valve.

For example, as discussed in more detail herein, the output device 4290 may include one or more valve driver(s) 4295 for one or more active valves or one or more active valve(s) 4297. Such output devices 4290 may receive signals from the central controller 4230 for driving operation of the valves 4297. Such valve driver(s) 4295 or valves 4297 may be discrete from the CPG device 1002 external housing and coupled to the CPG device 1002 via a bus, such as a Controller Area Network (CAN) bus such as where the central controller 4230 includes a CAN bus controller. A suitable electrical coupler portion of link 1006 may serve to couple the bus with the valve driver 4295 and/or valves 4297. The active valves may be any suitable pneumatic valve for directing air flow, such as a gate valve, a multi-port valve, or a proportional valve, any of which may be operated by an included solenoid. In some implementations, the active valves 4297 and valve drivers 4295 may be within the CPG device 1002 housing or in a discrete housing of an interface (e.g., conduit and valve interface 1008) or in the compression garment 1004.

An optional visual display 4294 may be a Liquid Crystal Display (LCD) or Light Emitting Diode (LED) display. An optional display driver 4292 (shown in FIG. 5) may receive as an input the characters, symbols, or images intended for display on the display 4294, and converts them to commands that cause the display 4294 to display those characters, symbols, or images.

The display 4294 (shown in FIG. 5) may optionally be configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

6.1.2.2 Therapy Device 4245

In a preferred form of the present technology, the therapy device 4245 (FIG. 5) is under the control of the therapy device controller 4240 (e.g., a therapy control module) to generate therapy to the compression garment 1004 worn by a user (e.g., a patient). In some implementations, the therapy device 4245 is an air pressure device 4140 (FIG. 4), such as positive pressure device that can generate negative pressure.

6.2 Conduit and/or Valve Interface

Figure 6:
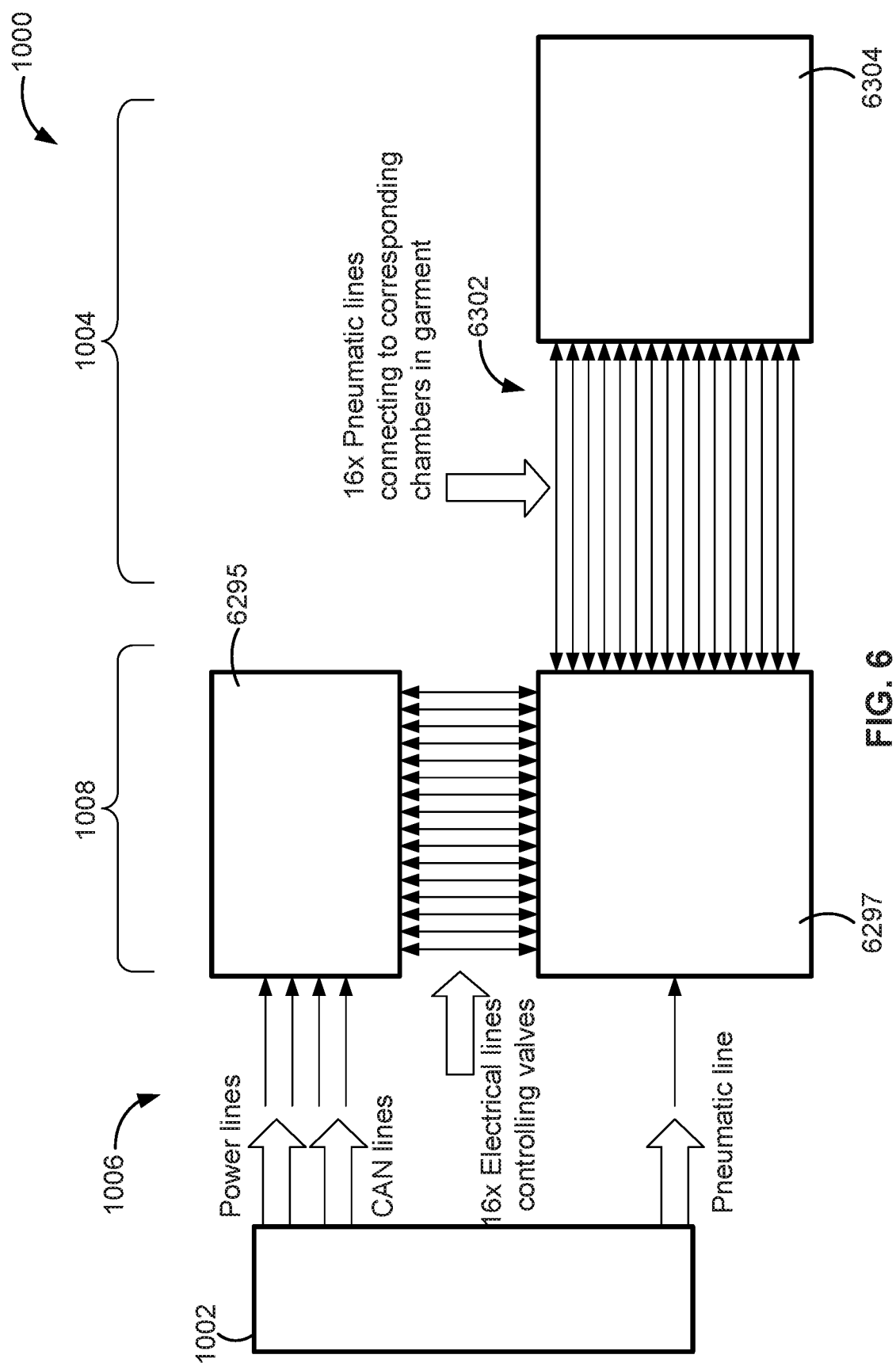
FIG. 6 is a schematic diagram of an interface for control valves for a compression garment, according to some implementations of the present disclosure.

Referring to FIG. 6, when implemented with active valves 6297, the conduit and/or valve interface 1008 may be implemented to control multiple valves for selective setting of the pneumatic condition of chambers of the compression garment 1004. The link 1006 between the CPG device 1002 and the compression garment 1004 includes a plurality of electrical lines, such as for providing power and signals from a CAN bus of the CPG device 1002. The link 1006 also provides a pneumatic line for fluid communication between the CPG device 1002 and the interface 1008. In this example, an active valve driver board 6295 is configured to communicate with the central controller 4230 (FIG. 5) via the CAN bus lines. Similarly, the active valve driver board 6295 has electrical lines permitting the active valve driver board 6295 to control (e.g., open, close or partially open) the pneumatic path of each of a set of active valves 6297. In this regard, the set of active valves 6297 may be configured with a manifold that fluidly couples one side of a pneumatic path of each valve with the pneumatic line of the link 1006. Similarly, each valve 6297 may be fluidly coupled to an additional pneumatic line. The additional pneumatic line may be integrated with, or lead to, a pneumatic path of the compression garment 1004 that may be uniquely associated with one or more pneumatic chamber(s) of the compression garment 1004. As shown in FIG. 6, sixteen valves provide sixteen pneumatic connecting lines 6302, which may be implemented by conduits or tubes, leading to the pneumatic chambers 6304 of the compression garment 1004.

The interface 1008 is shown as including sixteen active valves 6297; however, such an interface may have fewer or more of such active valves 6297 depending on the desired configuration of a compression garment and the type and number of chambers in the compression garment to be pressurized by the CPG device 1002.

Figure 7:
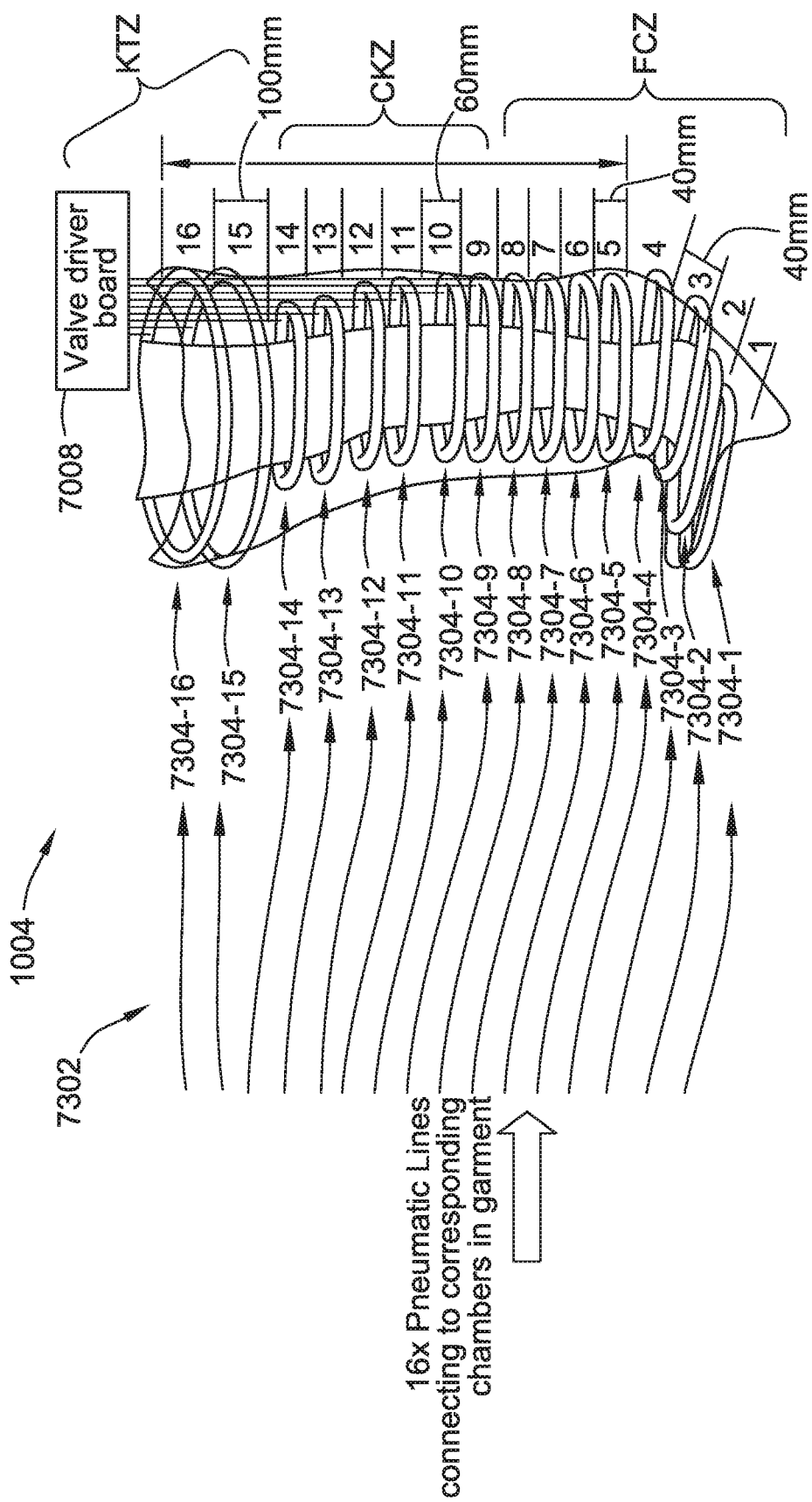
FIG. 7 illustrates a compression garment with a set of controllable compression chambers and pneumatic lines, according to some implementations of the present disclosure.
Figure 8A:
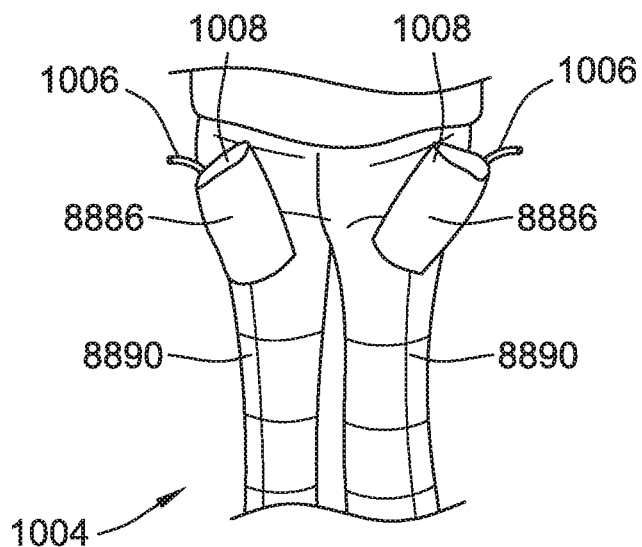
FIG. 8A is a perspective view of a compression garment with pockets holding valve interfaces for controllable compression chambers, according to some implementations of the present disclosure.
Figure 8B:
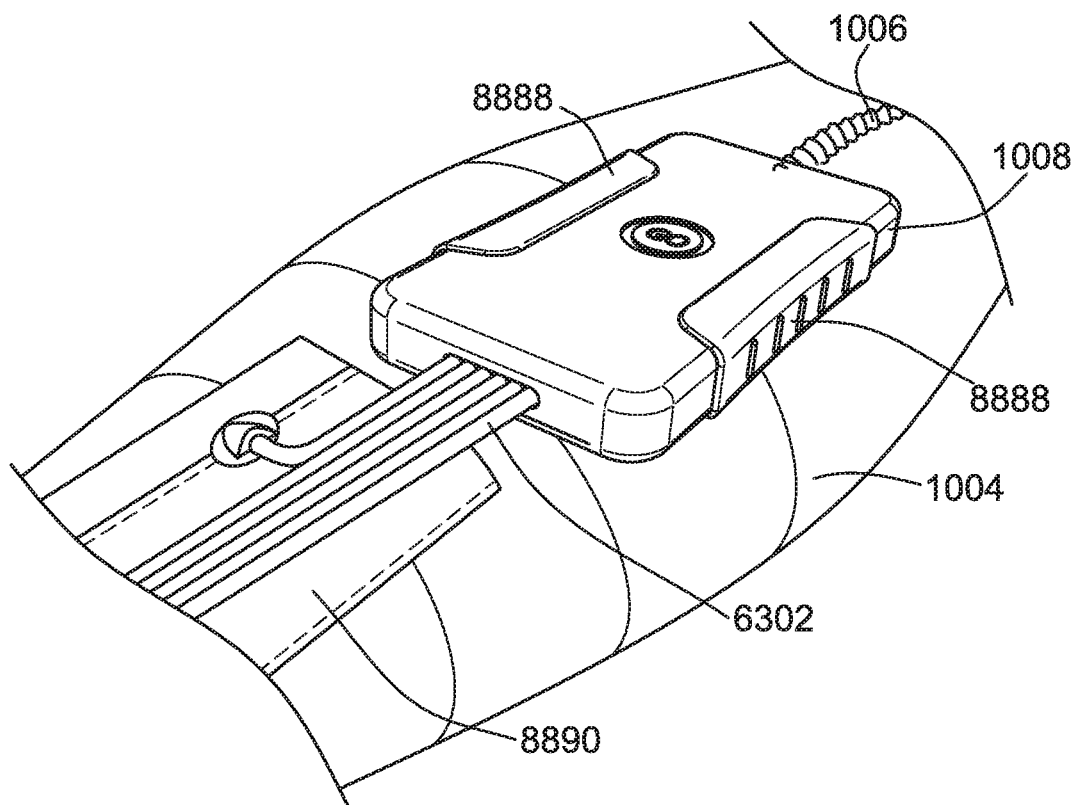
FIG. 8B is a partial perspective view of a compression garment with clips for holding an interface for controllable compression chambers, according to some implementations of the present disclosure.

The connection from the sixteen valves via the sixteen pneumatic connecting lines 6302 is further illustrated in relation to the interface shown in FIG. 7. The interface 7008, which is illustrated on a compression garment 1004 suitable for use on a lower leg and foot, has leads to connecting lines 7302 each in turn providing a pneumatic path to one of sixteen chambers 7304-1 through 7304-16 of the compression garment 1004.

Use of the conduit and/or valve interface 1008 with the system 1000 may be further considered in reference to FIGS. 8 to 11. In several versions, the interface 1008 may be a discrete component or unit that is removable or dis-connectable from the CPG device 1002 and the compression garment 1004. In some versions, the compression garment 1004 may be configured to couple to and retain the discrete component of the interface 1008, such when it includes the set of active valves 6297 for the operation of the compression garment 1004. For example, as illustrated in FIG. 8A, a compression garment 1004 (e.g., in the shape of a pair of pants) may be configured with a pocket 8886, such as a fabric pocket, to carry the interface 1008 when pneumatically and/or electrically coupled to the compression garment 1004. For example, a coupler opening in the base of the pocket may serve as a seat with pneumatic couplings that facilitate appropriate interfacing/coupling of the pneumatic connections from interface 1008 to the pneumatic pathways of the compression garment 1004. For another example, as illustrated in FIG. 8B, the compression garment 1004 includes a clip 8888 sized to hold the interface 1008 unit when coupled to the compression garment 1004. The clip 8888 may be proximate to a fabric channel 8890 or hem of the compression garment 1004, such as an added (sewn on) layer, within which the pneumatic connecting lines 6302 may run to their respective chamber connections.

Figure 9B:
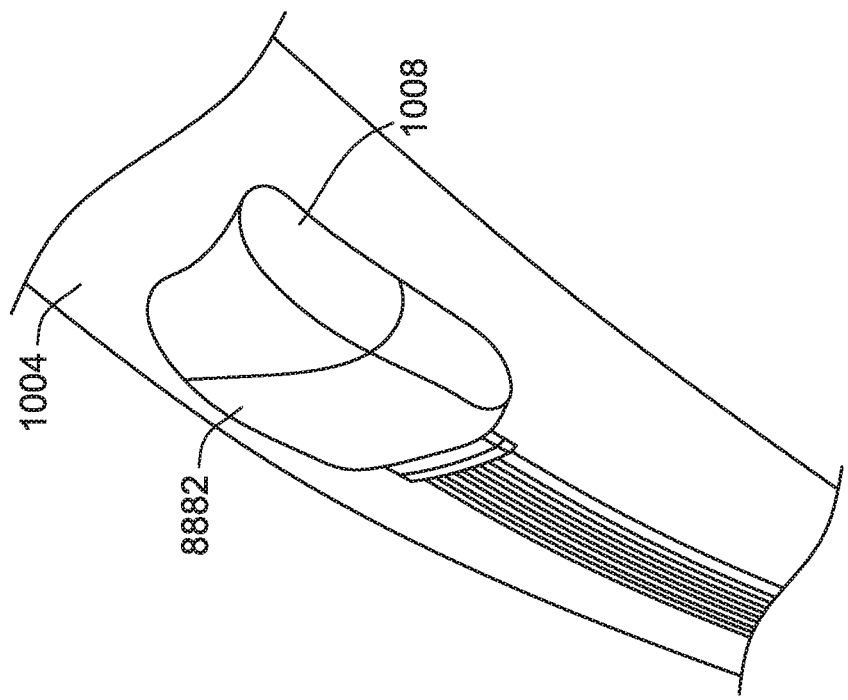
FIG. 9B is a partial perspective view of an interface-garment attachment mechanism, according to some implementations of the present disclosure.
Figure 9A:
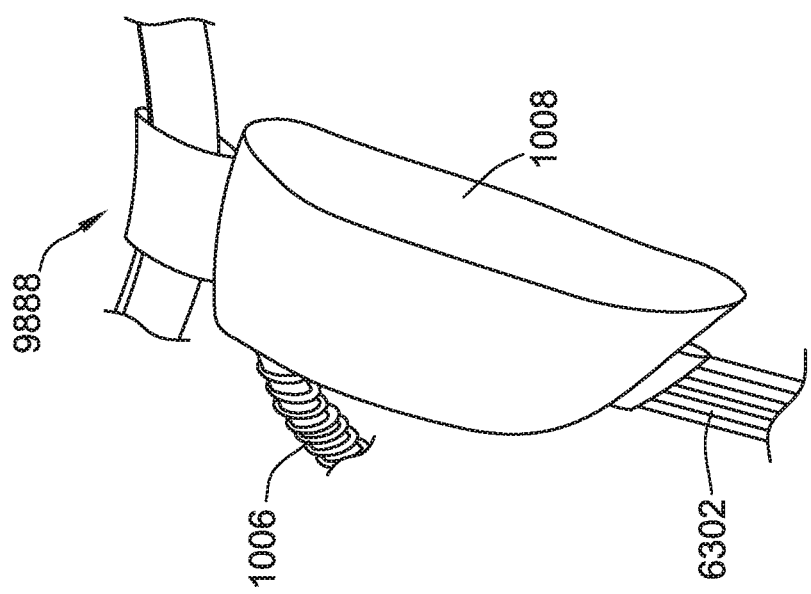
FIG. 9A is a partial perspective view of an interface-garment attachment mechanism, according to some implementations of the present disclosure.

Referring to FIG. 9A, a belt mount 9888, serves as a mechanism for carrying the interface 1008 when coupled to the compression garment 1004. Referring to FIG. 9B, a pocket 8882 of the compression garment 1004 (e.g., in the shape of a sleeve) serves as a mechanism for carrying the interface 1008.

Figure 10A:
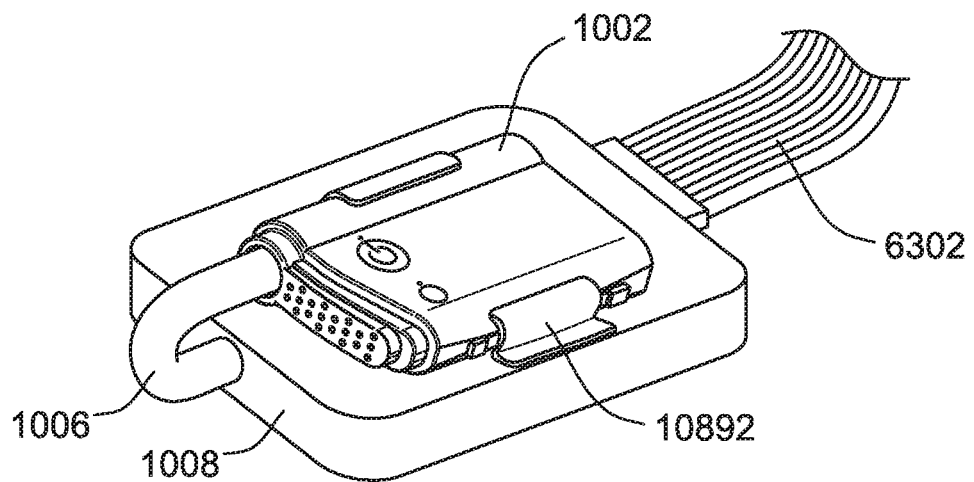
FIG. 10A is partial perspective view of an interface caddy with clips, according to some implementations of the present disclosure.
Figure 10B:
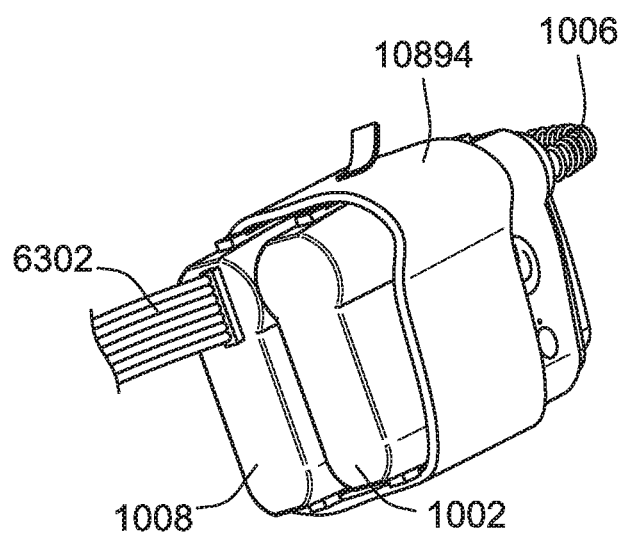
FIG. 10B is partial perspective view of a bundle sleeve, according to some implementations of the present disclosure.

Referring to FIG. 10A, the interface 1008 unit can include a clip 10892 for mounting the CPG device 1002 thereon. Referring to FIG. 10B, a bundle sleeve 10894 can be applied to the interface 1008 unit and the CPG device 1002 when they are pneumatically and electrically coupled to aid in keeping them joined together by the bundle sleeve 10894 as a common bundle.

Figure 11A:
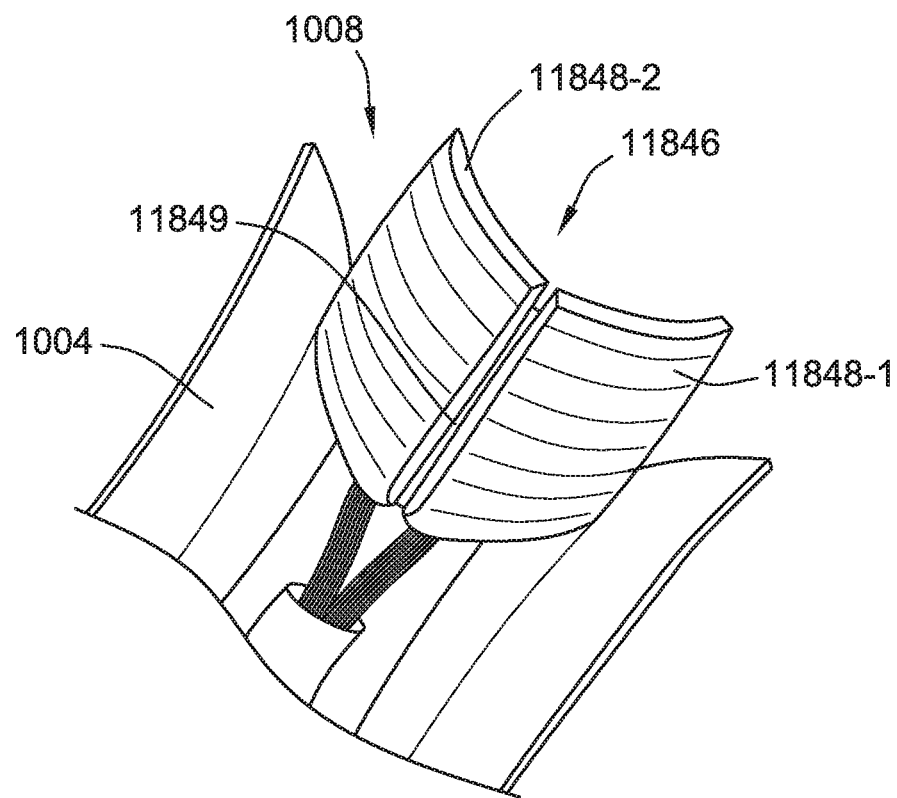
FIG. 11A is a partial perspective view of an interface with an anatomical housing, according to some implementations of the present disclosure.
Figure 11B:
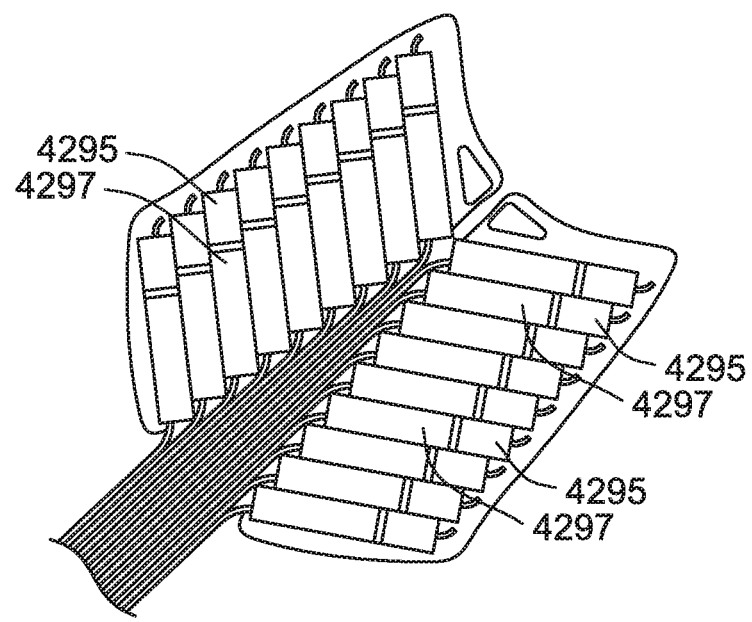
FIG. 11B is a partial perspective view of valves of the interface of FIG. 11A, according to some implementations of the present disclosure.

Referring to FIG. 11A, the interface 1008 unit can have a housing with an anatomical surface curvature 11846 to promote comfortable wearing when combined with the compression garment 1004. The interface 1008 unit may be formed with two wings 11848-1, 11848-2 that are joined by a flexible hinge 11849. Such a butterfly configuration can permit the interface 1008 unit to more readily conform to the shape of, by flexing around, the limb being treated with the joined compression garment 1004. Such a hinged structure 11849 also more readily permits movement of the interface 1008 with movement of the user for user comfort. Referring to FIG. 11B, in some such versions, the valves 4297 of the interface 1008 unit may be divided within the housing structure of each wing 11848-1, 11848-2 of the interface 1008 unit.

6.3 Passive Valve(s)

Although some versions of the valves interfacing with the CPG device 1002 may be active valves as controlled by the interface 1008, as discussed in more detail herein, some compression garments of the present disclosure can be implemented with passive valves. One or more passive valves may serve to complement the pneumatic operations of the chambers with the active valves and/or as an alternative to active valve implementation. Thus, in some cases, the interface 1008 may direct a pneumatic line to a chamber of the compression garment with a passive valve. Such a passive valve may serve as an inlet or an outlet to a chamber of the compression garment. Such a passive valve may open depending on a pressure condition applied to one side of the passive valve. In an example, such a passive valve may be implemented, for example, by a flexible flap having a chosen rigidity that is responsive to a desired pressure threshold condition. Such a valve may be a duckbill valve. Thus, when a desired pressure differential is achieved across the mechanism of the passive valve, the passive valve opens to permit air movement across the passive valve. Such a passive valve may be implemented as an aperture (or two or three or more apertures) with a flow restriction(s) to delay flow through the aperture(s) to permit different inflation timings between neighbouring chambers that are separated by the flow restricted aperture(s).

Figure 12A:
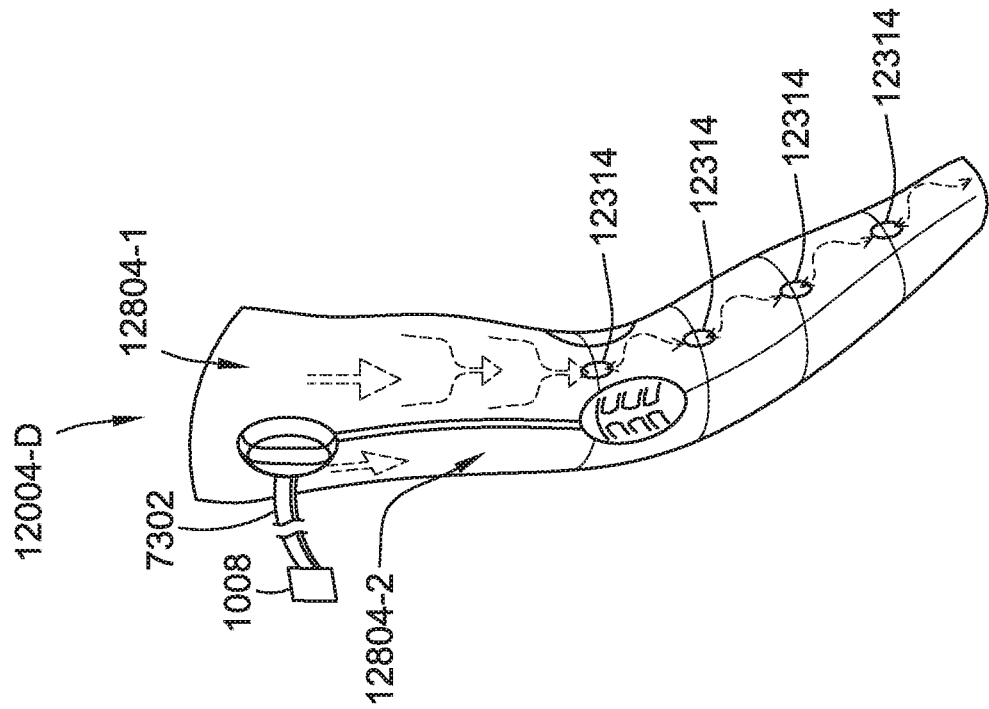
FIG. 12A is a partial perspective view of an arm compression garment for a compression therapy system, according to some implementations of the present disclosure.

For example, as illustrated in FIG. 12A, an active valve may be controlled to permit pneumatic inflation of a first chamber 12304-1 that is coupled to a pneumatic connecting line 7302 from the interface 1008. By operation of the CPG device 1002, air may be pumped into first chamber 12304-1. Upon achieving a pressure condition in the first chamber (which may provide initial compression in the vicinity of the first chamber), the flexibility threshold of the passive valve 12314 may be overcome so as to thereby open the passive valve 12314. The opening of the passive valve 12314 may then permit pneumatic inflation of a second chamber 12304-2 via the passive valve 12314 such that compression may be later (delayed in time) applied in the vicinity of the second chamber. Similarly, in other forms, a flow restriction of the passive valve 12314 may delay pressurization of the second chamber 12304-2 until after the first chamber 12304-1 has achieved a compressive pressure condition.

As shown in FIG. 12A, a series of such chambers 12304-1 to 12304-11 separated by such passive valves can permit a sequential inflation of the series of chambers. Such a sequential inflation can provide a sequential shifting of the leading edge of the compression force along the compression garment so that it has a directional vector in the direction of the series of chambers of the garment. In this way, a directional vector of compression (tangentially along the user's skin surface of the limb receiving therapy) proximate to each of the sequentially inflated chambers, can be provided with the passive valves. Such passive valves may, for example, be implemented with an applicator manipulation therapy as described in more detail herein, and may provide such a therapy with fewer active valves. By using such a series of passive valve(s) 12314 with interceding chambers, it can potentially reduce size of the garment as fewer active valves may be necessary.

Figure 12B:
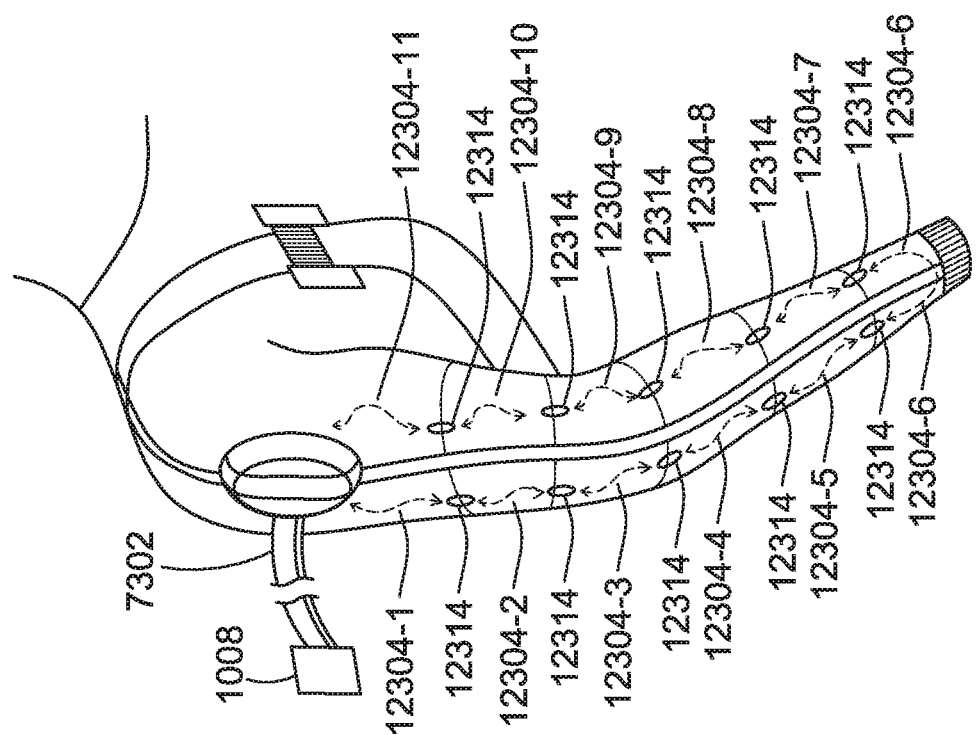
FIG. 12B is a partial perspective view of an arm compression garment for a compression therapy system, according to some implementations of the present disclosure.

Referring to FIG. 12B, an arm compression garment 12004-D includes a first series of chambers 12804-1, a second series of chambers 12804-2, and passive valves 12314 formed to provide a compression vector along an arm. The series 12804 of chambers and passive valves 12314 in the arm compression garment 12004-D provides a directional compression force vector that progresses towards the wrist from the upper arm. Alternatively, such chambers may be configured to provide the series of chambers 12804-1, 12804-2 and passive valves 12314 so that the directional compression force vector progresses towards the upper arm from the wrist. In some versions, different series of chambers and passive valves may be isolated so that different directional compression force vectors can be achieved in different parts of the compression garment. For example, one series may be configured to provide the directional compression force vector in a progression towards the elbow from the wrist and a different series may be configured to provide the directional compression force vector in a progression towards the upper arm from the elbow. Of course, additional series may provide for additional localization of the directional compression force vector.

Figure 12C:
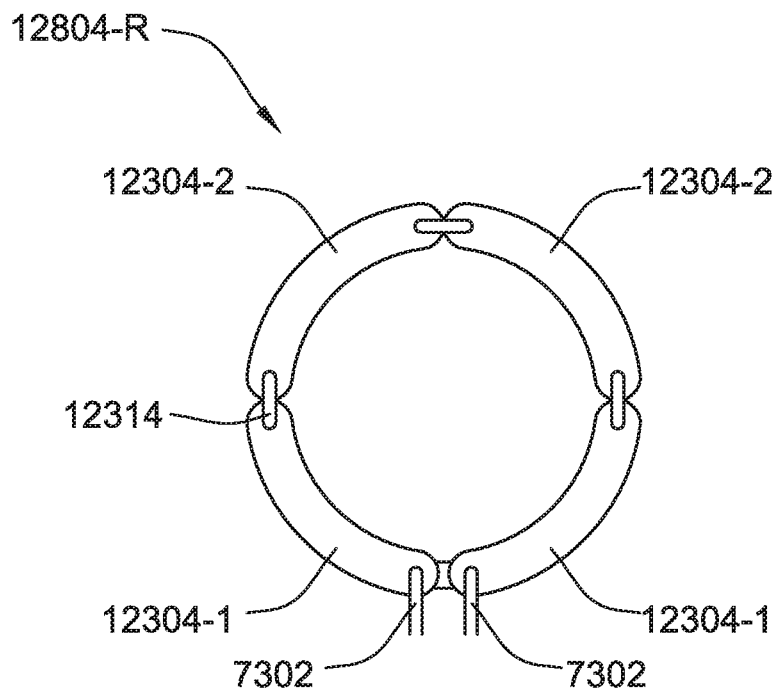
FIG. 12C is a plan view of a ring configuration of chambers, according to some implementations of the present disclosure.

In a further example illustrated in FIG. 12C, a circular directional compression force may be achieved, such as by a series 12804-R of passive valves 12314 and chambers 12304-1, 12304-2 in a ring configuration, such as about all or a portion of a periphery of a sleeve compression garment. As shown in relation to the series 12804-R, two first chambers 12304-1 may be inflated by connecting lines 7302. The connecting lines may optionally be coupled to one or two active valves and/or a manifold from a CPG device (e.g., CPG device 1002). Two second chambers 12304-2 may then inflate when a desired pressure differential is achieved across the passive valves 12314.

Figure 12D:
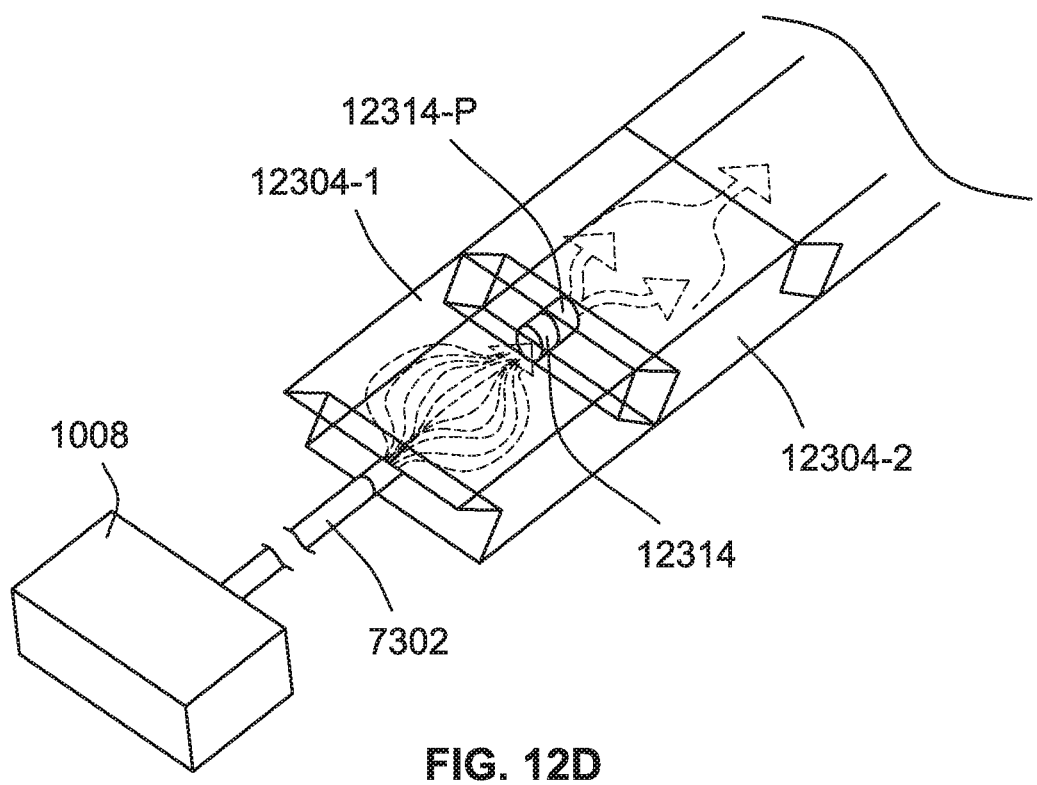
FIG. 12D is a partial perspective view of chambers with passive valves, according to some implementations of the present disclosure.

Another example of such a passive valve is illustrated in FIG. 12D. The passive valve 12314 may be implemented with an inter-chamber passage 12314-P that forms a small opening, such as a tubular opening, between neighbouring chambers 12304-1, 12304-2. The passage 12314-P becomes obstructed upon collapse of the chambers 12304-1, 12304-2 when air is withdrawn from the chambers 12304-1, 12304-2. Such a collapse is facilitated by a baffle design of the chambers 12304-1, 12304-2 and/or of the passive valve that enables collapse of the inter-chamber passage 12314-P. The collapse of the chambers 12304-1, 12304-2 collapses the passage 12314-P that is formed in the baffle. Expansion of the baffle upon sufficient inflation of the chamber permits opening of the passage for the sequential inflation described herein.

6.4 Compression Garment

As described herein, a compression garment 1004 includes a set of pneumatic chambers that may be inflated and/or deflated by operation of the CPG device 1002 via one or more pneumatic lines leading to the pneumatic chambers of the compression garment 1004. Such activation may be implemented with one or more active valves and/or passive valves. The garment may typically be lightweight, flexible and washable and may employ a compression fabric.

In some implementations, the garment is formed with layers, such as an inner layer (e.g., inner sleeve) and an outer later (e.g., outer sleeve). The garment may be manufactured with a breathable fabric, serving as an inner skin contact interface. Such a material may serve as a barrier to direct user contact with a less permeable material that forms a set of pneumatic chambers of the garment. In some implementations, one or more layers of the garment (e.g., the skin contacting layer) includes polyester, elastane, nylon, and thermoplastic polyurethane (TPU). In some such implementations, the TPU is used as a backing to aid in making the garment airtight or near airtight. The proportion of polyester, elastane, and nylon can be adjusted to modify the elasticity of the garment (e.g., the skin contacting layer). In some implementations, a weave technique of one or more layers of the garment can be adjusted to modify the elasticity of the garment.

The chambers and pneumatic paths may be formed between the layers. In some forms, the outer layer may be made of a three-dimensional knitted fabric. The outer layer may include one or more moulded portions, such as in a form of a brace, to more rigidly support certain anatomical regions of the limb (e.g., a forearm brace or leg brace) such as along one side of the sleeve. Some areas of the garment may include stretchable or flexible regions to permit movement (e.g., elbow, wrist, ankle or knee regions). Moreover, moulded regions may include pneumatic couplings and/or pneumatic pathways. Such component regions (e.g., of thermoplastic elastomer TPE such as Santoprene) may be sewn into the fabric of the garment, co-moulded, or ultrasonically welded to the fabric.

The garment may be generally formed as a sleeve that can be applied around the bodily area of therapy. For example, it may be an arm sleeve, a partial arm sleeve, an above-the-knee leg sleeve, a full leg sleeve, a foot sleeve, a toe-to-thigh sleeve, an ankle-to-knee sleeve, etc.

As previously discussed and as illustrated in FIG. 7, the compression garment 1004 can include a set of pneumatic chambers 7304-1 to 7304-16 positioned about the compression garment 1004 that are sized and located to promote a desired compression therapy. As shown, the compression garment 1004 is a lower leg type compression garment with a partial upper foot portion and a leg portion that each provides different sets of chambers or cells for separately compressing discrete portions of the foot and/or leg that are covered by the compression garment 1004. Each chamber forms a semi or fully peripheral ring about a tubular portion of the sleeve. The chamber rings are located along the length of the sleeve, resulting in sixteen controllable chambers. These chambers may be activated in zones. As shown, the compression garment 1004 includes a set of chambers in a knee-thigh zone KTZ (e.g., chambers 15 and 16), a set of chambers in a calf-knee zone CKZ (e.g., chambers 10, 11, 12, 13 and 14), and a set of chambers in a foot-calf zone FCZ (e.g., chambers 1, 2, 3, 4, 5, 6, 7, 8 and 9).

The pneumatic chambers 1-16 may be formed with a material having baffles (e.g., chamber material folds) to more readily permit a vertical expansion of the chamber, where the baffles are the same or similar to that shown in FIG. 12D and described above. The pneumatic chamber 12304-1 (FIG. 12D) may be box shaped with one or more edge folds, such as at each of an inlet end and an outlet end. Such folds may also be at sides of the chamber (not illustrated). Such folds can permit a more uniform rising of the user side surface of the box to provide a more evenly applied compression surface area such as when compared to a more rounded, balloon-shaped type of chamber. Each chamber can provide an isolated compressive force at the surface of the chamber in contact with a user from inflation of the pneumatic chamber, such as in relation to activation of an active valve and/or passive valve, in the location of the inflation. Multiple chambers can be activated to distribute the compressive force. They may also be sequentially activated to move the location of the compressive force.

The compression garment(s) of the present disclosure may also include, or be configured to retain, pneumatic pathways (such as in moulded regions) or conduits inserted therein to fluidically couple pneumatic connecting lines 6302 (FIGS. 6 and 7), such as from the interface 1008 and/or the CPG device 1002 for pneumatic purposes, to the pneumatic chambers of the compression garment. Such pathways may also couple discrete pneumatic chambers together, such as when the chambers are separated by a passive valve. In some versions, one active valve may direct gas flow via such a conduit or pathway in relation to one pneumatic chamber or in relation to a group of pneumatic chambers. Thus, a pathway of the compression garment may couple a group of pneumatic chambers or a single pneumatic chamber. Thus, in some cases different active valves may be coupled to different pneumatic chambers or different groups of pneumatic chambers via the pathways of the compression garment. In some versions, the compression garment may include integrated active valves. In some versions, the compression garment may include couplers for attachment of pneumatic conduits and/or electrical lines such as to the integrated active valves. In such cases, a controlled compression zone may be considered a set of one or more pneumatic chambers that may be operated by one or more active valve sets by a controller of the CPG device. Such a zone of chambers may also employ passive valves.

The compression garment(s) of the present disclosure may also include sensors, such as pressure, strain, flow, temperature, electrodes, or any combination thereof. When measuring skin characteristics, such sensors may be located on a layer of the compression garment to permit skin contact. For example, a temperature sensor, strain sensor and/or a set of electrodes may be in one or more of the zones of the compression garment such as at an inner layer of the garment. Integrated pressure, flow, and/or temperature sensors may be located to measure a characteristic of the pneumatic pathway(s) of the garment. In some versions, strain gauge sensors may be implemented in the garment to measure compression strain of the garment in one or more different zones of the garment. Measurements from such sensors may be used by the CPG device 1002.

Various configurations of the compression garment(s) of the present disclosure can be provided based on the type of compression therapy and target portion of the body of the user (e.g., patient). Additional examples of compression garments of the present disclosure are shown in FIGS. 13 to 22, which are discussed in detail herein.

Figure 13A:
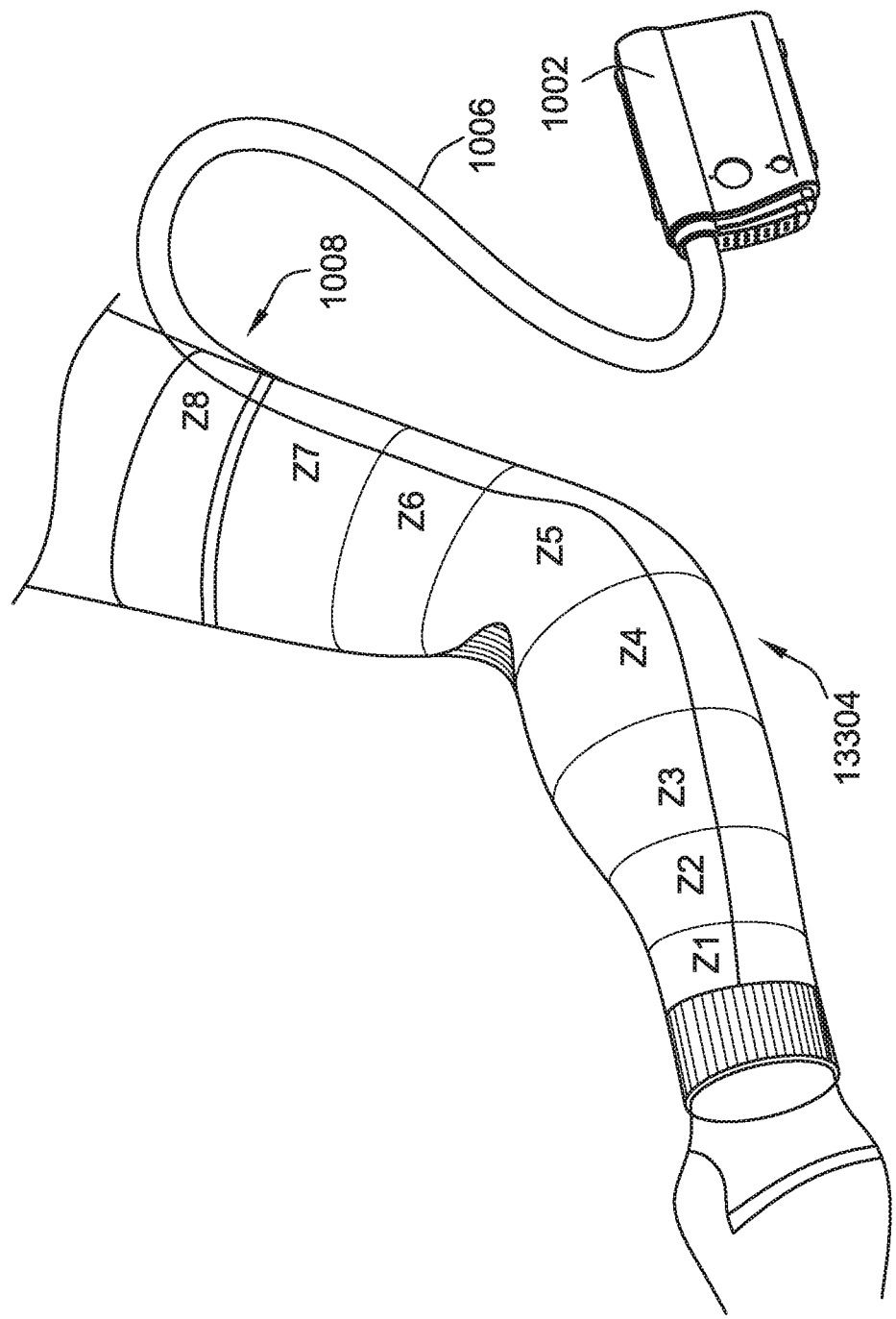
FIG. 13A is a perspective view of an arm compression garment system, according to some implementations of the present disclosure.
Figure 13B:
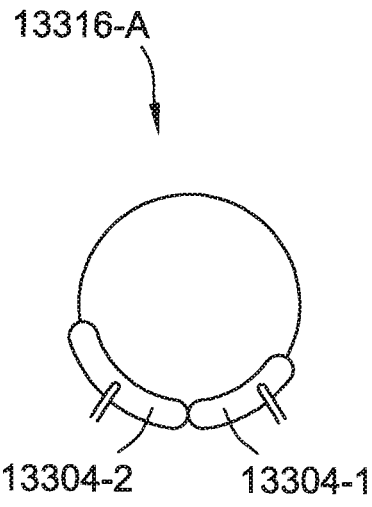
FIG. 13B is a plan view of a ring configuration of chambers, according to some implementations of the present disclosure.

Referring to FIG. 13A, an arm type compression garment 13304 is shown. The compression garment 13304 has multiple controlled compression zones Z1-Z8. The compressive garment 13304 can implement compression areas (e.g., areas 13316-A, 13316-B, 13316-C) about the periphery of the sleeve with different chamber configurations. For example, as shown in FIG. 13B, a peripheral compressive area 13316-A (shown in a plan view of a cross section of the sleeve 13304) may be formed with a semi-peripheral chamber configuration. In this configuration, peripheral compression is achieved by inflation of one or more chambers 13304-1, 13304-2, which are positioned on only a portion of the periphery of the sleeve 13304. In such a peripheral compressive area 13316-A, inflation of chambers along one side of the periphery of the sleeve 13304 effects a tightening of the sleeve with a material on the opposing peripheral side of the sleeve 13304. Such a configuration may have one or more pneumatic chambers that may employ one or more active valves and one or more passive valves.

Figure 13C:
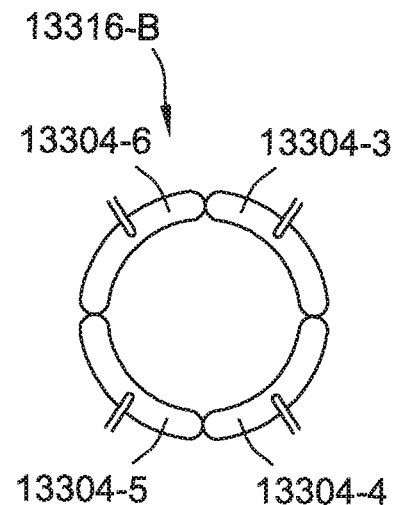
FIG. 13C is a plan view of a ring configuration of chambers, according to some implementations of the present disclosure.

Referring to FIG. 13C, another peripheral compressive area 13316-B (also shown in a plan view of a cross section of the sleeve) may be implemented by locating chambers substantially about the entire periphery of the sleeve 13304. For example, as shown in the peripheral compressive area 13316-B, four pneumatic chambers 13304-3, 13304-4, 13304-5, 13304-6 encircle the periphery of the sleeve. Each may be independently controlled by an active valve.

Figure 13D:
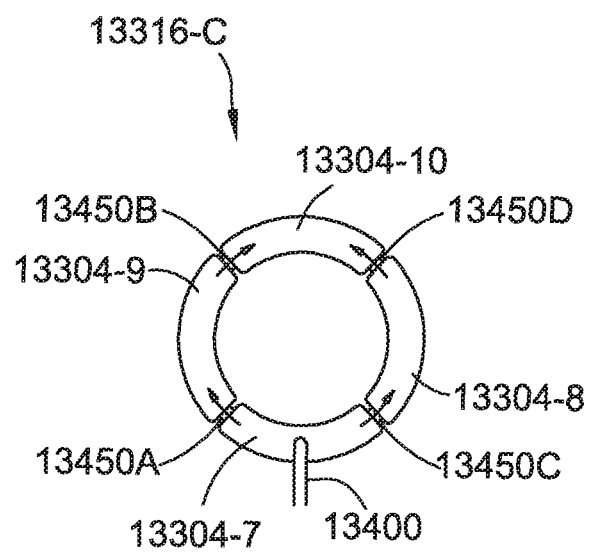
FIG. 13D is a plan view of a ring configuration of chambers, according to some implementations of the present disclosure.

Referring to FIG. 13D, a peripheral compressive area 13316-C includes four pneumatic chambers 13304-7, 13304-8, 13304-9, 13304-10 that encircle the periphery of the sleeve 13304. In this area, one of the pneumatic chambers is controlled by an active valve and the remaining series of chambers are inflated by interceding passive valves 13450A-D. Although these peripheral area sections show four chambers, fewer or more such chambers (e.g., 2, 5, 6, 7, 10, 20, 50, 100, 1000, etc. or any number in-between, less, or more) may be implemented to encircle the sleeve 13304 as desired. As illustrated in the grid on the compression garment 13304 of FIG. 13A, each discrete zone Z1, Z2, Z3, Z4, Z5, Z6, Z7, and Z8 along the length of the sleeve 13304 may have one peripheral compressive area (e.g., areas 13316-A, 13316-B, 13316-C) in any of the configurations discussed in relation to FIGS. 13B-13D. Fewer or more such zones (e.g., 2, 4, 10, 20, 50 etc.) may be provided, which may depend, for example, on the number of active valves provided in the system 1000 (FIG. 1).

Figure 14:
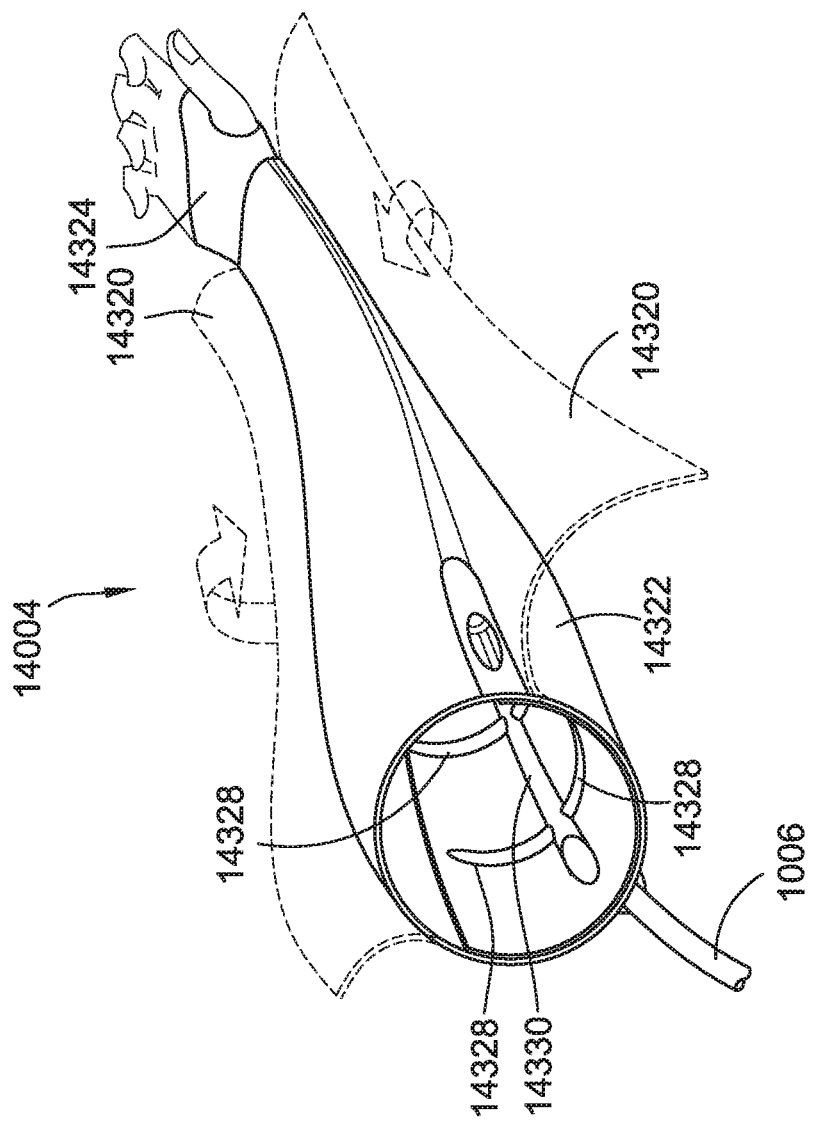
FIG. 14 is a perspective view of an arm compression garment prior to being fully assembled (e.g., unwrapped), according to some implementations of the present disclosure.

Referring to FIG. 14, an arm compression garment 14004 includes a compression fabric (e.g. spandex and/or nylon) outer layer 14320, which may be applied to a moulded TPE (e.g., Santoprene) that forms an inner layer 14322 exo-skeleton of the limb. An inner skin contact membrane 14324 may be applied under the exo-skeleton layer 14322. As shown, a portion of an optional membrane 14324 is shown as extending onto a hand portion of the user. The moulded exo-skeleton structure may be formed (moulded) with pathways that serve as a flexible pneumatic manifold to direct airflow about the compression garment 14004 to the localized chambers of the garment 14004. Such a pathway may be provided with one or more trunk paths 14330 extending along the length of the sleeve 14004 and the pathway may have multiple semi-peripheral branch paths 14328 leading to discrete chambers that are formed between the moulded exo-skeleton layer 14322 and the inner skin contact layer and/or between the outer layer 14320 and the moulded exo-skeleton layer 14322. An end of the trunk path 14330 may be moulded as, or to, a coupler for removable connectability of a pneumatic line from the interface 1008 and/or the CPG device 1002 (FIG. 1).

Figure 15:
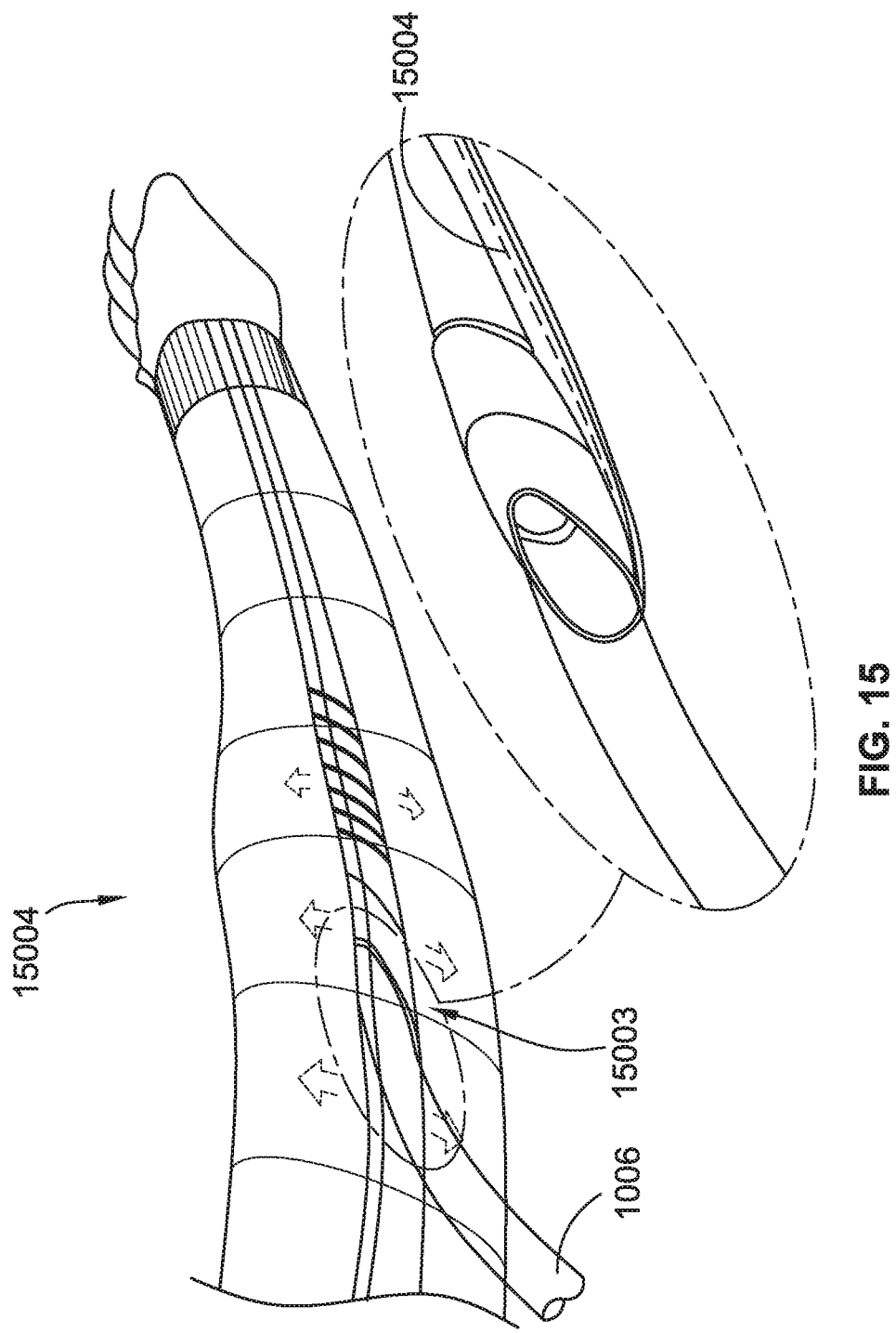
FIG. 15 is a perspective view of the arm compression garment of FIG. 14 fully assembled (e.g., wrapped up).

Referring to FIG. 15, a pneumatic coupler 15003 is shown as being sewn or stitched, for example, via thread 15400, into a compression garment 15004, which is the same as, or similar to, the compression garment 14004.

Figure 16:
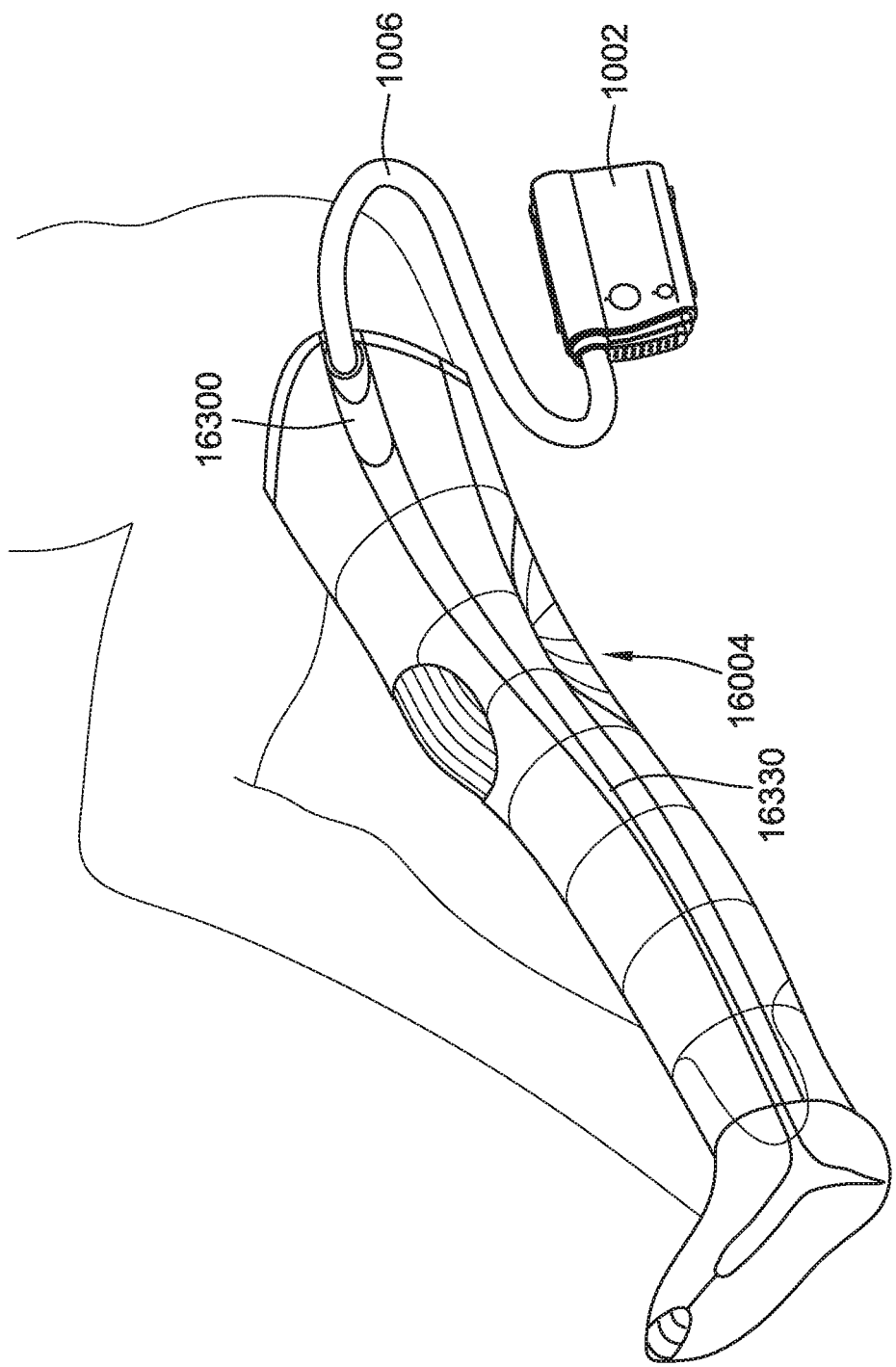
FIG. 16 is a perspective view of a compression therapy system including a leg compression garment, according to some implementations of the present disclosure.
Figure 17:
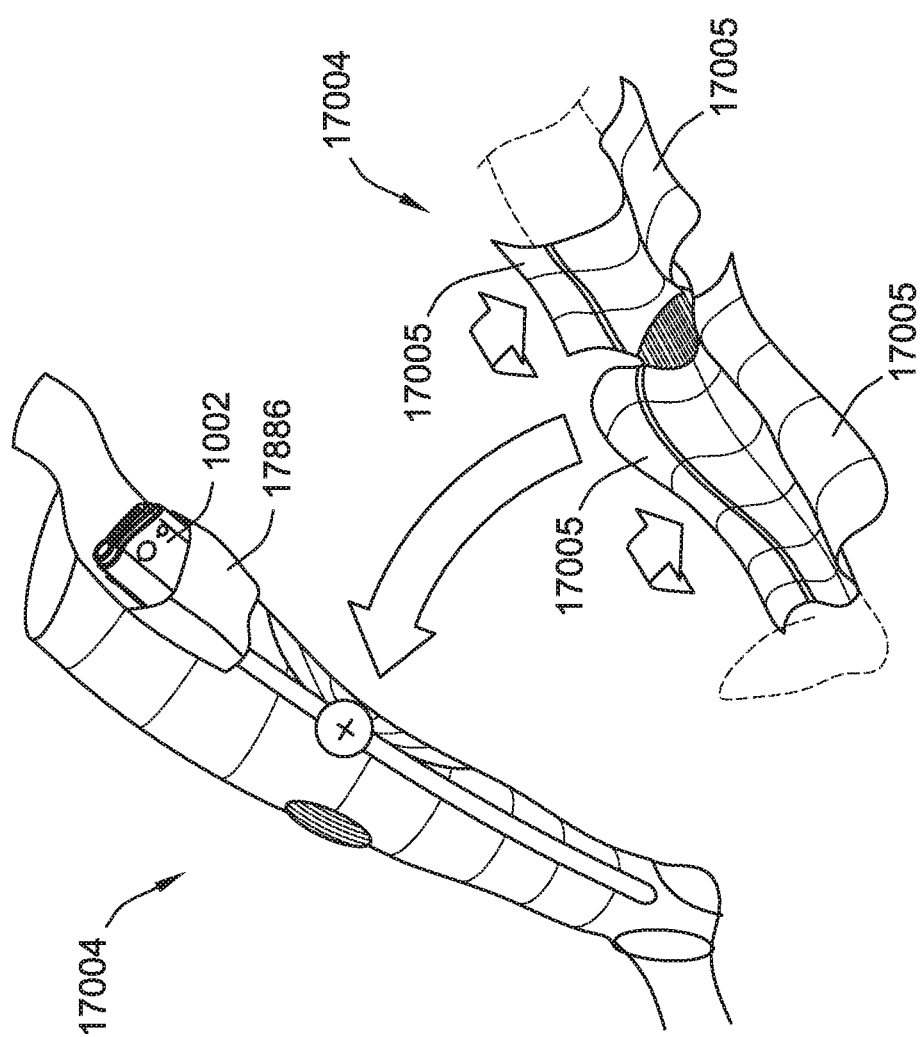
FIG. 17 is a perspective view of a compression therapy system including a leg compression garment, according to some implementations of the present disclosure.
Figure 18:
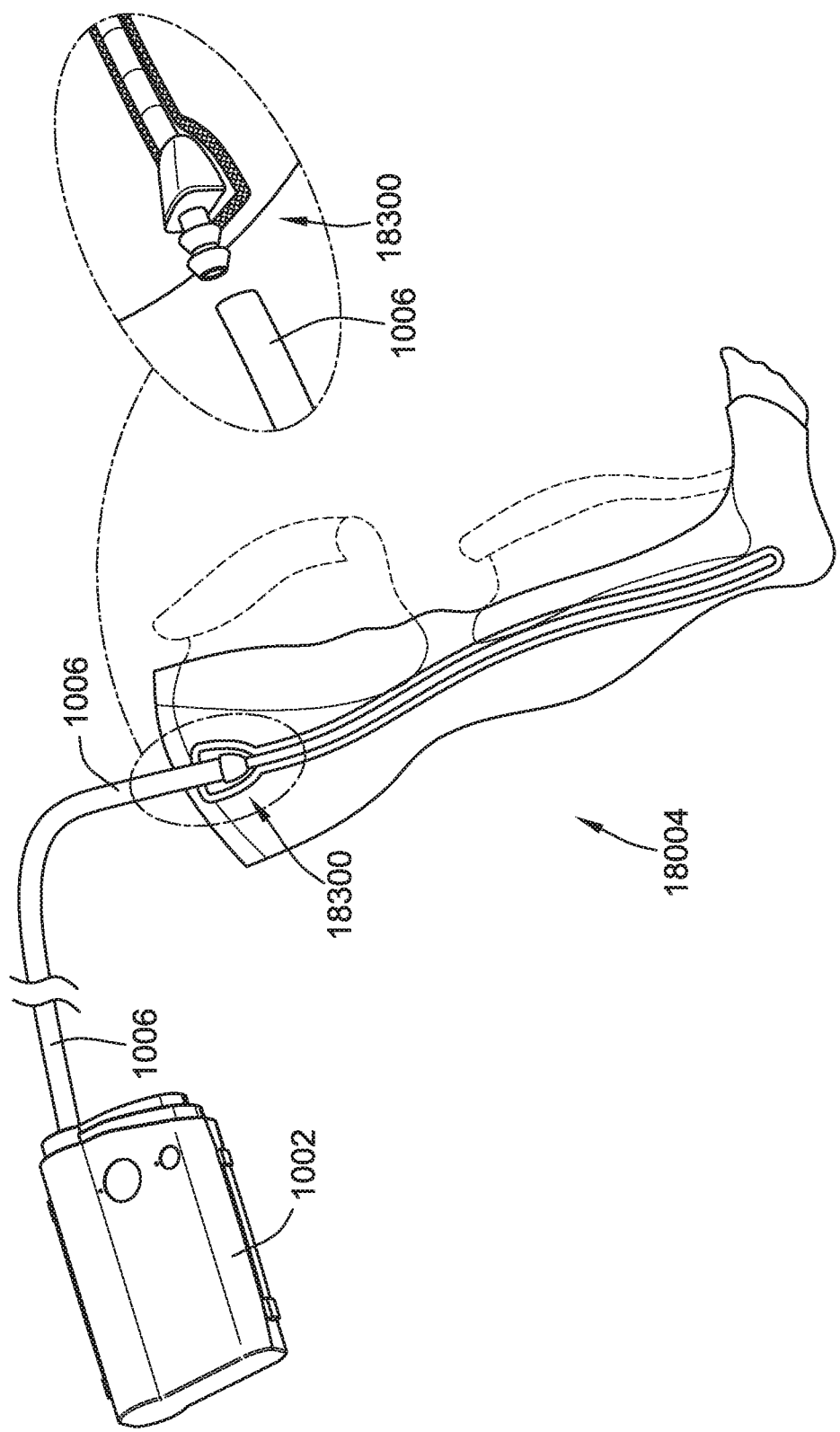
FIG. 18 is a perspective view of a compression therapy system including a leg compression garment, according to some implementations of the present disclosure.

Some versions of the compression garments of the present disclosure are designed for leg and/or foot therapies/compression. Examples of such leg and/or foot/boot compression garments are illustrated in FIGS. 16, 17 and 18. Referring to FIG. 16, a coupler 16300 is moulded to a compression garment 16004 to lead to directly to a trunk line 16330 (and indirectly to the branch lines) of the integrated pneumatic path of an exo-skeleton.

Referring to FIG. 17, a compression garment 17004 includes an integrated pocket 17886 (such as with an internal pneumatic seat to couple to an outlet of the CPG device 1002 and/or interface 1008 as previously described) for holding the CPG device 1002 and/or interface 1008. The compression garment 17004 may be applied by wrapping one or more portions/flaps 17005 of the garment 17004 onto a leg of a user. Such a wrapping may employ hook and loop material fasteners (e.g., Velcro) along the wrap edges so that the wrapped edges form a sleeve to provide the compression during use. Such a wrapping design may be implemented with any other of the compression garments of the present disclosure (e.g., arm, foot, etc.).

Referring to FIG. 18, a compression garment 18004 includes a barbed type coupler 18300 (shown connected and exploded) for establishing a pneumatic connection between the compression garment 18004 and the CPG device 1002 via the link 1006. Such a coupler 18300 may be co-moulded with the exo-skeleton structure, sewn/stitched into the fabric or ultrasonically welded to the fabric.

Figure 19:
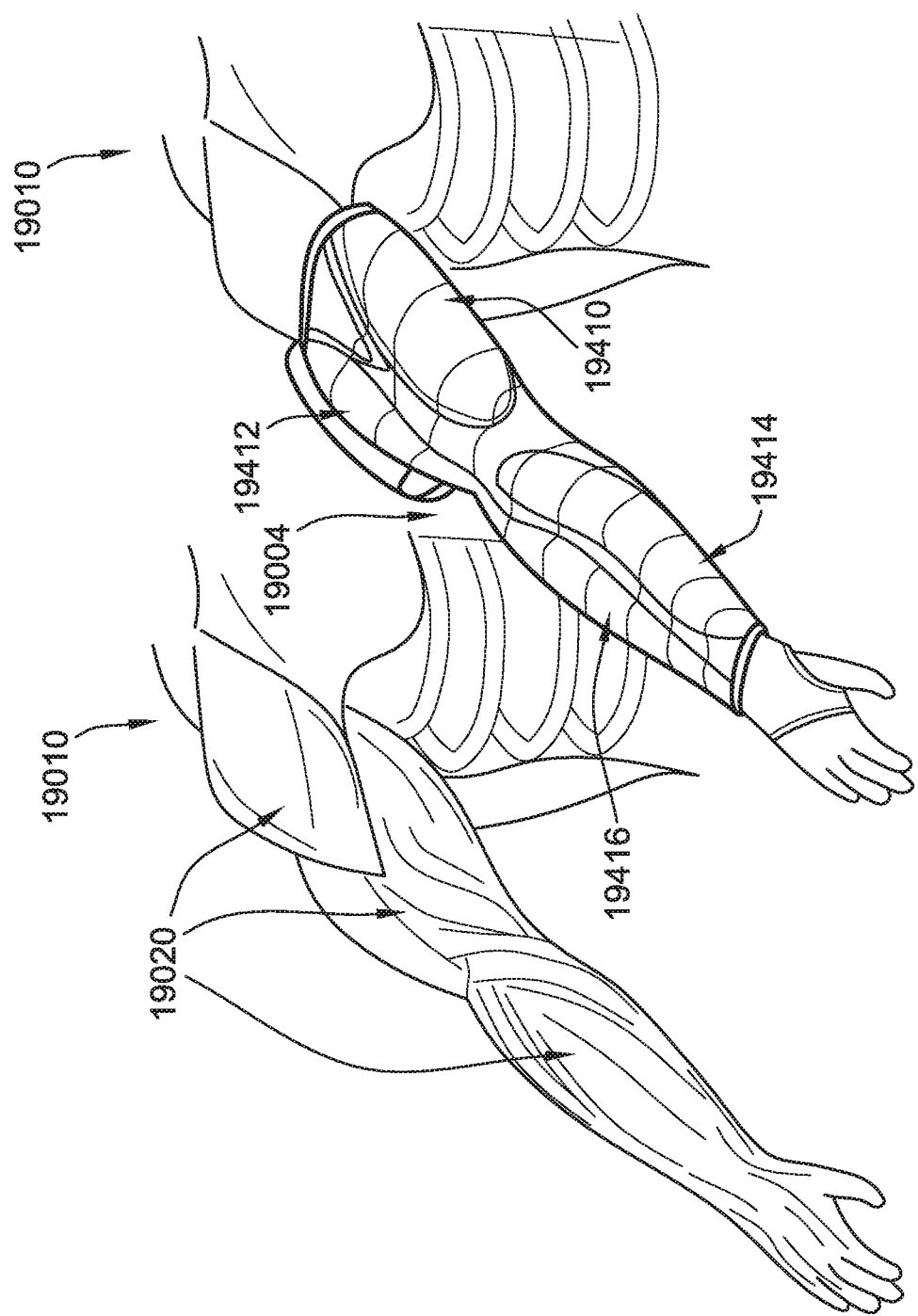
FIG. 19 is a perspective view of an arm compression garment with anatomically shaped chambers, according to some implementations of the present disclosure.
Figure 20:
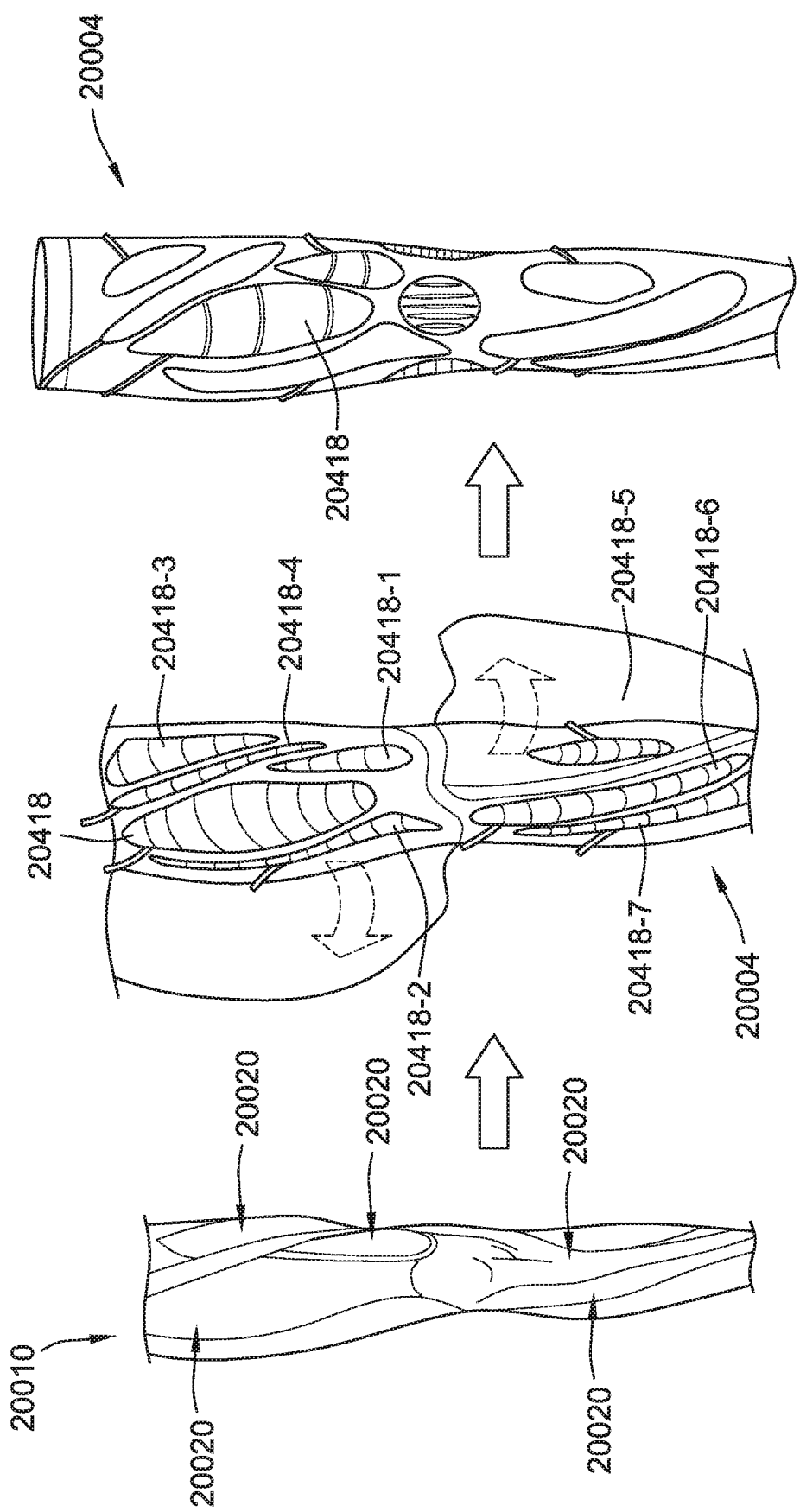
FIG. 20 is a perspective view of a leg compression garment with anatomically shaped chambers, according to some implementations of the present disclosure.

In some versions of the compression garment, one or more anatomically shaped pneumatic chambers may provide muscular based zones (anatomically shaped surfaces of the pneumatic chambers) for focused compression therapy. Examples of such compression garments are illustrated in FIGS. 19 and 20. Such muscular based zones, such as for location at the major muscle groups of the arms or legs, can provide targeted manipulation of each muscle area to support lymphatic function and blood flow. In some versions, knitted fabric can separate the set of pneumatic chambers (one or more) in each muscle zone from other muscle zones.

Referring to FIG. 19, an arm compression garment 19004 has one or more chambers in a zone shaped to target one or more muscles or groups of muscles 19020 of an arm of a user 19010, such as, for example, triceps brachii, biceps brachii, brachialis, brachioradialis, extensor carpi ulnaris, extensor digiti minimi, extensor digitorum, flexor carpi radialis, flexor carpi ulnaris, etc., or any combination thereof. In one such example, a bicep zone 19410 may have a set of chambers (e.g., one to four) that can be controlled to target the bicep zone such that activation of the chambers provides a compression therapy to an area limited to the bicep muscle. Similarly, a tricep zone 19412 may have a set of chambers (e.g., one to four) that can be controlled to target the tricep zone such that activation of the chambers provides a compression therapy to an area limited to the tricep muscle. Similarly, a brachioradialis zone 19414 may have a set of chambers (e.g., one to four) that can be controlled to target the brachioradialis zone such that activation of the chambers provides a compression therapy to an area limited to the brachioradialis muscle. Similarly, a flexor carpi ulnaris zone 19416 may have a set of chambers (e.g., one to four) that can be controlled to target the flexor carpi ulnaris zone such that activation of the chambers provides a compression therapy to an area limited to the flexor carpi ulnaris muscle.

Referring to FIG. 20, a bare leg (left side of FIG. 20) of user 20010 is shown being wrapped (middle of FIG. 20) with a compression garment 20004 (fully installed on the right side of FIG. 20) for supplying targeted leg muscle compression therapy. Similar to the arm compression garment 19004, a leg muscle zone 20418 (e.g., rectus femoris) may have a set of chambers (e.g., one to four) that can be controlled to target the leg muscle zone such that activation of the chambers provides a compression therapy to a surface area limited to the targeted leg muscle 20020. Such zones of the compression garment 20004 as a vastus medialis zone 20418-1, a vastus latoralis zone 20418-2, adductor magnus zone 20418-3, sartorius zone 20418-4, gastrocnemius (medial head) zone 20418-5, tibialis anterior zone 20418-6, extensor digitorum longus zone 20418-7, etc., or any combination thereof, may target respective leg muscles 20020.

In some versions, the compression garments of the present disclosure comprise anatomically located chambers based on the key points which a physical therapist focuses on when performing Manual Lymphatic Drainage (MLD). As an example, for Lower Limb lymphedema, these points may be inner to outer thigh, behind the knee, the sides of the calf, around the ankle and extremities. This enables the system 1000 to emulate MLD accurately. Such points may each be implemented as one or more zones and may be configured with active and/or passive valves to produce the desired directional manipulation of the points as previously discussed.

Figure 21:
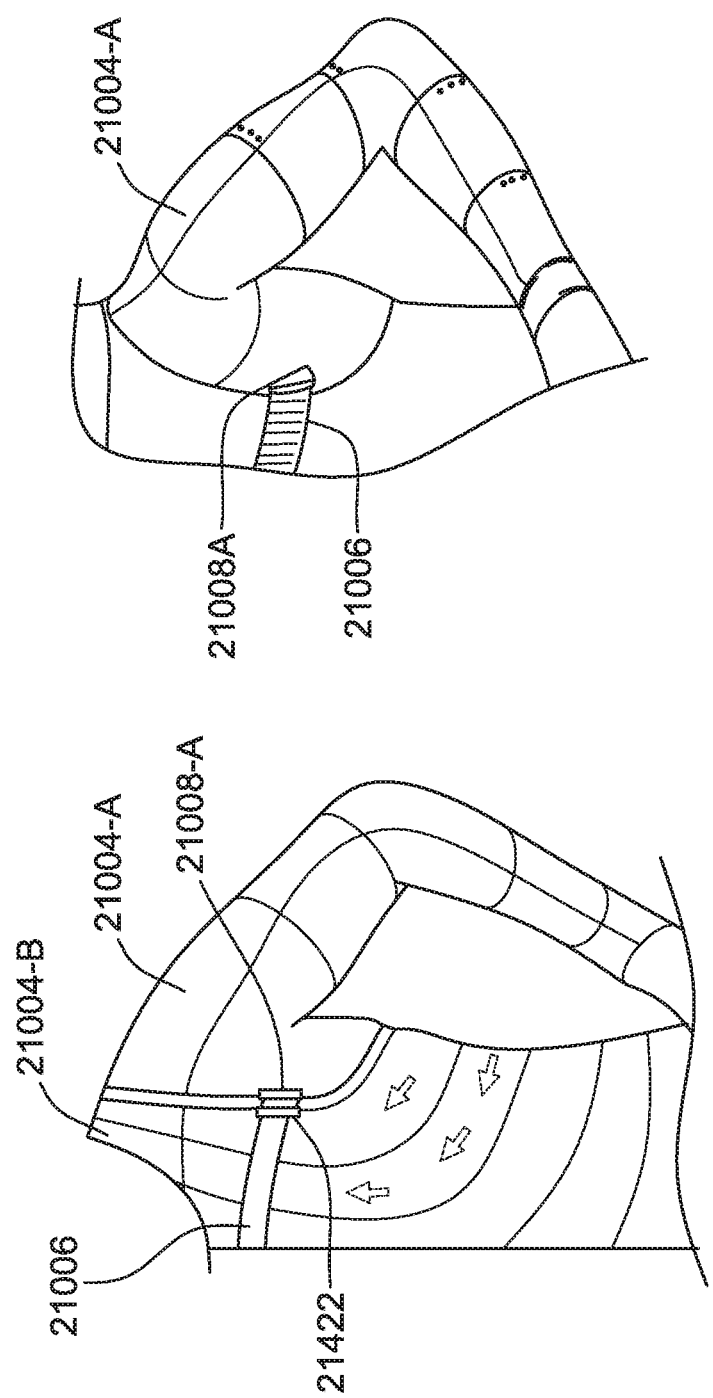
FIG. 21 is a perspective view of modular compression garments for an arm and torso of a user, according to some implementations of the present disclosure.

In some versions, the compression garments of the present disclosure may be implemented with a modular configuration to permit use of multiple garments with a common CPG device 1002. Referring to FIG. 21, an arm and shoulder compression garment 21004-A is worn over the arm and shoulder for receiving a compression therapy in various zones of the shoulder and arm. A conduit and valve interface 21008-A is configured with a coupler for connecting to the CPG device 1004 by the link 21006. The user may also use torso compression sleeve 21004-B, such as with wrapped edges as previously discussed. The torso compression sleeve 21004-B is formed to complement the arm and shoulder compression garment 21004-A. In this regard, a region of the conduit and valve interface 21008-A on the garment 21004-A may be located at a region of a chaining interface 21422 on the garment 21004-B. Thus, when both garments are worn, the chaining interface 21422 and the conduit and valve interface 21008-A may connect to permit pneumatic and/or electrical communication between the components of the garments 21004-A and 21004-B. In such a case, a separate conduit and valve interface are not necessary to be coupled to the CPG device 1002. Thus, air pressure for the activation of the compression of the second garment (e.g., torso garment 21004-B) may be delivered from the CPG device 1002 through the pathways and/or wires of the first garment (arm and shoulder garment 21004-A).

Figure 22:
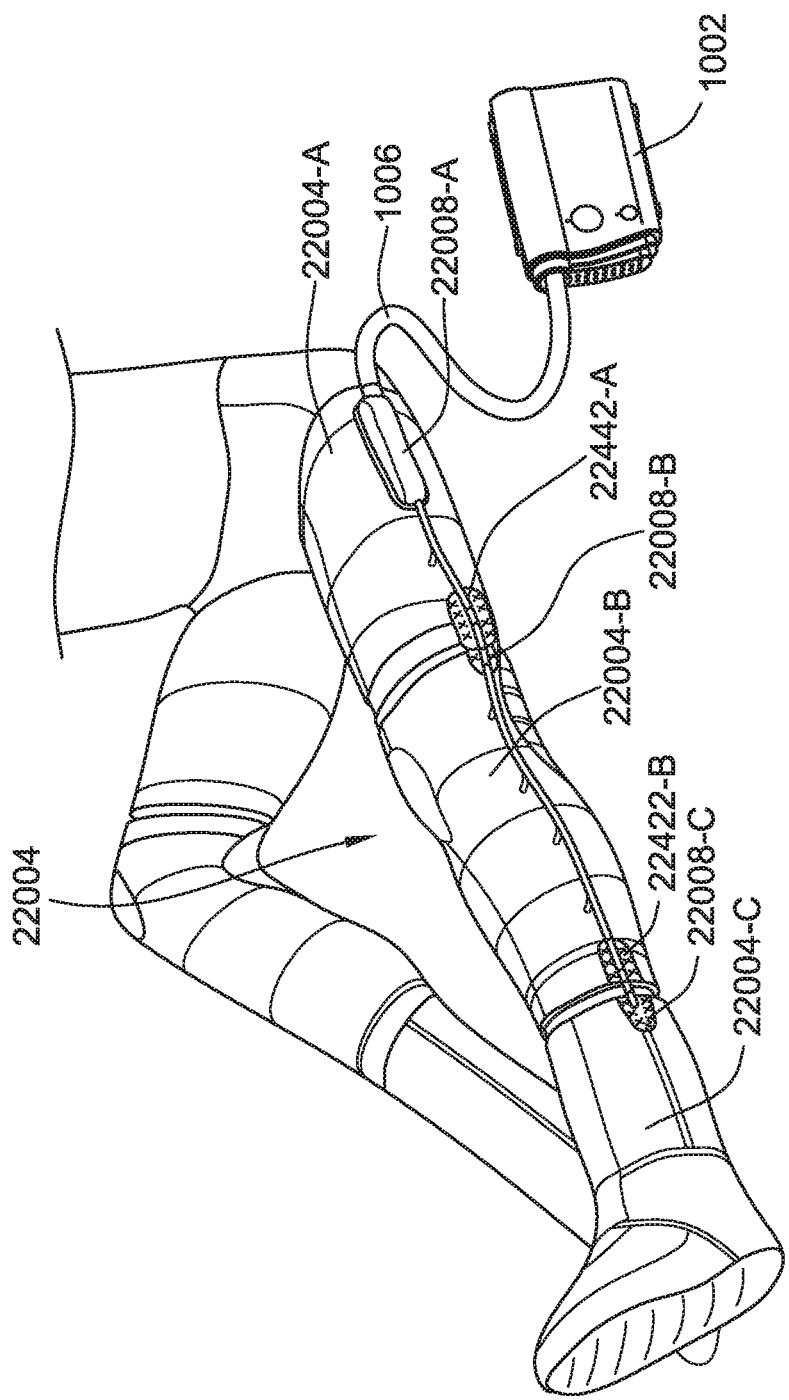
FIG. 22 is a perspective view of a compression therapy system including a modular compression garment for a leg and foot of a user, according to some implementations of the present disclosure.

Referring to FIG. 22, another modular compression garment 22004 is shown as including an upper leg compression garment 22004-A, a lower leg compression garment 22004-B, and a boot compression garment 22004-C. As shown, the upper leg compression garment 22004-A and lower leg compression garment 22004-B each have a chaining interface (22422-A and 22422-B respective) located in a region of the respective garments for direct coupling to a conduit and valve interface (22008-B and 22008-C respectively) of a neighbouring garment. Thus, compression therapy of the several garments may be implemented by bussing signals (pneumatic and electrical) through the respectively coupled garments with a single CPG device 1002 connected to the modular compression garment 22004 via interface 22008-A.

Figure 23:
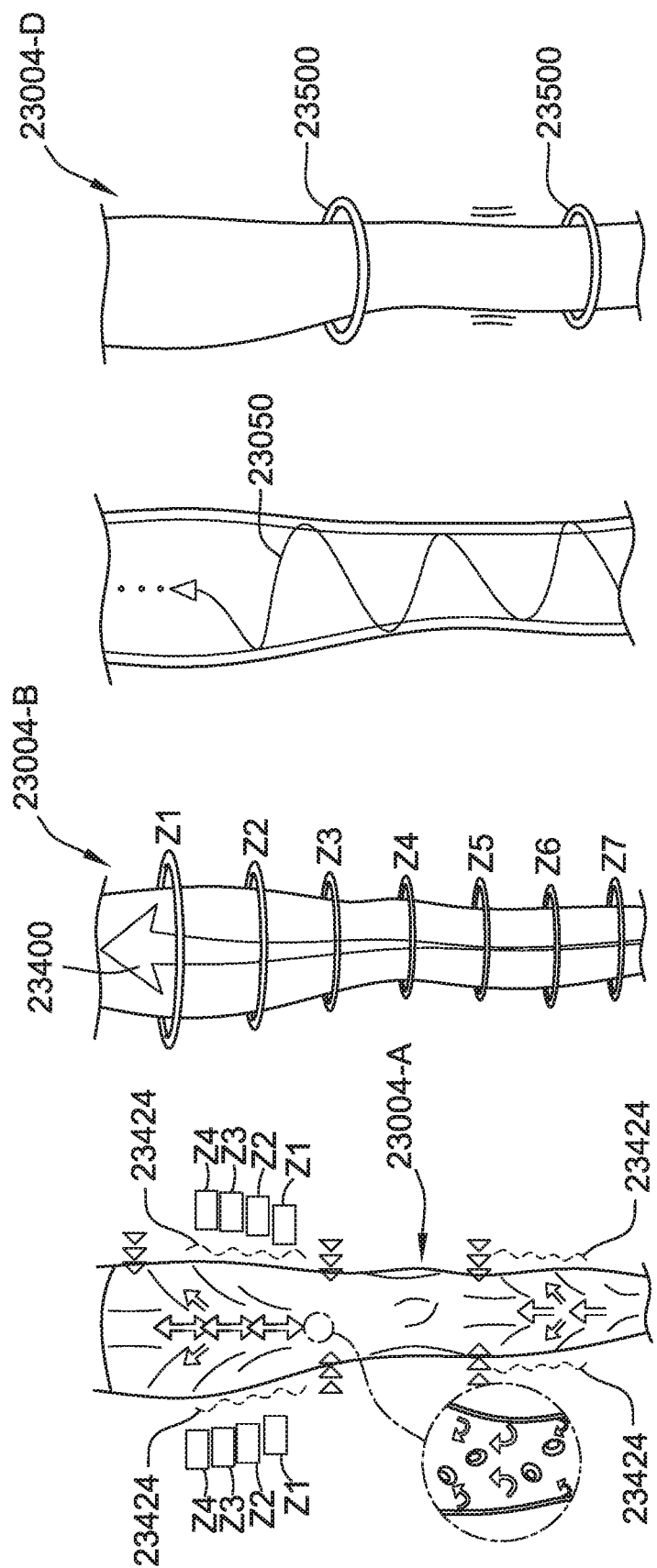
FIG. 23A illustrates leg compression garment configurations and operations, according to some implementations of the present disclosure.
FIG. 23B illustrates leg compression garment configurations and operations, according to some implementations of the present disclosure.
FIG. 23C illustrates leg compression garment configurations and operations, according to some implementations of the present disclosure.
FIG. 23D illustrates leg compression garment configurations and operations, according to some implementations of the present disclosure.

In some versions, the compression garment, such as at its inner surface, may include, or form, one or more applicator(s). Such applicator(s) may be in contact (directly or indirectly) with the user's skin. Such applicator(s) may be a flexible rigid structure (e.g., a ridge(s), rib(s) or bump(s)) that may extend along the length of, or portions of, the compression garment. Such a rigid structure will typically be more rigid than a user's skin. Such a structure(s) can provide a more focused manipulative force when mechanically pressed into the user's skin by the inflation of one or more particular pneumatic chambers of the compression garment that reside next to or above where the applicator is located. Some versions of the applicator have a curving or wavy configuration along the length of the applicator. It may have a contact surface profile that includes hills and valleys relative to the user's skin. It may have a contact surface profile that snakes or curves along the length of the user's limb at the contact surface of the user's skin (such as without hills and/or valleys relative to the skin surface). An applicator, or a series of applicators, may extend over several pneumatic chambers (e.g., two or more, such as three, four, five, six, etc.) of the compression garment. Thus, a sequential activation of the pneumatic chambers can urge the applicator to apply an advancing manipulative force, at the skin-applicator contact area, that advances the manipulative force in a direction of the sequential activation of the pneumatic chambers and along the profile or shape (e.g., curved) of the applicator. An example of such an applicator 23424 is illustrated in FIG. 23A and the operation of which is discussed in more detail herein.

In some implementations, the compression garments of the present disclosure include air chambers with micro holes (perforations), which allows air to be diffused out at a controlled rate to provide a cooling and drying effect on the skin.

In some implementations, the compression garments of the present disclosure include an open or perforated conduit along the inner layer, such that air flow from the CPG device 1002 can be directed through this conduit with the aim of providing a cooling and drying impact on the skin.

6.5 Micro-Pumped System

An alternative implementation of the system 1000 has micro-pumps embedded into the air chambers enclosed within the garment 1004. When electrically activated by the CPG device 1002 via control lines in the link 1006, the micro-pumps fill the chambers with air and compress the limb. In such an implementation the link 1006 needs no pneumatic conduit between the CPG device 1002 and the garment 1004.

6.6 Non-Pneumatic Systems

In alternative implementations, a compression therapy system may be driven by non-pneumatic methods and/or a hybrid of non-pneumatic and pneumatic methods. The main advantage of such implementations is a high resolution on where the compression is applied, without the need for valves and pneumatic blocks. Some examples of non-pneumatic systems are given below.

6.6.1 Hydraulic/Electroactive Polymer Hybrid device

Figure 55:
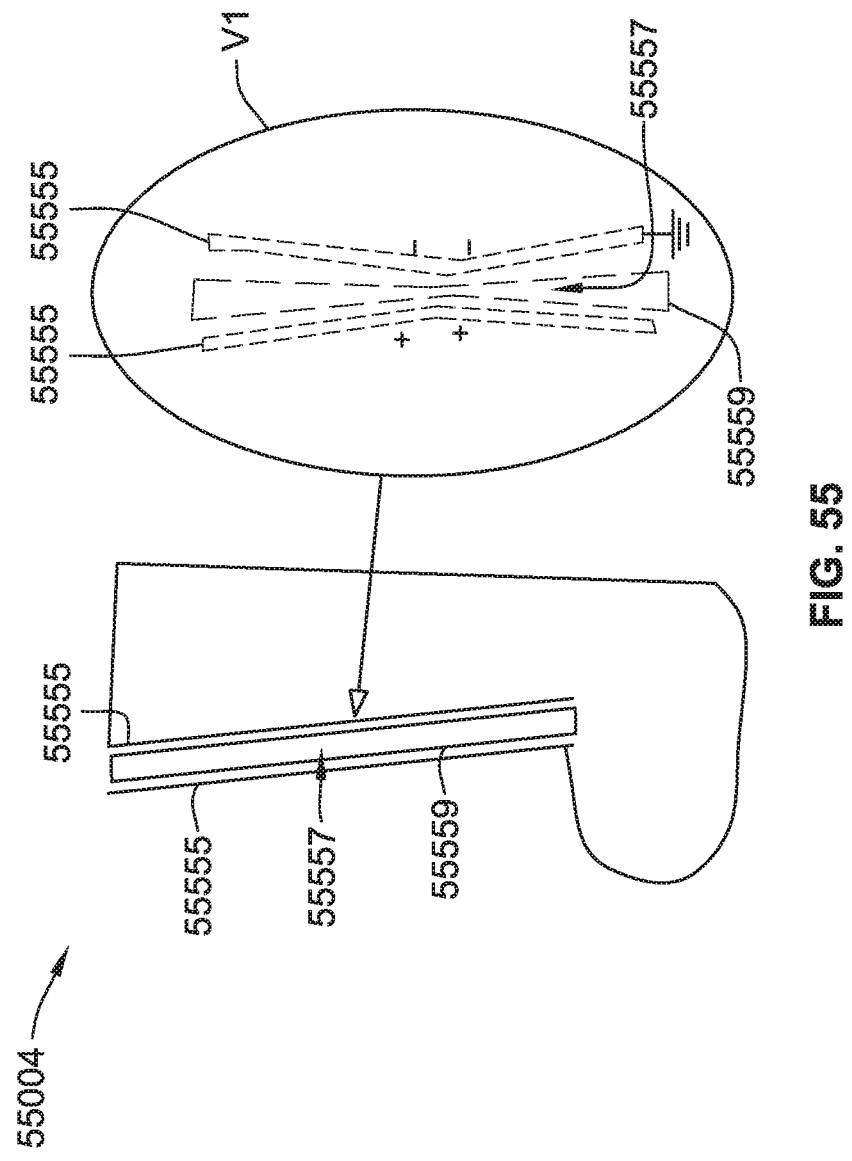
FIG. 55 is a schematic illustration of a Hydraulic/Electroactive Polymer Hybrid compression garment, according to some implementations of the present disclosure.

Referring to FIG. 55, a Hydraulic/Electroactive Polymer Hybrid compression garment 55004 is shown. The Hydraulic/Electroactive Polymer Hybrid garment 55004 comprises a fluid 55557 (water, gel etc.), such as in an elastomeric shell 55559, enclosed within and/or between two layers of electroactive polymer. The layers of electroactive polymer form electrodes 55555. Electroactive polymers (EAPs) are a type of flexible, elastic polymers (elastomer) that change size or shape when stimulated by an electric field. As illustrated in exploded view V1 in FIG. 55, two arrays of EAPs of the electrodes 55555 enclose a viscous fluid. When electric forces (voltage differences) are applied by a CPG to opposed sections of the respective arrays, the elastomer changes shape and displaces the viscous fluid to compress a corresponding segment of the limb.

6.6.2 Acoustic Device

Another non-pneumatic implementation of a compression therapy system comprises a garment enclosed with a viscous fluid and a speaker. Sound waves generated through the speaker can displace the fluid such that a smooth compression waveform is created (similar to a wave pool).

6.7 CPG Device Algorithms (Diagnostic and Therapy Control)

The central controller of the CPG device 1002 may be implemented with algorithms in processes or modules to implement the functions of a therapy, diagnostics, and/or monitoring device such for providing compression as part of a therapy or a diagnostics procedure with one or more of the compression garments. Such methodologies of the controller may implement Lymphedema therapy and/or Lymphedema monitoring. Any one or more of the following example process modules may be included.

6.7.1 Diagnostics Sensing/Monitoring Module(s)

Using the data from any of the sensors previously described, and optionally other user input from the control device, the central controller may be configured, such as with one or more detection or sensing module(s), to determine characteristics related to Lymphedema condition. For example, the controller may detect pneumatic impedance, pneumatic resistance, skin/body composition (e.g., fluid versus fat), skin density, skin temperature, skin impedance, compression garment related volume (limb volume) and compression garment related strain (limb girth) in one or more monitoring sessions. Such measures may be determined and recorded over days, weeks, months, years, etc. As discussed in more detail herein, such determined characteristics may then serve as input to a therapy module to determine control parameters for setting and controlling a compression therapy session (e.g., type of therapy and settings of therapy). Such measures may also be communicated to a clinician and/or user via the control device and/or portal system for further evaluation.

6.7.1.1 Diagnostics Waveform (Pneumatic Impedance and/or Resistance)

In one example, the central controller may control operation of the blower of the CPG device in a sensing procedure for detection of swelling. The controller may also control operation(s) of one or more active valves when present such as to localize the diagnostic to a particular zone of the compression garment. In such a process, the controller may generate a compression waveform (pneumatic) by operating the motor of the blower to pneumatically inflate one or more pneumatic chambers of the garment. Such a waveform may be a pressure waveform or a flow rate waveform that varies over a testing time period, such as the waveform 23050 illustrated in FIG. 23C. For example, a controlled pressure waveform may be sinusoidal (e.g., a sine wave of a predetermined frequency and amplitude). Alternatively, a controlled flow rate waveform may be sinusoidal (e.g., a sine wave of a predetermined frequency and amplitude). Other waveform functions of frequency and amplitude may also be implemented (e.g., square wave, cosine wave, etc.) Such waveforms may be achieved by flow rate control or pressure control such as with any suitable closed loop control operation.

During, or immediately after, generation of such a waveform within a predetermined testing period, the controller may measure pneumatic pressure and/or flow rate over time with the sensors of the system. The system may use at least one set frequency, but optionally could use a range of frequencies. A typical frequency range may be 0.1 Hz to 20 Hz. The sensors sense the pneumatic characteristics of the air supplied to and/or received from the compression garment such as the compression garment's response to the generated waveform. Thus, these pneumatic characteristics concern the pressure garment and the condition of the user's limb within the garment. Discrete values for measured pressure and measured flow rate at a given instant in time may be evaluated, such as to determine a pneumatic impedance or pneumatic resistance from the pressure and flow rate values. For example, resistance may be determined by dividing instantaneous pressure by instantaneous flow rate. Impedance may be similarly determined along with considering phase difference between the pressure and flow rate. The impedance and/or resistance over the predetermined time period of the pneumatic test may then provide a signal that may be useful for assessing a swelling condition of the user's limb within the compression garment. Moreover, if the testing process has been localized to a particular zone of the garment, such as by activating for example, valves to pressurize a lower portion of a compression garment, then the resulting signal concerns a particular portion of the user's limb. For example, if a compression garment has three zones (e.g., lower, middle and upper) that may be isolated by the controller setting the actives valves of the compression garment accordingly, the controller may conduct three testing processes to assess swelling in each zone (by determining the resistance or impedance signal). The determined signal(s) may be evaluated from multiple sessions to detect changes in swelling condition of the user. For example, the CPG device 1002 may be configured to perform such a diagnostic assessment of the particular zone(s) of a compression garment on a daily basis or each time the compression garment is used or several times during compression garment use. With such a signal(s), a display can provide information to a user (via a display such as of the CPG device 1002, control device or portal system) showing an amount of swelling as represented, or as a function of, the impedance or resistance information as well as the localized areas of the swelling. For example, minor, average, or significant levels of swelling may be associated with various ranges of values of impedance or resistance. By assessing whether a determined value is in a particular range or has a particular value (such as by comparison with one or more thresholds), the associated level of swelling may be identified.

In some versions, an average from the signal (e.g., average resistance) may be recorded. The controller may be configured to evaluate such a value (or other value of resistance or impedance) over time to detect changes. For example, an increase in the signal (or value therefrom) over multiple sessions (such as determined by a comparison of a current value with a previous value or other such threshold), may be taken as an indication of an increase in swelling and a problem with the patient's condition. Such a comparison may trigger, in the controller, a warning to the user or clinician. In some versions, such a comparison may serve as a basis for the controller to increase or change a compression therapy parameter (e.g., higher pressure, a different therapy protocol, or a longer therapy). In this way the controller may implement a compression therapy that is adaptive to changing patient conditions. By way of further example, a decrease in the signal (or value therefrom) over multiple sessions (such as determined by a comparison of a current value with a previous value or other such threshold), may be taken as an indication of a decrease in swelling and an improvement with the patient's condition. Such a comparison may trigger, in the controller, an update or warning to the user or clinician. In some versions, such a comparison may serve as a basis for the controller to decrease or change a compression therapy parameter (e.g., decrease pressure, a different therapy protocol, or a shorter therapy).

In some such versions, the diagnostic process may be performed before providing a compression therapy session, during and/or after providing the compression therapy session. A change in the determined impedance or resistance from before and after, or within, the session, such as a decrease or increase, may be taken, respectively, as an indication that no further compression therapy is necessary or that additional compression therapy is necessary. Thus, the controller may apply the diagnostic periodically during a therapy session to assess when the therapy can be discontinued. The controller may continue therapy if an evaluation of the determined resistance or impedance suggests that further therapy is needed. Alternatively, the controller may discontinue therapy if the evaluation of the determined resistance or impedance suggests that no further therapy is needed.

In some versions, an initial assessment of the determined resistance or impedance may be evaluated to determine the time (duration) or number of repetitions of therapy to be provided. For example, the determined resistance or impedance may be part of a function of the controller to assess therapy time (duration) or repetitions for a particular zone associated with the determined resistance or impedance, which may then serve as a control parameter for the controller to control the therapy for such a determined duration or number of cycles. For example, the function may indicate a shorter therapy time for a certain resistance or impedance associated with a lesser swelling. The function of the controller may indicate a longer therapy time for a certain resistance or impedance associated with a greater swelling. Similarly, in some versions, depending on the level of resistance or impedance, the controller may select a different therapy protocol from the different available therapy protocols provided by the CPG device or repeat a therapy protocol cycle.

In some versions, the pneumatic related impedance or resistance measurement may serve in a function of the controller to derive a girth or volume estimate of the patient's limb. For example, with a known dimension (e.g., volume) of a compression garment (e.g., a cylindrical sleeve) or a zone thereof, the pneumatic related impedance or resistance measurement may provide a proportional indication of how the patient's swelling limb is occupying the volume of the compression garment, or portions of the compression garment on a zone by zone basis. For example, a level of resistance or impedance may serve to functionally scale the known volume of the compression garment. For example, a higher level of resistance or impedance may be taken as a higher level of occupation of the known volume and a lower level of resistance or impedance may be taken as a lower level of occupation of the known volume. Such a relationship may be derived empirically and be adjusted on a garment-by-garment basis. Thus, with the measured resistance or impedance, such as on a zone by zone basis in the compression garment, the controller may provide a girth or volume estimate (e.g., on a zone by zone basis) as an output measure for different portions of a limb, such as on a display of the CPG device 1002, control device or portal system, that can inform the user or clinician, of the nature of the patient's Lymphedema condition, and progression of the Lymphedema condition when determined over a number of sessions or even a given session. Optionally, such a functional determination of volume or girth may also or alternatively be implemented by the controller with a measurement(s) from a tension or strain gauge or other similar strain sensor when the compression garment includes such sensor(s).

6.7.1.2 Diagnostics Waveform (Bioimpedance)

Although the aforementioned processes by the controller are based on a determination and/or assessment of pneumatic impedance or resistance from pneumatic sensing, the controller may alternatively, or in addition thereto, evaluate the patient's condition, and may additionally respond with therapeutic changes and/or information messages, by assessment of skin or body composition such as by measurements from a set of electrodes 23500 of a compression garment 23004-D as shown in FIG. 23D. Such responses of the controller may be similar to the processes previously described. For example, by measuring and evaluating skin impedance (electrical bioimpedance that may depend on body/skin composition) using the electrodes 23500, the controller may determine a measure indicating condition of a user's Lymphedema. For example, such measurements may vary depending on the nature of fluid retention in a limb zone of the compression garment. Thus, such measurements may serve as a marker of disease progression, such as an indication of tissue fibrosis, hardening and fluid retention.

Thus, the controller may have a control module for such a process to make such measurements to provide an indication of swelling. For example, electrical impedance of a particular part of a body may be estimated by measuring the voltage signal developed across a body part by applying a current signal (e.g., a low amplitude low frequency alternating current which may be sinusoidal or pulsed) to the body part via a set of electrodes (e.g., two or more of the compression garment). The impedance may be measured by dividing the measured voltage signal (V) by the applied current signal (I). Impedance (Z) can be a complex quantity and it may have a particular phase angle depending on the tissue properties. Thus, evaluation of the impedance (e.g., magnitude and/or phase angle) may involve the controller comparing measured impedance to one or more thresholds for detection of condition of the skin/body composition in relation to the potential for swelling. Such measurements may be made periodically and provide, through their evaluation by the controller (e.g., threshold comparison(s)), a diagnostic parameter for the controller to generate information characterizing the nature of swelling (e.g., high, medium or low) or Lymphedema (e.g., displayed information and warnings) and/or to control therapy changes. Thus, such an evaluation (e.g., an indication of increased fluid content or swelling) may serve as a basis for the controller to increase or change a compression therapy parameter (e.g., higher pressure, a different therapy protocol, or a longer therapy). Similarly, such an evaluation (e.g., an indication of decreased fluid content or swelling) may serve as a basis for the controller to decrease or change a compression therapy parameter (e.g., lower pressure, a different therapy protocol, or a shorter therapy). Such a process may be similar to the process previously described in relation to the assessment of pneumatic impedance/resistance.

For example, the controller may be configured to evaluate such an impedance value (or values) over time to detect changes. For example, an increase in the values over multiple sessions (such as determined by a comparison of a current value with a previous value or other such threshold), may be taken as an indication of an increase in swelling and a problem with the patient's condition. Such a comparison may trigger, in the controller, a warning to the user or clinician. In some versions, such a comparison may serve as a basis for the controller to change or increase a compression therapy parameter (e.g., higher pressure, a different therapy protocol, or a longer therapy). Similarly, a decrease in the values over multiple sessions (such as determined by a comparison of a current value with a previous value or other such threshold), may be taken as an indication of a decrease in swelling and an improvement with the patient's condition. Such a comparison may trigger, in the controller, an update or warning to the user or clinician. In some versions, such a comparison may serve as a basis for the controller to change or decrease a compression therapy parameter (e.g., lower pressure, a different therapy protocol, or a shorter therapy).

In some such versions, the diagnostic process may be performed before providing a compression therapy session during and/or after providing the compression therapy session. A change in the determined impedance from before, during and/or after the session, such as a reduction or increase, may be taken respectively as an indication that no further compression therapy is necessary or that additional compression therapy is necessary. Thus, the controller may apply the diagnostic periodically during a therapy session to assess when the therapy can be discontinued. The controller may continue therapy (e.g., repeat a cycle of therapy) if an evaluation of the determined impedance suggests that further therapy is needed. Alternatively, the controller may discontinue therapy if the evaluation of the determined impedance suggests that no further therapy is needed.

In some versions, an initial assessment of the determined impedance may be evaluated to determine the time (duration) of therapy or number of cycles to be provided. For example, the determined impedance may be part of a function of the controller to assess therapy time for a particular zone associated with the determined impedance, which may then serve as a control parameter for the controller to control the therapy for such a determined duration or a number of cycles that may achieve the therapy time. For example, the function may indicate a shorter therapy time or fewer cycles for a certain impedance associated with a less swelling. The function of the controller may indicate a longer therapy time or more cycles for a certain impedance associated with a greater swelling. Similarly, in some versions, depending on the level of impedance, the controller may select a different therapy protocol from the different available therapy protocols provided by the CPG device 1002 or repeat a therapy protocol cycle.

6.7.1.3 Diagnostics (Temperature)

The CPG device 1002 and/or any of the compression garments of the present disclosure may include one or more temperature sensors. One or more measurements from any of such temperature sensors may inform the controller about the Lymphedema condition of a user. Thus, the controller may be configured to evaluate temperature measure(s), such as in comparison to one or more thresholds, in providing information to the user or clinician, via a monitor of the CPG device 1002, the control device, and/or the portal system. Similarly, the controller may evaluate temperature measure(s), such as in comparison to one or more thresholds, for adjusting one or more therapy control parameters based on the determined temperature. For example, the controller may be configured to evaluate temperature associated with the condition of the user's skin from any of the sensor measures or zones of the compression garment. The controller, based on the evaluation, may be configured to suspend a therapy, reduce a therapy time, increase a therapy time, increase or reduce a therapy pressure, change a compression protocol or type of therapy, such as in the particular zone of the temperature measure or for all zones of the compression garment. For example, an increase or decrease in temperature (such as determined by comparison between one or more measurements from the temperature sensor and one or more thresholds) may be taken as an indication of a bacterial infection or elimination of a bacterial infection. Such a detection may trigger the controller to send a warning to the user or clinician. Such a detection may also trigger the controller to suspend or reduce a compression therapy, such as in the particular zone of detection, or initiate a compression therapy (e.g., of a lesser or higher than usual pressure in the zone of detection) or initiate a compression therapy so as to control the compression therapy in zones of the compression garment(s) that are not associated with the detected temperature increase or decrease. Other adjustments to the control of the compression therapy based on detected temperature may also be implemented by the controller.

6.7.1.4 Diagnostics (Limb Circumference)

As previously mentioned, the CPG device 1002 and/or any of the compression garments of the present disclosure may include one or more stretch sensors (e.g. dielectric elastomer sensors) and/or strain gauges. One or more measurements from any of such sensors may inform the controller about the limb circumference. Thus, the controller may be configured to evaluate limb circumference measure(s), such as in comparison to one or more thresholds, in providing information to the user or clinician, via a monitor of the CPG device 1002, the control device, and/or the portal system. Similarly, the controller may evaluate limb circumference measure(s), such as in comparison to one or more thresholds, for adjusting one or more therapy control parameters based on the determined circumference. For example, the controller may be configured to evaluate limb circumference from any of the sensor measures or zones of the compression garment. The controller, based on the evaluation, may be configured to suspend a therapy, reduce a therapy time, increase a therapy time, increase or reduce a therapy pressure, change a compression protocol or type of therapy, such as in the particular zone of the limb circumference measure or for all zones of the compression garment.

6.7.1.5 Diagnostics (Ultrasound)

One or more of the compression garments of the present disclosure may be configured with ultrasound transducers that are connected to the CPG device 1002 via electrical lines of the link 1006. One or more measurements from any such transducers may inform the controller about the Lymphedema condition of a user. Ultrasound sensing is capable of providing deep tissue information such as deeper lymphatic structures and how well fluid is draining.

6.7.2 Therapy Modes Module(s)

The controller of the CPG device 1002, such as central controller 4230, may be configured to select between different therapy operations modes depending on which compression garment(s) of the present disclosure is/are connected to the CPG device 1002 and/or based on the conditions detected by the sensor. Such modes may depend on the number of zones of active valves coupled to the system. Such mode selections may be implemented by the controller in conjunction with clinician or user input (e.g., manual settings of the user interface of the CPG device and/or control device and/or transmitted from a portal system) and measurements from the sensors as previously described. Example control parameters of the controller that may be adjusted include, for example, the type (protocol) of compression therapy, pressure setting parameters, pressure waveform parameters, valve activation parameters such as for activation of zones at different times, and therapy time parameters. Examples of types of compression therapy are describe in more detail herein.

6.7.2.1 Applicator Manipulation Therapy

In some versions, the CPG device 1002 may be configured with a control protocol for control of one or more compression garments to provide an applicator manipulation therapy. Such a Lymphedema therapy may be considered in relation to FIG. 23A. As illustrated, a compression garment 23004-A is configured with multiple zones Z1, Z2, Z3, Z4 (e.g., active valve and/or passive valve areas) that may be separately activated by the controller of the CPG device 1002 (electrically and/or pneumatically). These zones Z1, Z2, Z3, Z4 may include one or more applicator(s) 23424 as previously discussed. The compression garment 23004-A can include fewer or more such zones and fewer or more such applicators 23424.

To provide the applicator manipulation therapy, the controller may selectively activate the blower and/or valves to produce pressure compression (e.g., vibrations) in a desired directional manner so as to induce a desired movement of the applicator on the patient's skin with sequential pressurization of the pneumatic chambers. One example of applicator manipulation provides a massage therapy that emulates the manual massage performed by physical therapists on lymphedema patients. In such an example, the controller may set the motor of the blower so that the CPG device 1002 produces a positive pressure according to a pressure setting (e.g., a predetermined pressure or a pressure determined based on a previous evaluation of sensor data). The controller may then actively inflate a first zone (e.g., Z1) by activating its valve(s) (open) to direct the pressurized air to the pneumatic chamber(s) of the zone. Such a pressure may optionally be varied by the controller as a pressure waveform (e.g., sinusoidal or other) to induce a vibratory pressure inflation/deflation wave in the first zone. Such a pressure waveform may optionally be achieved by increasing and decreasing motor current of the blower and/or by opening and closing of the first zone active valve(s). This inflation/deflation permits the applicator to move to provide a localized force into the patient's skin responsive to the inflation/deflation. During this time, the controller may refrain from adjusting the active valves of other zones of the compression garment. Such control operations with the first zone may operate for a predetermined time (such as a fraction of the total desired therapy time.)

After the predetermined time, such a pressure control of the first zone may cease, such as by closing the active valves of the zone to maintain pressure in the zone or allowing the zone to deflate (e.g., partially to a second but lower positive pressure or completely to ambient pressure). The controller may then begin a similar pressurization routine with another zone, such as the next neighbouring zone (Z2) of the first zone. This may repeat the control as described with reference to the first zone but controlling the valves of the neighbouring zone over a second predetermined time, which may be approximately equal to the first predetermined time. In this manner, the controller may sequentially actuate the zones of the compression garment 23004-A in a predetermined order (e.g., first Z1, then Z2, then Z3, then Z4 etc.) Preferably, such an ordering of control by the controller of the different zones of the compression garment 23004-A provides a sequential progression applying the applicator along the limb of the patient toward the trunk of the patient as a therapy. Thus, the zones may be sequentially activated toward a trunk end (e.g., closer to the patient's trunk) of the compression garment (e.g., away from an extremity end (further from the patient's trunk) of the compression garment).

This process may be repeated by the controller so that the therapy may cycle through each of the zones any number of times. Such a number of repetitions may be set as a control parameter for the therapy such as by a manual input to the CPG device 1002. Optionally, such repetition of a cycle of the applicator manipulation therapy may be based on the controller determining the presence of a certain level of swelling such as with any of the previously described diagnostic processes. For example, any one or more of the resistance, impedance, bioimpedance, girth, volume, skin/body composition, etc. sensing measures may be determined and evaluated by the controller after a cycle of therapy and the evaluation may trigger a repeat of the cycle or a termination of the therapy session. Similarly, the controller may determine whether to adjust the applied compression pressure level(s), such as to be higher, lower or the same pressure settings depending on the evaluation of the sensor measurements. As previously mentioned, such repeated cycles may be controlled to be repeated for one, several or all of the zones of the garment depending on the measurement results of each zone.

Optionally, such a massage therapy protocol may be provided by the controller as described with a compression garment that does not include any applicator.

6.7.2.2 Gradient Therapy

In some versions, the CPG device 1002 may be configured with a control protocol for control of one or more compression garments to provide a gradient therapy such as by controlling the valves of multiple zones to provide a pressure compression gradient that may be static for a desired therapy time. Such a Lymphedema therapy may be considered in relation to FIG. 23B. As illustrated, a compression garment 23004-B is configured with multiple zones Z1, Z2, Z3, Z4, Z5, Z6, Z7 (e.g., active valve and/or passive valve areas) that can be separately activated by the controller of the CPG device 1002 (electrically and/or pneumatically). These zones Z1, Z2, Z3, Z4, Z5, Z6, Z7 may optionally include one or more applicator(s) as previously discussed. The compression garment 23004-B may have fewer or more such zones. In such an exemplary therapy protocol, the controller may be configured to set the pressure of the zones to different levels, such as a different level in each zone. Thus, the controller may be configured to set a first pressure in a first zone, a second pressure in a second zone, a third pressure in a third zone, etc. These set pressures may be different pressure levels (e.g., have a different positive pressure value $cmH_2O$ in some or all of the zones). Optionally, such pressures may be set so as to enforce a pressure compression gradient across a plurality of zones of a compression garment. For example, the third pressure may be greater than the second pressure, and the second pressure may be greater than the first pressure, etc. Optionally, such a gradient (increasing or decreasing) may be set in the compression garment 23004-B so that its increase or decrease extends along the length of the user's limb. Such an increase set by the controller over the different zones of the compression garment 23004-B can provide the gradient 23400 so that the pressure decreases along the limb of the patient toward the trunk of the patient or toward a trunk end of the compression garment 23004-B. Thus, the higher pressures may be in the lateral portion of the limb (further from the trunk) and the lower pressures may be in the medial portion of the limb (closer to the trunk). Alternatively, the controller may set such a gradient with a pressure decrease in the different zones of the compression garment 23004-B so that the pressure increases along the limb of the patient toward the trunk of the patient or the trunk end of the compression garment 23004-B.

In one example to provide the gradient therapy, the controller may be configured with a module or process that sets the zones to the gradient. For example, the controller may selectively activate the blower and/or valves to produce a pressure compression gradient by pressurization of the pneumatic chambers. In relation to the example compression garment illustrated in FIG. 23B, upon activation of the blower or CPG device 1002, the controller may initially control the blower motor, such as in a pressure control loop, at a first pressure setting. During this time, the controller may direct a flow of pressurized air to a first zone, such as first zone Z1, by controlling an opening of one or more active valves associated with the first zone Z1. When the measured pressure achieves the desired level associated with the first pressure setting, the controller may then control the one or more active valves associated with the first zone Z1 to close. This may permit the first pressure to be maintained in the pneumatic chamber(s) of the first zone Z1.

Next, the controller may control the blower motor, such as in a pressure control loop, at a second pressure setting that is higher than the first pressure setting. During this time, the controller may direct a flow of pressurized air to a second zone, such as second zone Z2, by controlling an opening of one or more active valves associated with the second zone Z2. When the measured pressure achieves the desired level associated with the second pressure setting, the controller may then control the one or more active valves associated with the second zone Z2 to close. This may permit the second pressure to be maintained in the pneumatic chamber(s) of the second zone Z2.

This process may be repeated to set the pressure in each succeeding zone (e.g., zone Z3 to zone Z7) to a higher pressure than the preceding zone, until the pressure is set in each zone according to the desired gradient. Optionally, the CPG device 1002 may be disengaged once the zones have been set at the desired pressure levels. The CPG device 1002 may then permit this pressure gradient therapy state to be maintained for a predetermined therapy time or some modified time in relation to the diagnostics process(es) as previously described that may optionally be engaged by the controller and the sensors to adjust the therapy time. Upon expiration of the therapy time as evaluated by an internal processing clock of the controller, the controller may then control the valves of all of the pressurized zones of the compression garment 23004-B to open to release the compression pressure in each of the zones Z1-Z7. Optionally, such a gradient therapy process may be repeated any desired number of times, with a predetermined period of rest (depressurization) between each pressurization cycle that achieves the desired gradient.

Thus, the gradient therapy cycle may be repeated by the controller so that the therapy may be provided any number of times for a therapy session. Such a number of repetitions may be set as a control parameter for the gradient therapy such as by a manual input to the CPG device 1002. Optionally, such repetition of a cycle of the gradient therapy may be based on the controller determining the presence of a certain level of swelling such as with any of the previously described diagnostic processes. For example, any one or more of the resistance, impedance, girth, volume, skin/body composition, etc. sensing measures may be determined and evaluated by the controller after a cycle of gradient therapy and the evaluation may trigger a repeat of the cycle or termination of the therapy session. Similarly, the controller may determine whether to adjust the applied compression pressure gradients (e.g., the high and low and intermediate steps, such as to be higher, lower or at the same pressure settings) depending on the evaluation of the sensor measurements. As previously mentioned, such repeated cycles, may be controlled to be repeated for several or all of the zones of the garment depending on the measurement results of each zone.

6.7.2.3 Adaptive Lymphatic Drainage therapy

In some versions, the CPG device 1002 may be configured with a control protocol for control of one or more compression garments in an Adaptive Lymphatic Drainage therapy mode. The Adaptive Lymphatic Drainage therapy mode includes two phases—a Lymph Unload Phase and a Clearance Phase—and is designed to emulate Manual Lymphatic Drainage therapy as performed by a therapist. The aim of the Lymph Unload Phase is to clear the proximal lymph vessels, such that fluid from the distal areas can be received and ultimately transported through to the circulatory system. To achieve this, the compression garment may comprise a number of sections, such as where each section may have one or more zones.

Figure 56A:
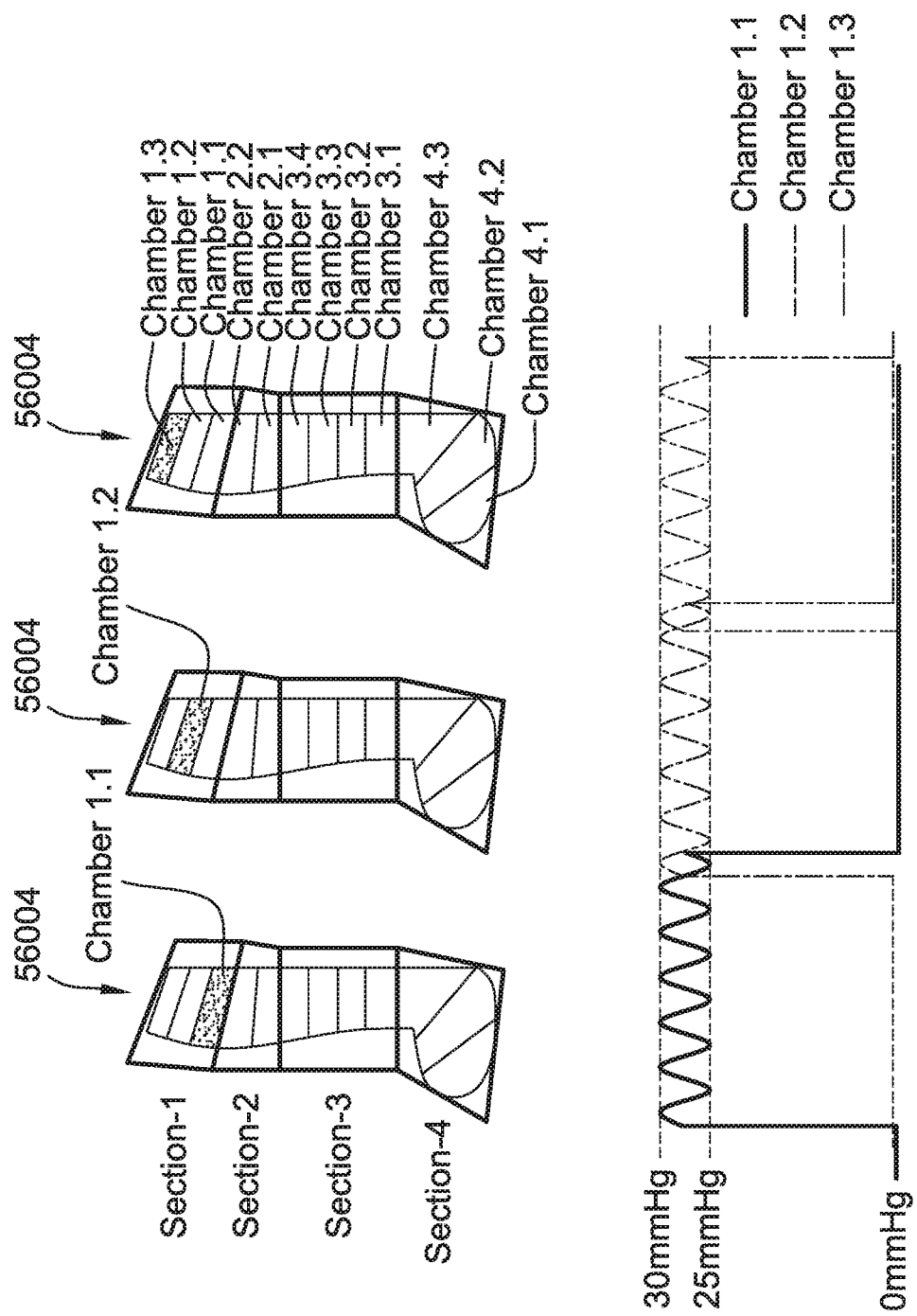
FIG. 56A is a schematic illustration of a compression garment with four discrete sections, with each section having a number of air chambers, and a first section of air chambers being activated, according to some implementations of the present disclosure.
Figure 56B:
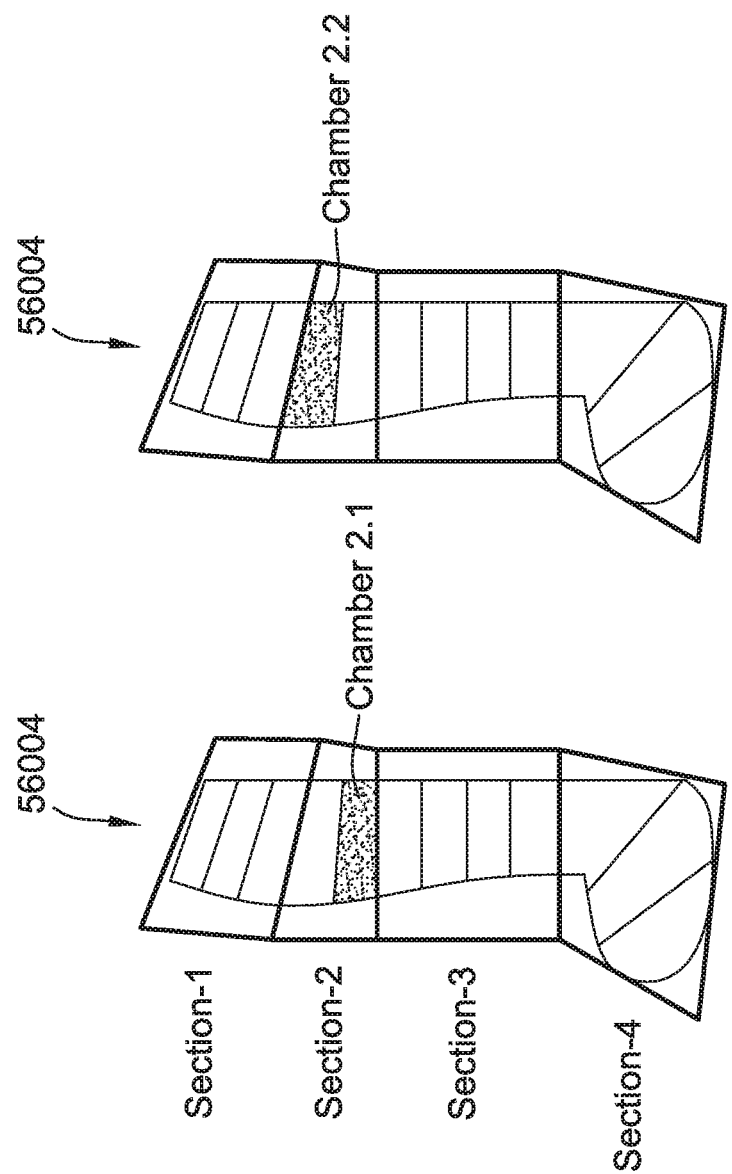
FIG. 56B is a schematic illustration of the compression garment of FIG. 56A having a different section of air chambers activated.

For example, referring to FIGS. 56A and 56B, a compression garment 56004 includes four discrete sections (zones), with each section comprising a grouping of air chambers. FIG. 56A illustrates activation of a one section (e.g., the first section) and FIG. 56B illustrates activation of another section (e.g., the second section). The Lymph Unload phase begins with the most proximal section (Section 1 in FIG. 56A), where an oscillatory compression waveform traverses through the chambers in the order illustrated. Chamber 1.1 will be pressurized first and then chamber 1.2 will follow. As chamber 1.2 is pressurized, chamber 1.1 will be deflated and chamber 1.3 will follow. Following Section 1, the same process is repeated on Section 2. An example oscillatory waveform being successively applied to chambers 1.1, 1.2, and 1.3 is illustrated in the bottom section of FIG. 56A. One aim of this oscillatory waveform is to maximise the level of stimulation provided to the lymph vessels, such that fluid transport can be encouraged. As illustrated, in this phase, control of each successive section advances (e.g., section-by-section) in a distal (e.g., downward) direction (e.g., section 1 to section 4), while control of each successive chamber within each section advances (e.g., chamber-by-chamber) in a proximal (e.g., upward) direction (e.g., chamber 1 to chamber 3). In such examples, a proximal direction may be a direction along a part of a user (e.g., limb) toward the user's heart and a distal direction may be a direction along a part of a user (e.g., limb) away from the user's heart.)

Following the Lymph Unload phase, the Clearance phase will begin, with the same waveforms being applied, this time progressing from pressurizing distal sections to pressurizing proximal sections. Thus, in this phase, control of each successive section advances (e.g., section-by-section) in a proximal (e.g., upward) direction (e.g., section 4 to section 1), while control of each successive chamber within each section advances (e.g., chamber-by-chamber) in a distal (e.g., downward) direction (e.g., chamber 3 to chamber 1). Table 1 provides an example control protocol of how this may occur.

TABLE 1

Order of pressurization of sections and chambers during Adaptive Lymphatic Drainage Therapy

| Time Point (Arbitrary) | Section Pressurized | Chamber Pressurized |
|---|---|---|
| Lymph Unload Phase | | |
| 1 | 1 | 1.1 |
| 2 | 1 | 1.2 |
| 3 | 1 | 1.3 |
| 4 | 2 | 2.1 |
| 5 | 2 | 2.2 |
| 6 | 3 | 3.1 |
| 7 | 3 | 3.2 |
| 8 | 3 | 3.3 |
| 9 | 3 | 3.4 |
| 10 | 4 | 4.1 |
| 11 | 4 | 4.2 |
| 12 | 4 | 4.3 |
| Clearance Phase | | |
| 13 | 4 | 4.3 |
| 14 | 4 | 4.2 |
| 15 | 4 | 4.1 |
| 16 | 3 | 3.4 |
| 17 | 3 | 3.3 |
| 18 | 3 | 3.2 |
| 19 | 3 | 3.1 |
| 20 | 2 | 2.2 |
| 21 | 2 | 2.1 |
| 22 | 1 | 1.3 |
| 23 | 1 | 1.2 |
| 24 | 1 | 1.1 |

The time spent pressurizing each section and chamber, and the number of cycles through each phase, may be determined in different ways. One method pressurizes each chamber for 10 seconds and repeats the Lymph Unload phase 5 times, before progressing to the Clearance phase. Alternatively, an adaptive and/or dynamic method receives diagnostic data on the limb condition (e.g., from sensors of the system), such as limb volume, limb girth etc., allowing the method to adapt the pressure response as well as the timing. For example, if after the Lymph Unload phase the sensor data suggests that limb volume has gone down sufficiently, the adaptive method could immediately move to the Clearance phase. Alternatively, the adaptive method could cycle through the Lymph Unload phase several more times before progressing to the Clearance phase. In this way, the adaptive method may adapt the level of pressure required and the time spent in each chamber, section, and phase of therapy depending on the patient condition.

6.7.2.4 Walk Mode

Often when patients have completed their massage therapy session and/or want to disconnect from the CPG device 1002, for example, in order to resume their daily routine, they require a degree of static compression in order to ensure that lymphatic fluid doesn't come back into the extracellular space. To achieve this, a walk mode therapy pre-inflates the compression garment to allow the patient to seamlessly continue with their routine without having to remove their compression garment and change to another, passive garment. The pre-inflate pressure(s) and/or pressure gradient may be predetermined or customizable as per the patient's needs as previously described.

6.7.3 Control Module

In some implementations of the present disclosure, the therapy device controller 4240 (shown in FIG. 5) receives as an input a target compression pressure Pt, such as per zone, and controls the therapy device 4245 (FIG. 5) to deliver that pressure in relation to a control of one or more active valves. The pressure may be delivered to all of the zones of the compression garment simultaneously or separately according to the timing of the operations of a valve control algorithm (e.g., diagnostic sensing or therapy control protocol) of the controller as described herein.

6.7.4 Detection of Fault Conditions

Optionally, in one form of the present technology, the central controller 4230 (FIG. 5) executes one or more methods for the detection of fault conditions. The fault conditions detected by the one or more methods may include at least one of the following:

Power failure (no power, or insufficient power)

Transducer fault detection

Failure to detect the presence of a compression garment component

Operating parameters outside recommended or plausible sensing ranges (e.g. pressure, flow, temperature)

Failure of a test alarm to generate a detectable alarm signal.

Upon detection of the fault condition, the corresponding algorithm signals the presence of the fault by one or more of the following:

Initiation of an audible, visual and/or kinetic (e.g. vibrating) alarm

Sending a message to an external device

Depressurizing the compression garment (e.g., opening the valves and/or vacuuming the pneumatic chambers).

Logging of the incident

According to another aspect of the present technology, the central controller 4230 omits a software module for detecting fault conditions. Rather, as discussed earlier, the detection of fault conditions may be handled exclusively by the fault mitigation integrated circuit that is separate from the central controller 4230. In some cases, the fault mitigation integrated circuit may serve as a redundant backup to similar fault detection/mitigation module with algorithms processed also within the central controller.

6.8 Control Device Application

The system 1000 may include a control device 1010 (FIG. 1) (e.g., a mobile phone or tablet computer) for running an application concerning operations with the CPG device 1002 and use of one or more compression garments of the present disclosure (e.g., compression garment 1004). Thus, the control device 1010 may include integrated chips, a memory and/or other control instruction, data or information storage medium for such an application. For example, programmed instructions or processor control instructions encompassing the operation methodologies of the control device described herein may be coded on integrated chips in the memory of the device or apparatus to form an application specific integrated chip (ASIC). Such instructions may also or alternatively be loaded as software or firmware using an appropriate data storage medium. Optionally, such processing instructions may be downloaded such as from a server over a network (e.g. the Internet) to the processing device such that when the instructions are executed, the processing device serves as a screening or monitoring device. Thus, the server of the network may also have the information storage medium with such instructions programmed instructions or processor control instructions and may be configured to receive requests for downloading and transmitting such instructions to the control device. In some versions, a portal system described herein may be such a server.

Example operations with such an application of the control device may be considered in reference to FIGS. 24 through 43. For example, as illustrated in FIG. 30, the control device 1010 may generate a pairing screen to wirelessly pair the control device for wireless communications with a CPG device and/or with sensors or other system components of a compression garment.

Figure 24:
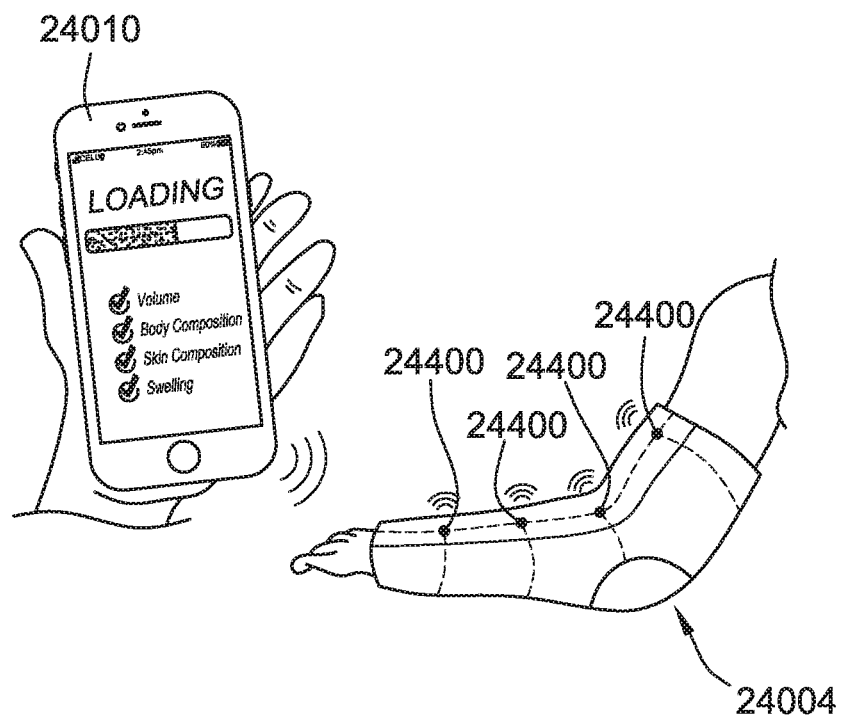
FIG. 24 is a perspective view of a control device configured to communicate (e.g., wirelessly) with sensors of an arm compression garment, according to some implementations of the present disclosure.

Referring to FIG. 24, a control device 24010 (the same as or similar to the control device 1010) may communicate (e.g., wirelessly) with one or more sensors of the system 1000 (FIG. 1), such as sensors 24400 of a compression garment 24004 or the CPG device 1002 (FIG. 1) to receive data. Such data includes pressure, body composition, skin health, girth, volume, swelling, impedance, resistance, temperature and/or bioimpedance, or any combination thereof, and such data may be displayed on the display of the control device 24010 and/or a display of the CPG device 1002.

Figure 26:
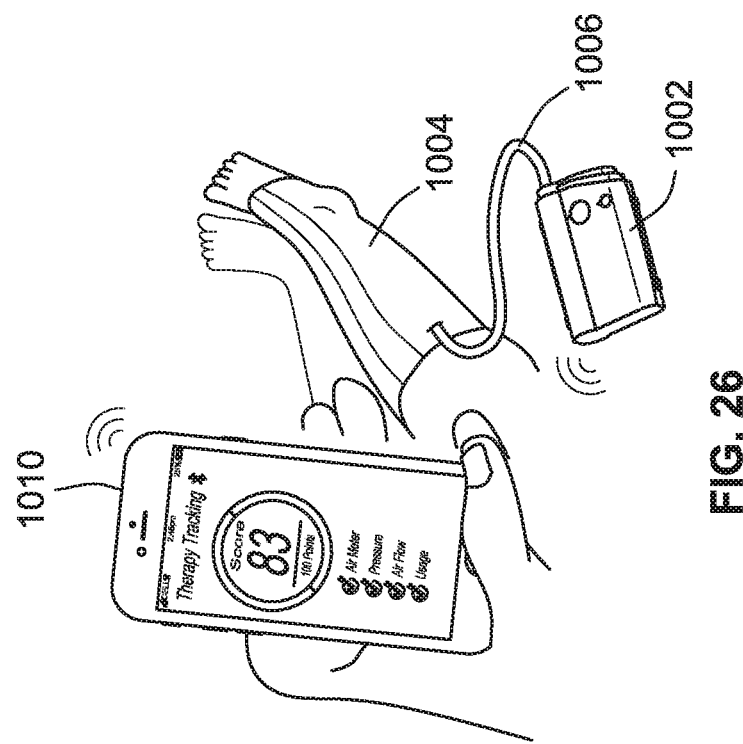
FIG. 26 is a perspective view of a compression therapy system including a control device configured to display information, according to some implementations of the present disclosure.
Figure 31:
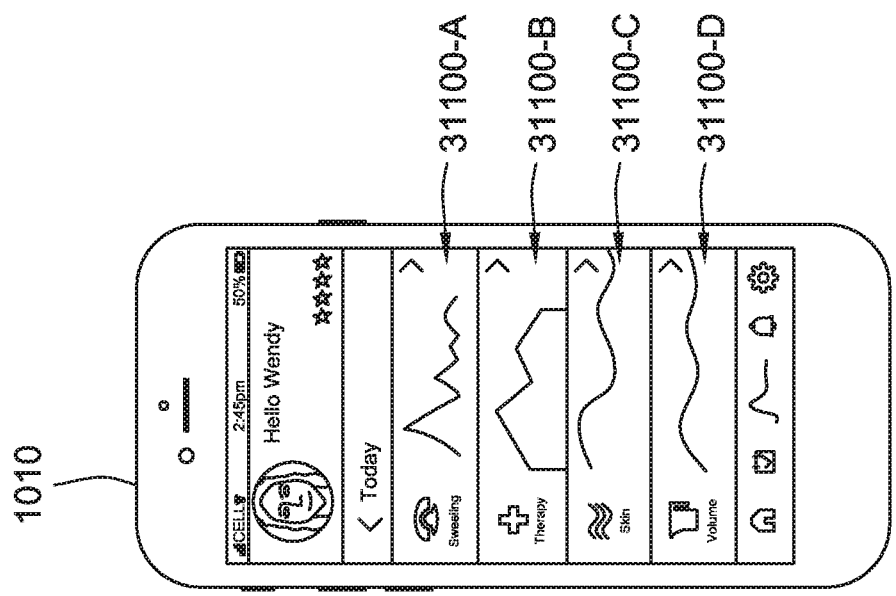
FIG. 31 is a perspective view of a control device configured to graphically illustrate data, according to some implementations of the present disclosure.

Referring to FIG. 26, data and/or information may be displayed for each session or it may be displayed as a trend over multiple days/sessions, weeks, months etc., of use of the compression garment 1004. The data may be evaluated over time for adjustments to therapy, such as to personalize the compression therapy (e.g., therapy time, number of cycles, pressure levels, etc.) which may be input to the CPG device 1002 via the control device 1010. The control device 1010 may also display usage information such as number of compression sessions, type of therapy, time of therapy, number of cycles. Such usage information which may also be presented in a trend or diary fashion over days, weeks, months, years, etc. Usage information may also be logged with a tagging interface illustrated in FIG. 39. Another display of such information is illustrated in the example of FIG. 36 which shows a compression therapy score 36500 that can represent an evaluation of the user's therapy to provide a combined indication of compression pressure and usage time and/or one or more other metrics. For example, as illustrated in FIG. 31, the user interface of the control device 1010 can graphically present a daily display with a graph of swelling versus time data 31100-A, a graph of therapy use versus time 31100-B, a graph of skin composition (e.g., density or fluid retention) versus time 31100-C, a graph of limb volume versus time 31100-D, or any combination thereof.

Figure 27:
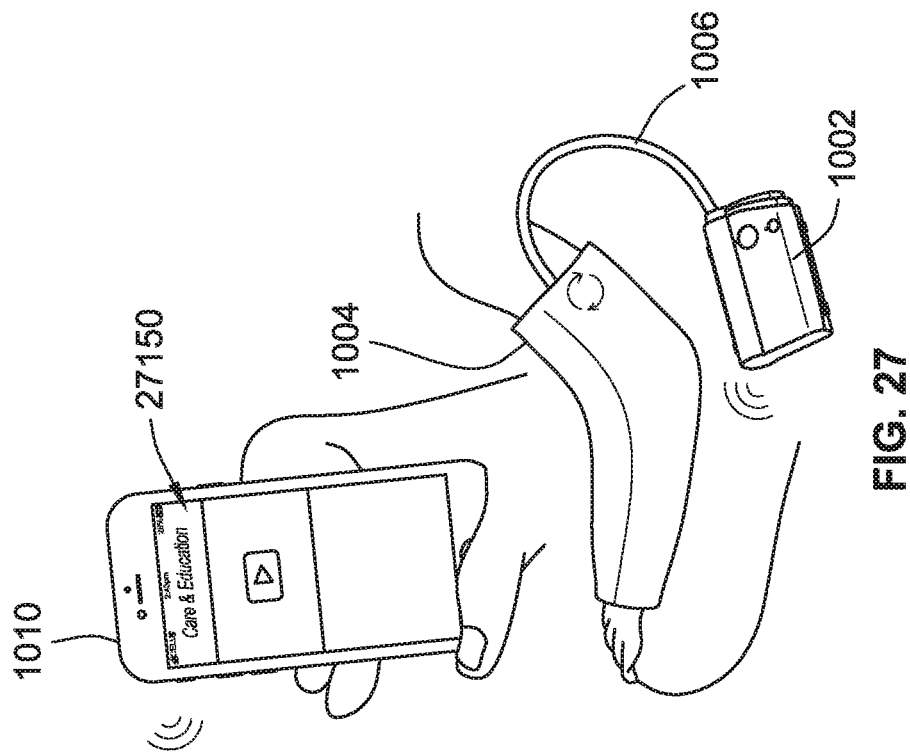
FIG. 27 is a perspective view of a compression therapy system including a control device configured to display instruction videos, according to some implementations of the present disclosure.
Figure 41:
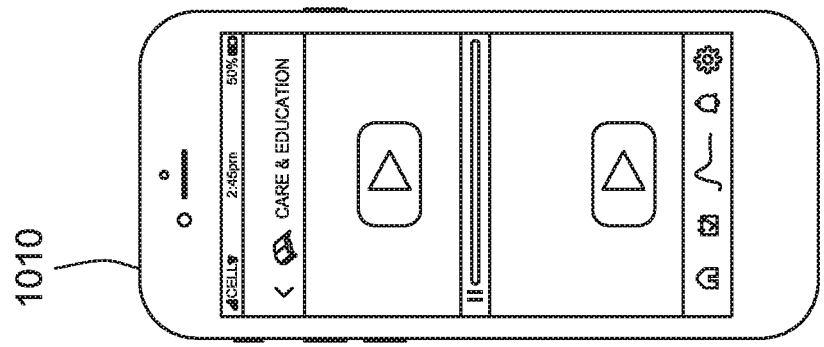
FIG. 41 is a plan view of a control device configured to permit a user to receive coaching and educational resources, according to some implementations of the present disclosure.

Referring to FIG. 27, the control device 1010 may present Lymphedema therapy and related health information 27150 to the user, such as instruction videos for use of the system 1000 with its compression garment 1004. Another version of such a user interface of the control device 1010 is illustrated in FIG. 41 such as for accessing and receiving coaching and education resources.

Figure 29:
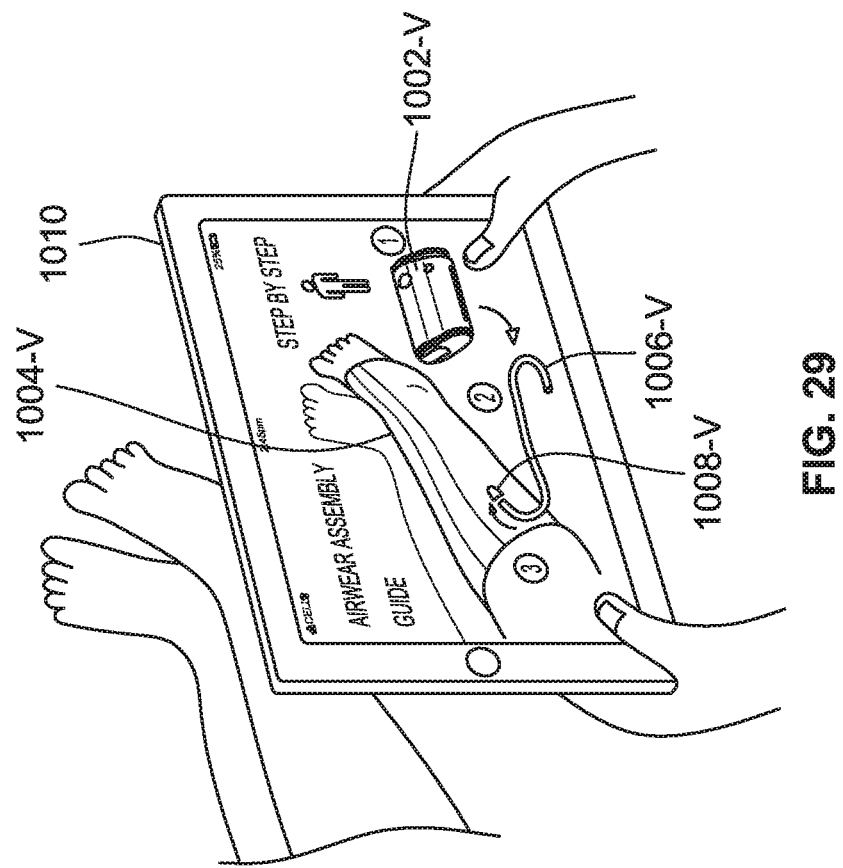
FIG. 29 is a perspective view of a control device configured to virtually illustrate one or more components of a compression therapy system, according to some implementations of the present disclosure.
Figure 30:
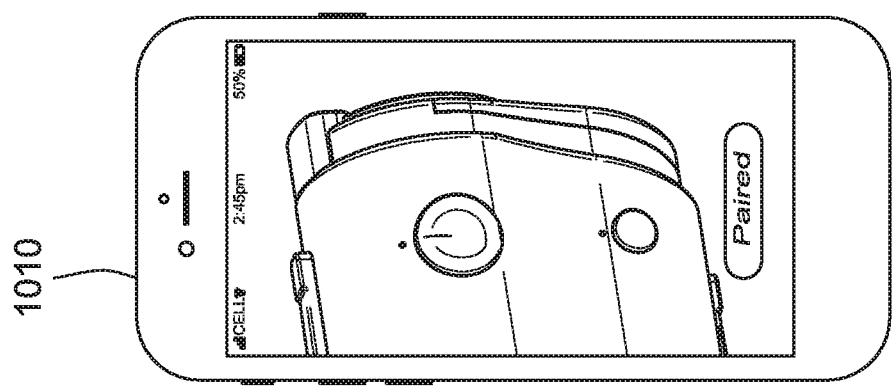
FIG. 30 is a perspective view of a control device configured to aid in wirelessly pairing components of a compression therapy system, according to some implementations of the present disclosure.

Referring to FIG. 29, a virtual presentation may be presented on the control device 1010. For example, the control device 1010 may present the user with a view of the compression garment 1004-V and show the pressure settings of each of the zones of the compression garment 1004-V as they change during a compression therapy session. Similarly, the control device 1010 may provide a virtual presentation on how to set up and use the CPG device 1002-V and/or the compression garment 1004-V with the link 1006-V and the interface 1008-V.

Figure 25:
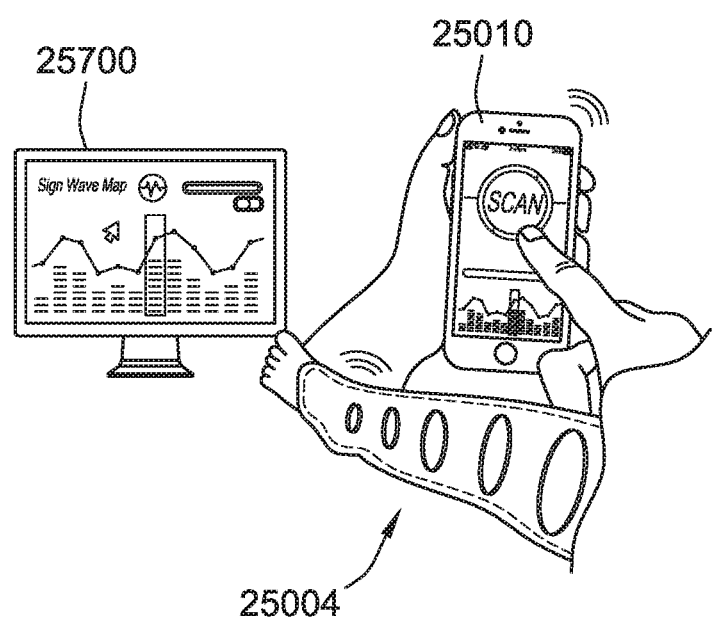
FIG. 25 is a perspective view of a control device configured to communicate (e.g., wirelessly) with a leg compression garment, according to some implementations of the present disclosure.

Referring to FIG. 25, the control device 25010 may generate periodic reminders (e.g., daily, weekly, monthly) to the user to use the compression garment 25004 for any of the diagnostic assessments described herein. For example, the control device 25010 may then provide a user control (e.g., button) on the user interface (e.g., display) of the control device 25010 that, when activated, initiates a process of the CPG device 1002 (FIG. 1) with the compression garment 25004 (such as via a wirelessly communicated control signal) to perform a diagnostic procedure such as the waveform assessments(s) previously described or any of the measurements previously described. The measurements may then be communicated to the control device 25010, which may then evaluate the measurement(s) such as in the processor of the control device 25010, so as to generate an assessment of the Lymphedema condition of the user. Optionally, such measurements and/or assessment may be communicated to a portal system 25700 described in more detail herein. The control device 25010 may then provide the user with evaluation information and instructions or warnings indicated by the evaluation of the Lymphedema condition. The control device 25010 may then prompt the user with a further user interface control (e.g., button) on the display to initiate a compression therapy session selected by the control device. Activation of the control on the control device 25010 by the user may then communicate a control signal (e.g., wireless) to the CPG device 1002 (FIG. 1) to start a compression therapy protocol controlled by the CPG device 1002, such as the any one or more of the protocols described herein.

Figure 28:
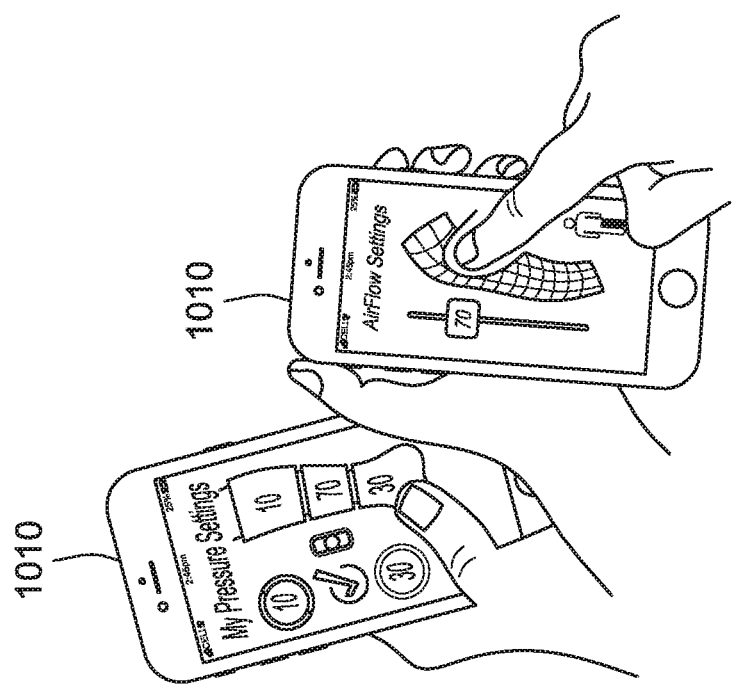
FIG. 28 is a perspective view of control devices configured to provide an interface for adjusting settings of a compression garment and/or CPG device, according to some implementations of the present disclosure.

Referring to FIG. 28, the control device 1010 may also provide a user interface so that a user can adjust the settings of the CPG device 1002 (FIG. 1) and a compression garment (e.g., 1004) for therapy. For example, the user can set pressure levels (e.g., maximum and minimum comfort levels), such as on a zone by zone basis or for all of the zones of a compression garment. The user can set therapy times and cycle repetitions. Such settings may then be communicated to the CPG device 1002 from the control device 1010. The CPG device 1002 may then provide therapy in accordance with the settings provided from the control device 1010.

Another example of such a user interface control is illustrated in FIG. 37 which provides a compression pressure slider control 37631 that may operate in conjunction with one of a group of zone selection buttons 37633 corresponding to the various zones of a compression garment 37004 to set a desired compression pressure level. In the example of FIG. 38, different pressure setting sliders 38631A, 38631B are presented for different zones 38004A, 38004B, respectively, of a compression garment 38004.

Figures 32, 33, 34, 35:
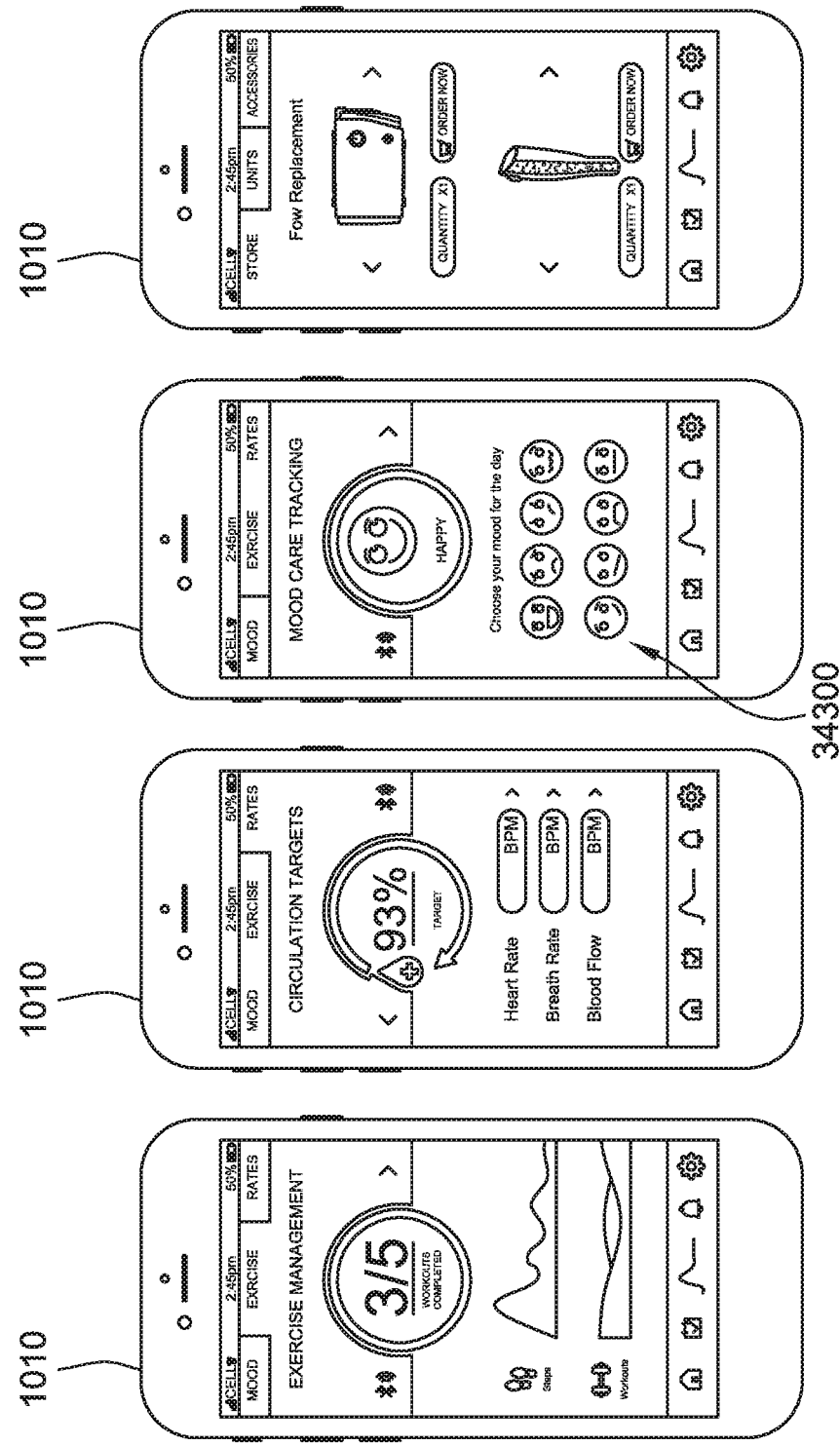
FIG. 32 is a plan view of a control device configured to graphically illustrate exercise information, according to some implementations of the present disclosure.
FIG. 33 is a plan view of a control device configured to graphically illustrate circulation information, according to some implementations of the present disclosure.
FIG. 34 is a plan view of a control device configured to aid in tracking moods of a user, according to some implementations of the present disclosure.
FIG. 35 is a plan view of a control device configured to aid a user in ordering components of a compression therapy system online, according to some implementations of the present disclosure.

Optionally, the control device 1010 may organize information in various additional user interface presentations such as illustrated in FIGS. 32, 33, and 34. For example as shown in FIG. 32, the control device 1010 may serve as a log of exercise information, such as steps taken on a daily basis, in relation to its correspondence with therapy session information, to show improved mobility progression with provided compression therapy. The compression therapy application of the control device 1010 may similarly track circulation information, such as illustrated in FIG. 33, including, for example, achievement of targets for heart rate, breath rate and/or blood flow information that may be derived from suitable sensors that may communicate with the system. As shown in FIG. 34, the control device 1010 may also serve as a mood tracker with a mood input user interface 34300 to log mood trends. FIG. 35 illustrates a user interface of the control device 1010 application that may serve as an online store/purchasing interface for remotely ordering or purchasing additional components for the compression therapy system.

Figure 43:
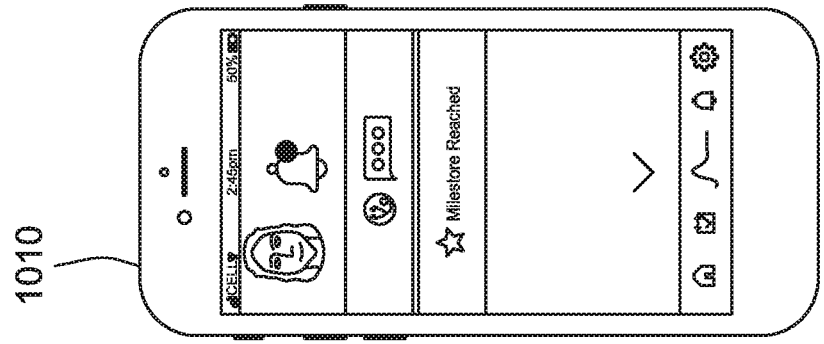
FIG. 43 is a plan view of a control device configured to provide a notification center, according to some implementations of the present disclosure.
Figure 42:
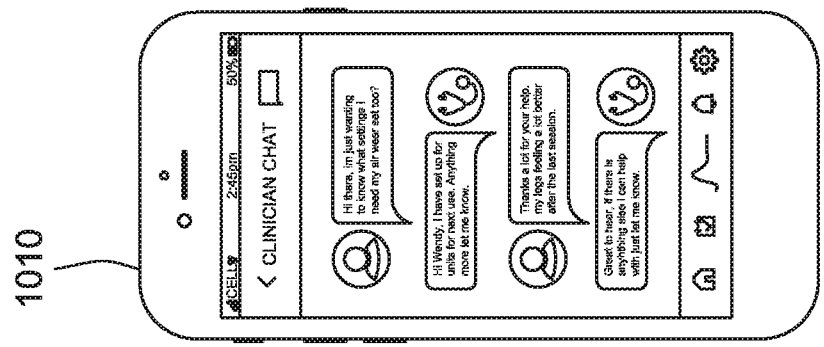
FIG. 42 is a plan view of a control device configured to permit direct-chat communication with professionals, according to some implementations of the present disclosure.
Figure 40:
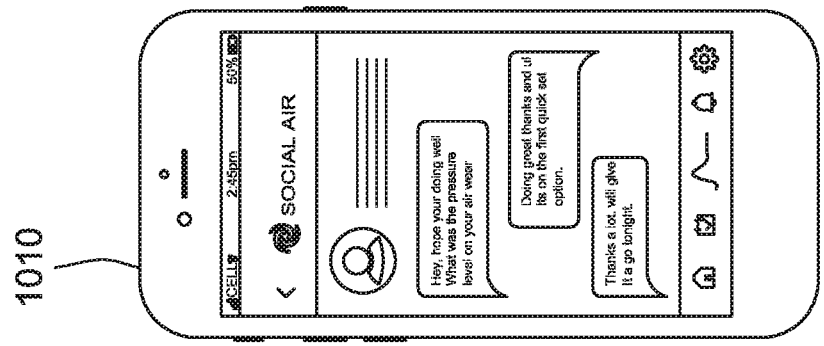
FIG. 40 is a plan view of a control device configured to permit communication with a community of user of compression therapy systems, according to some implementations of the present disclosure.

The application of the control device 1010 may also provide a communication function. Thus, the control device 1010 may present, such as illustrated in FIG. 40, a user interface for accessing and communicating with a community of users having a similar compression therapy system and Lymphedema condition such as for sharing information amongst peers. The control device 1010 may present a user interface for direct chat-based communications with Lymphedema clinical professionals as shown in FIG. 42. A notification center of the application, as shown in FIG. 43, can present status messages with information, such as goal achievement (e.g., use goals, mobility goals, etc.) messages as well update on chat conversations, etc.

6.9 Portal Management System

Figure 44:
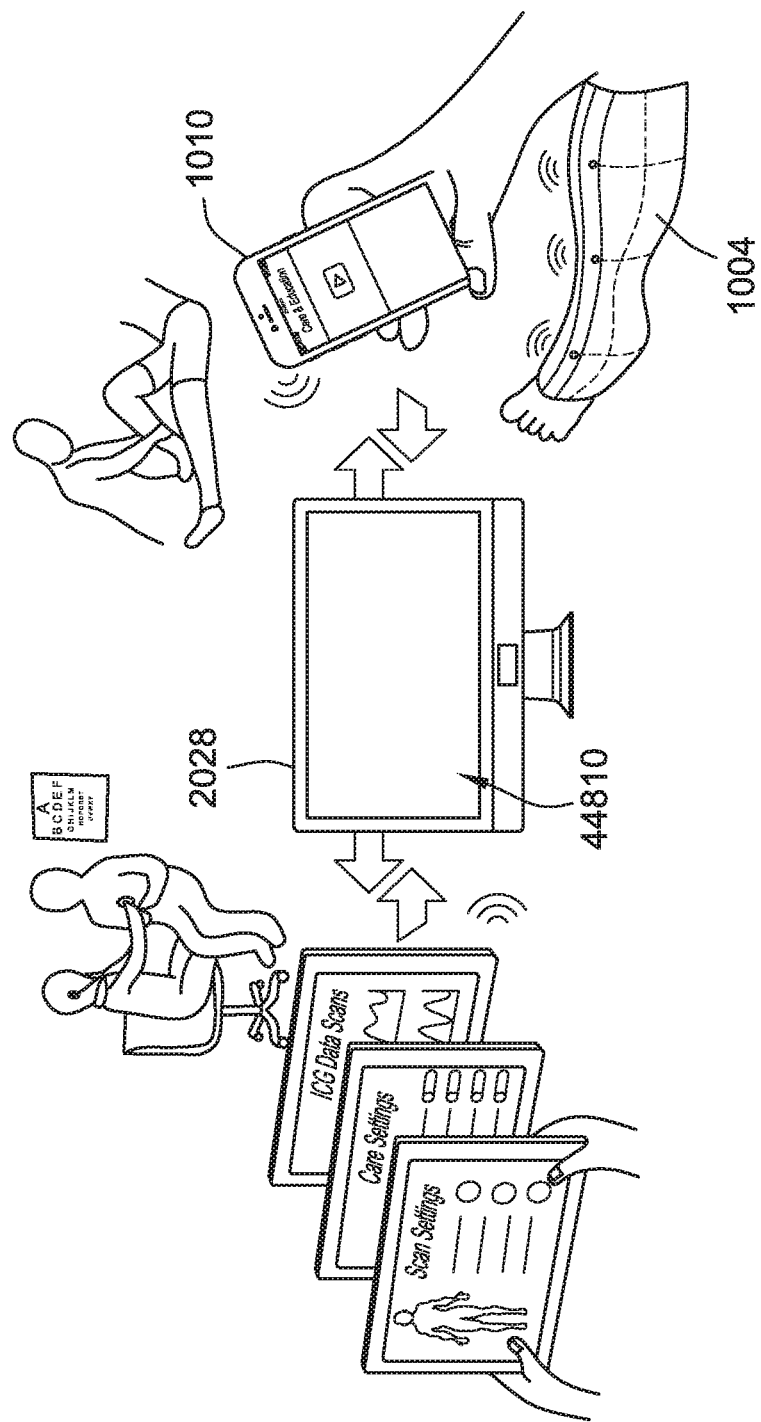
FIG. 44 is a perspective view of a portal system for managing a number of users of compression therapy systems, according to some implementations of the present disclosure.

A portal system 2028 (FIG. 2) may be implemented, such under the control of a clinician or provider, to manage a population of users of compression therapy systems. Configuration and operations of such a portal system 2028 may be considered in relation to FIGS. 44-54. Referring to FIG. 44, a clinician or other provider (e.g., health care provider) can serve multiple patients such as by screening patients by medical check-up and prescribing treatment with compression therapy systems 1000 (FIG. 1). For example, the provider may test a patient using a diagnostic process of a compression therapy system described herein and such data along with patient identification information may be uploaded to the portal system server application 44810. Clinical data and therapy information from continued use of the system 1000 by the patients can also be uploaded to the portal system 2028 as previously described. The clinician or provider, having access to the portal system 2028, can then use the portal to help customize care to the individual patient's needs via the portal system 2028. For example, body metrics (e.g., body composition, girth etc.) collected using the system 1000 can be transferred to the portal system 2028, which when combined with medical data of the patient, can drive the system 1000 to change settings and therapy parameters to customize the patient's therapy regimen such as by the automated application of the system 1000 and/or by the guidance of the provider or clinician. Notification of care changes can be made to the patient within the portal system 2028, which in turn can communicate with the control device(s) for changing settings of the CPG devices (e.g., CPG device 1002. In some examples, body metric data maintained by the system 1000 may include: body composition, skin density, skin composition, impedance, volume, girth, resistance, swelling, bioimpedance, temperature, etc., or any combination thereof.

Figure 45:
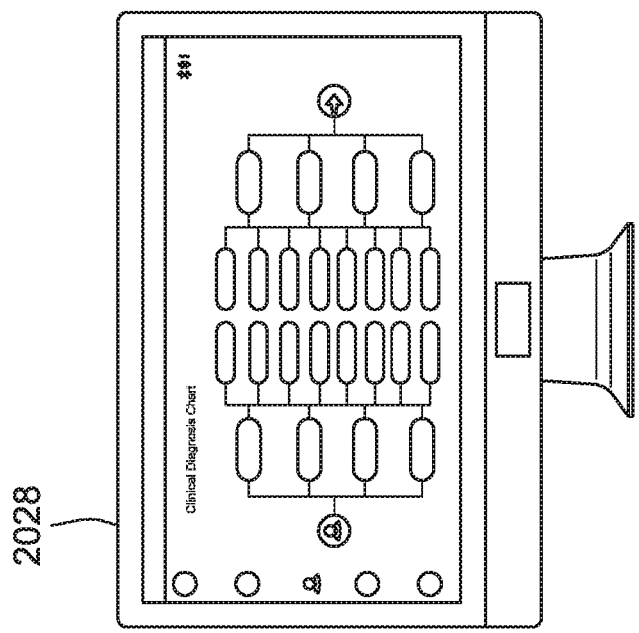
FIG. 45 is a front view of a portal system for aiding clinicians with a diagnosis, according to some implementations of the present disclosure.

Referring to FIG. 45, the portal system 2028 can provide clinicians with a diagnosis chart (e.g., on the portal system server application 44810) to aid in guiding the clinician in the selection of a system 1000 for the patient so that the patient user can be fitted into the correct compression garment system to suit their individual therapy needs (e.g., size and therapy protocol selection).

Figure 46:
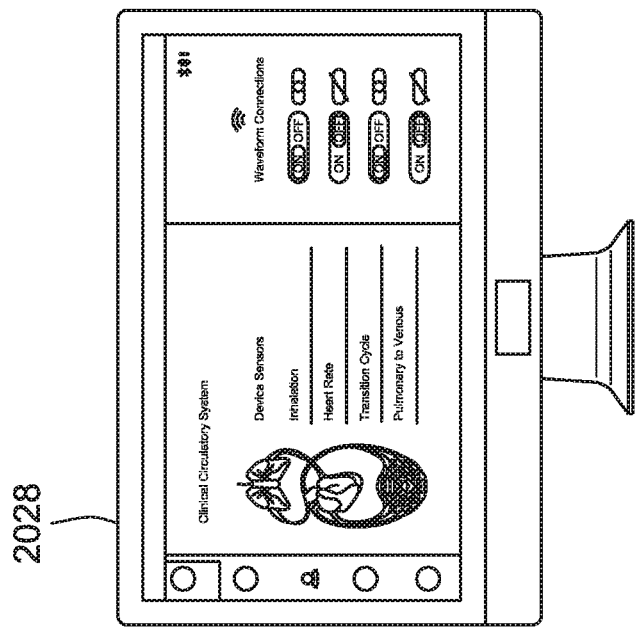
FIG. 46 is a front view of a portal system for aiding clinicians with monitoring circulation data for multiple users/patients, according to some implementations of the present disclosure.

Referring to FIG. 46, the portal system 2028 can provide a user interface for monitoring circulation and over-all circulatory data of multiple patients, such as on a patient by patient basis, to help the clinician/provider track blood flow and patient pathology, and to see how the compression garments and CPG devices are functioning to deliver treatment and improve patient condition.

Figure 47:
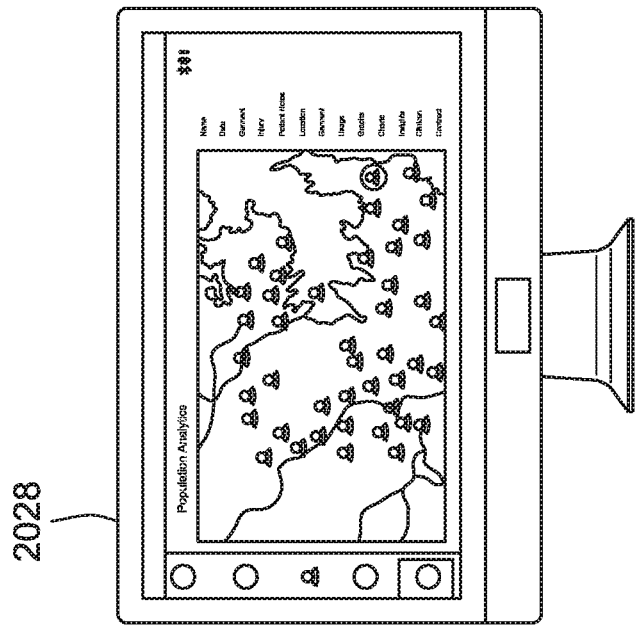
FIG. 47 is a front view of a portal system for monitoring and/or adjusting customized user settings for a plurality of user/patients of compression therapy systems, according to some implementations of the present disclosure.

Referring to FIG. 47, since each user's specifications will be unique to the user, the portal system 2028 can maintain, such as in a secured database system, customized set up information in relation to the user's particular physiology, dimensions, CPG device and compression garment information.

Figure 48:
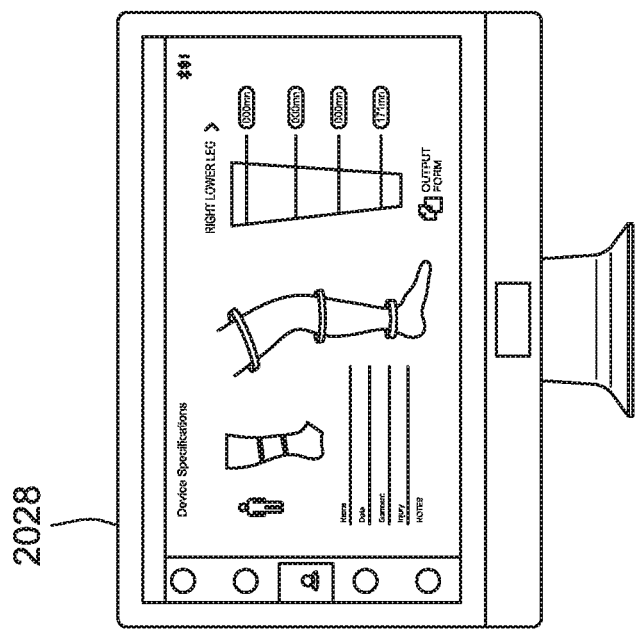
FIG. 48 is a front view of a portal system for providing analytics of a population of users/patients of compression therapy systems, according to some implementations of the present disclosure.

Referring to FIG. 48, the portal system 2028 can provide analytics for the population of users managed by the system. For example, the users can be monitored within the portal by categorizing each user according to similar injury or condition so that, with the categorization, the conditions can be tracked. Thus, medical benefits may be considered on a greater scale. Thus, the categorized data of the portal can serve as a basis for group evaluation to improve health outcomes.

Figure 49:
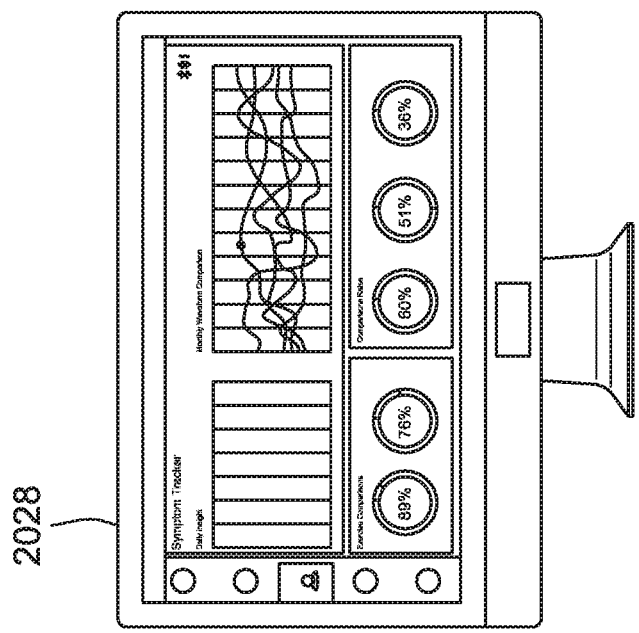
FIG. 49 is a front view of a portal system for aiding clinicians with symptom tracking of multiple users/patients, according to some implementations of the present disclosure.

Referring to FIG. 49, the portal system 2028 can present a user interface for symptom tracking. Thus, the clients' symptoms and therapy data can be tracked and stored so that the clinician or system can provide instructional help with the use of a CPG device (e.g., the CPG device 1002) and compression garment (e.g., compression garment 1004) usage, efficacy, and future product therapy improvement.

Figure 50:
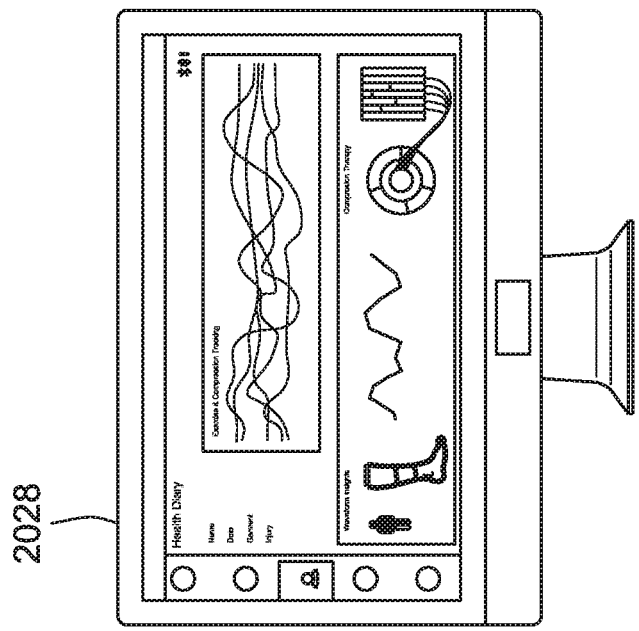
FIG. 50 is a front view of a portal system for providing clinicians with an overview of health data for multiple users/patients, according to some implementations of the present disclosure.

Similarly, as illustrated in FIG. 50, the portal system 2028 can present the clinician or provider with an overview of each client's health data from exercise through to device use, clinical history and therapy, which may be recorded within a health diary managed by the portal system. This can help clinicians deliver better connected health care.

Figure 51:
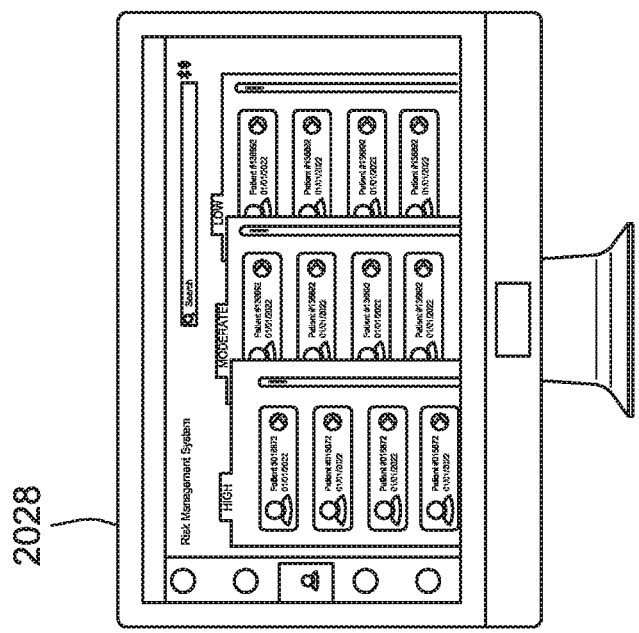
FIG. 51 is a front view of a portal system for aiding clinicians with risk management for multiple users/patients, according to some implementations of the present disclosure.

Referring to FIG. 51, the system 1000 can generate a management screen with actionable insights for managing Lymphedema patients with high to low risk priorities, such as based on an evaluation of data received by the portal system 2028. The system 1000 can also manage doctors' contact and consultations with users/patients according to the priorities, such as by generating messages to urge such contact and consultations. Such messages may be generated according to the system 1000 determined priorities.

Figure 52:
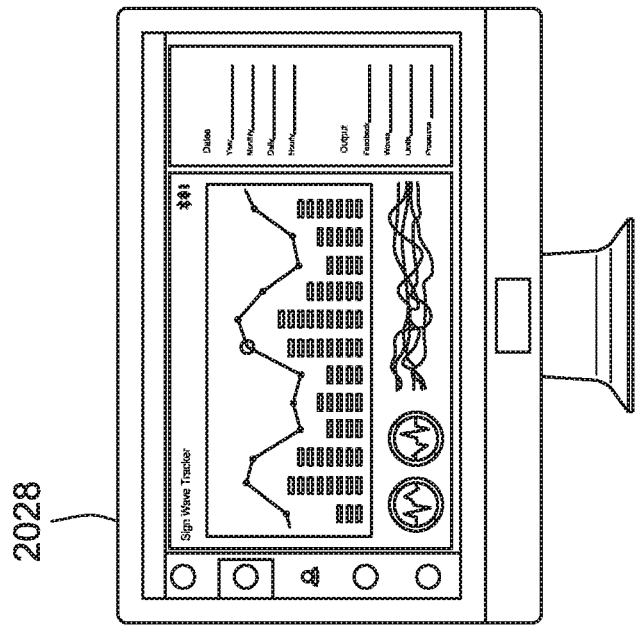
FIG. 52 is a front view of a portal system configured to display results of diagnostic trend information, according to some implementations of the present disclosure.
Figure 54:
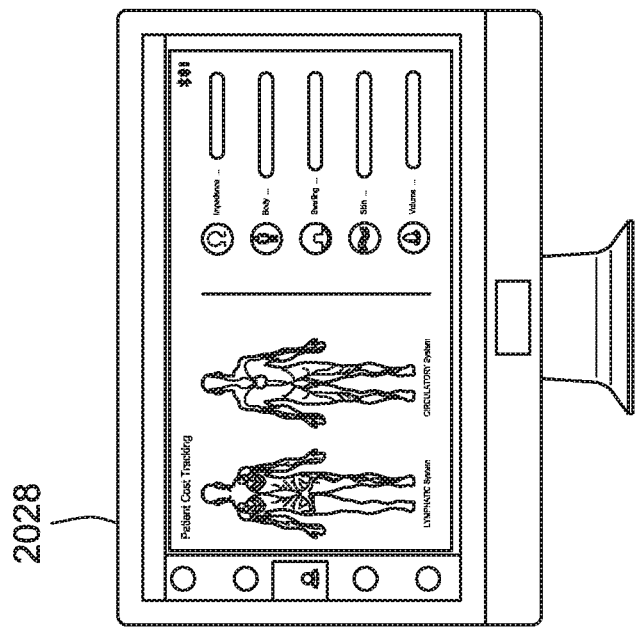
FIG. 54 is a front view of a portal system configured to show user/patient data body metrics, according to some implementations of the present disclosure.
Figure 53:
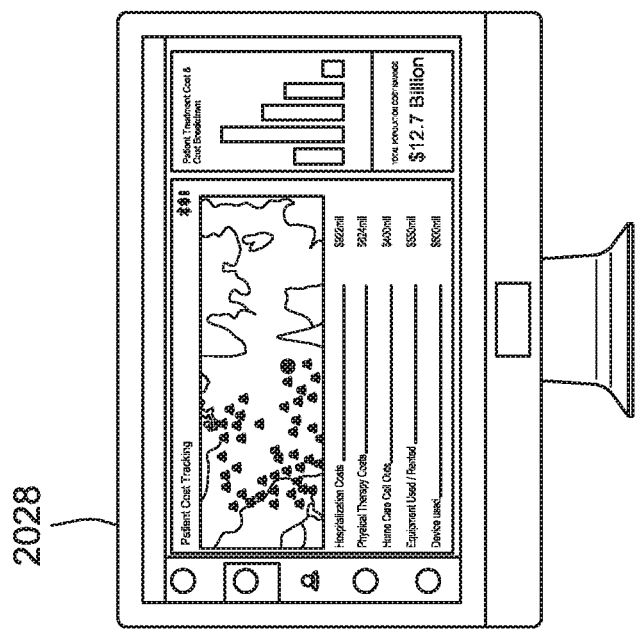
FIG. 53 is a front view of a portal system configured to optionally visually track user/patient incident costs, according to some implementations of the present disclosure.

Referring to FIG. 52, results of a CPG device diagnostic (e.g., waveform processes previously described) can be displayed over time such as to present trend information (e.g., impedance, resistance, etc.) in a graph. For example, wave scans such as on a monthly basis can be presented to the clinician or therapist to provide visual insight into how the therapy is changing the patient's Lymphedema condition. Optionally, as illustrated in FIG. 53, the portal system 2028 can be configured to visually track patient incident cost related to care to monitor health care costs across the managed population to provide an indication of cost savings made relative to hospitalization costs. As illustrated in FIG. 54, the portal system 2028 can present a body composition management graphic interface to show patient data body metrics collected by the system 1000.

The portal system 2028 may also utilise data analytics methods to personalize care plans. The portal could utilise patient history, therapy data and any diagnostic data to automatically recommend and/or adjust treatment plans. An example of this could be to incorporate data coming from an Indocyanine-Green (ICG) scan, which maps out the flow of fluid through the lymphatic networks. This data could provide information on how to personalize the compression waveform for a particular patient, such that applied direction of compression matches the natural flow of the lymphatic system (as seen in the scan). Following the initial setup in this manner, as the portal system 2028 may receive data from a CPG device over time, as well as clinical data entered from the physician, the portal system 2028 could continue to adapt therapy patterns accordingly. This is one example of how the portal system 2028 can personalize care plans for a patient. Apart from therapy, the portal system 2028 can also recommend changes to exercise patterns, diet, and lifestyle.

6.10 High-Resolution Compression Therapy Systems

Compression therapy systems, such as those illustrated in FIGS. 23A and 56A, are capable of emulating manual massage therapy by sequential pressurisation and depressurisation of chambers according to a predetermined pattern.

The resolution of such massage therapies may be further increased by partitioning each chamber (e.g., chambers 1.1, 1.2, 1.3 shown in FIG. 23A) into a plurality of micro-chambers. FIG. 13D illustrates this basic idea, showing a toroidal chamber 13316-C partitioned into four micro-chambers 13304-7 to 13304-10. Micro-chamber 13304-7 is illustrated as directly controlled by an active valve 13400 and the remaining micro-chambers 13304-8 to 13304-10 are pressurised via interconnecting passive valves 13450A-D in a predetermined sequence. In one example of such a sequence, the micro-chamber 13304-7 is pressurised first in the sequence, the micro-chambers 13304-8 and 13304-9 are then pressurised at the same time or about the same time, and the micro-chamber 13304-10 is pressurised last in the sequence.

In some implementations of the present disclosure, the predetermined sequence of pressurization of micro-chambers provides a directional massage that, for example, starts at one end and moves towards another opposing end. For example, the massage starts at a distal end of a user's arm and moves towards a proximal end of the user's arm (or vice versa). For another example, the massage starts at a distal end of a user's leg (near the foot) and moves along a calf muscle and/or shin of the user towards a proximal end of the user's leg near the knee of the user (or vice versa).

Figure 57A:
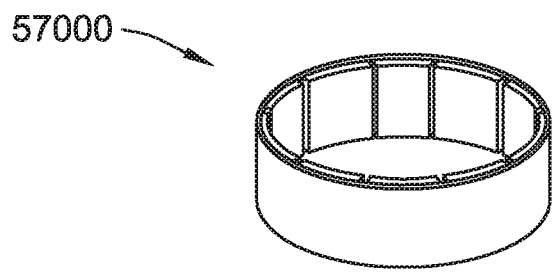
FIG. 57A is an assembled perspective view of a toroidal chamber with micro-chambers, according to some implementations of the present disclosure.
Figure 57B:
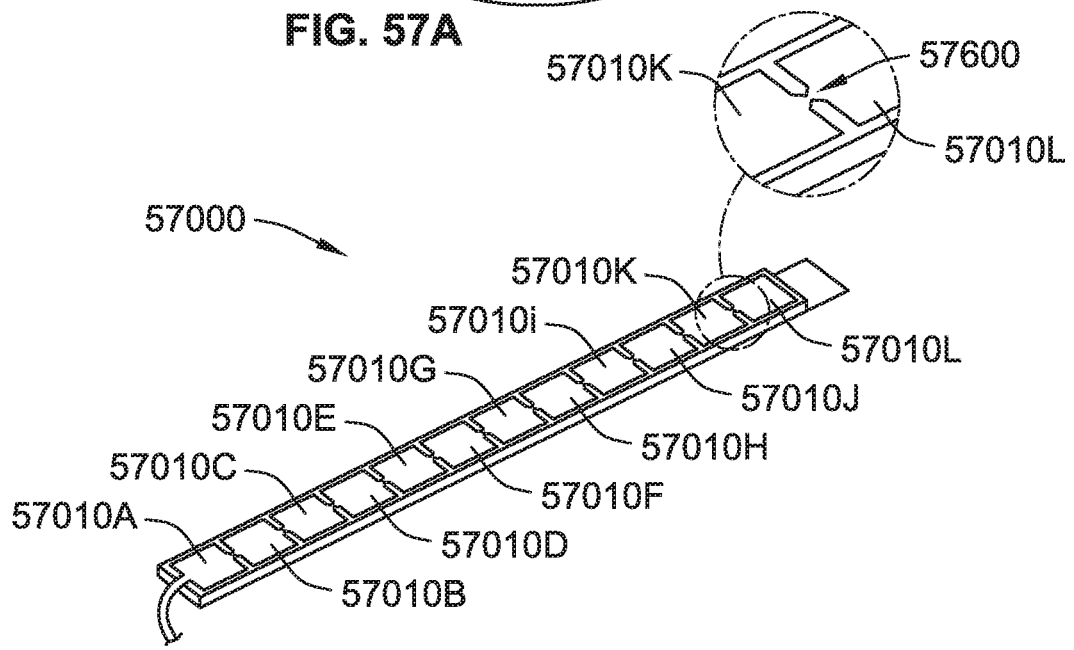
FIG. 57B is a flattened perspective view of the toroidal chamber of FIG. 57A.

Referring to FIGS. 57A and 57B, a toroidal chamber 57000 is partitioned into 12 micro-chambers 57010A-L, in the same or similar fashion as the micro chambers shown in FIG. 13D. The toroidal chamber 57000 is illustrated both in its configuration as worn (FIG. 57A) and in an unrolled or flattened configuration (FIG. 57B) for greater clarity. That is, toroidal refers to the generally toroidal shape of the toroidal chamber 57000 (FIG. 57A) when a garment, including the toroidal chamber 57000, is worn by a user. It is contemplated that a garment can include any number of the toroidal chambers 57000 (e.g., 1, 2, 5, 8, 10, 20, 32, 50, 100, 1000, 10,000, etc. or any number in-between) as a series of rows of the garment where each of the toroidal chambers 57000 is connected to its neighbours along corresponding edges. In some such garments, all of the toroidal chambers 57000 have the same general alignment (e.g., all generally horizontal when the garment is worn, all generally vertical when the garment is worn, etc.). In some other garments, some of the toroidal chambers 57000 have the same, or similar, alignment, and others of the toroidal chambers 57000 have different alignments. The arrangement of the toroidal chambers 57000 in a garment can be selected to provide specific and/or custom compression therapy sessions to a user of the garment. That is, in some implementations, the toroidal chambers 57000 are arranged in a garment to provide efficient massaging of the wearer, thereby resulting in aiding drainage for the user.

According to some implementations, a garment has between about 8 toroidal chambers (e.g., rows) and about 32 toroidal chambers (e.g., rows). In some such implementations, each of the toroidal chambers has about 10 micro-chambers. In some implementations, a garment according to the present disclosure includes between about 50 micro-chambers and about 100 micro-chambers. In some implementations, a garment includes about 80 micro-chambers. Various other garments with various other amounts of toroidal chambers/rows and various other amounts of micro-chambers are contemplated to provide therapy and/or massage.

According to some implementations of the present disclosure, a chamber or macro-chamber is a chamber that is controlled with an active valve. In some such implementations, the macro-chamber is partitioned into smaller sub-chambers or micro-chambers, where each of the micro-chambers is connected with at least one other micro-chamber via passive valves and/or conduits.

In some implementations, a macro-chamber of the present disclosure has a length/height between about 20 millimeters and about 120 millimeters, a width between about 10 millimeters and about 80 millimeters, and a depth/thickness between about 1 millimeter and about 10 millimeters.

In some implementations, a micro-chamber of the present disclosure has a length/height between about between about 0.25 inches (6 millimeters) and about two inches (50 millimeters), a width between about 0.25 inches (6 millimeters) and about two inches (50 millimeters), and a depth/thickness between about 0.01 inches (0.25 millimeters) and about 0.5 inches (12.5 millimeters). In some implementations, a micro-chamber has a length of about 12.5 millimeters, a width of about 12.5 millimeters, and a depth/thickness of about 5 millimeters.

In FIGS. 57A and 57B, the micro-chambers 57010A-L are connected in sequence around the toroid via narrow-gauge "micro-conduits" 57600 that act as passive valves. Pressurising the first micro-chamber 57010A causes each subsequent micro-chamber 57010B-L to be pressurised in a progressive sequence around the toroidal chamber 57000. In some implementations, each of the micro-conduits 57600 has a minimum diameter, which is between about 0.001 inches (25 microns) and about 0.25 inches (6 millimeters). In some implementations, the minimum diameter of each of the micro-conduits 57600 is about 5 millimeters.

According to some implementations, each toroidal chamber/row of a garment is separately pressurized via a separate and distinct active valve. Alternatively, one or more of the toroidal chambers/rows of a garment are fluidly connected to one or more other toroidal chambers/rows of the garment via one or more conduits. In some such implementations, the conduits connecting one toroidal chamber (e.g., macro-chamber) to another has a diameter of about 5 millimeters.

A compression therapy utilising a partitioned chamber such as the toroidal chamber 57000 is thus able to create a micro-massage on the wearer's skin. One aim of a micro-massage is to emulate the stretching effect of natural bodily movement. Lymphedema patients often lack normal mobility and thus their skin is deprived of this natural stretching effect. In addition, the micro-massage can increase pre-load of the lymphatic capillaries and greatly improve lymphatic and venous micro-circulation.

Figure 58:
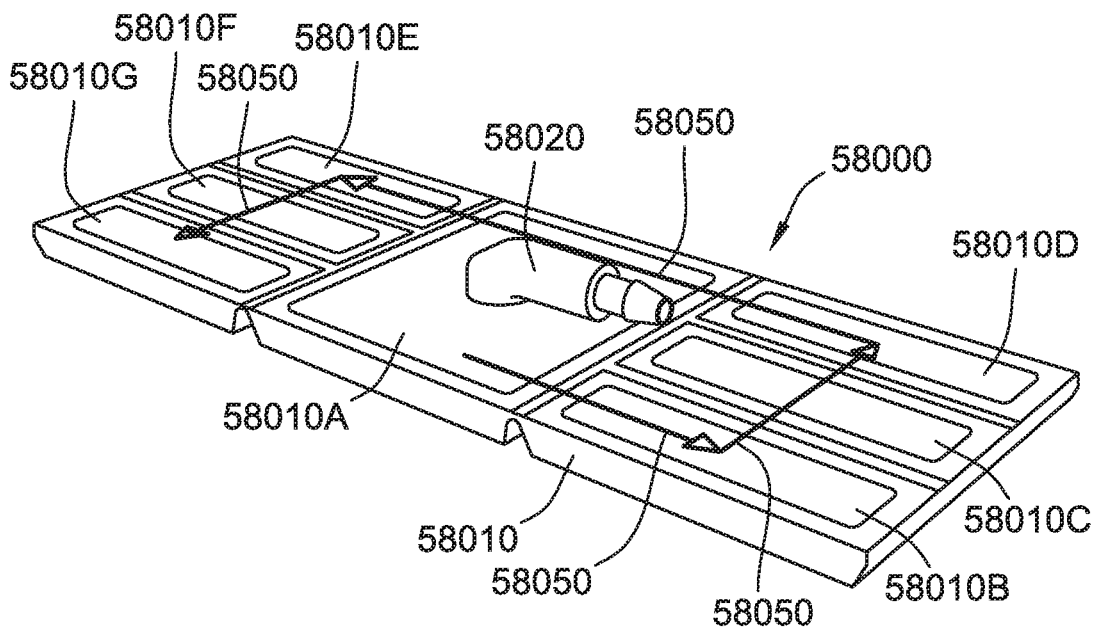
FIG. 58 is a flattened perspective view of a toroidal chamber with micro-chambers, according to some implementations of the present disclosure.

Referring to FIG. 58, a toroidal chamber 58000 includes multiple micro-chambers 58010A-G. Toroidal chamber 58000 is illustrated in a flattened configuration for greater clarity. Toroidal chamber 58000 is partitioned in two dimensions into a matrix pattern of the micro-chambers 58010A-G. Such a partitioning enables a two-dimensional aspect to be introduced to the micro-massage, in that the micro-massage can proceed along, for example, a vertical and/or a horizontal axis depending on the sequence of interconnection of the micro-chambers 58010A-G. The toroidal chamber 58000 also includes a pneumatic coupling 58020, that is fluidly connected with a first one of the micro-chambers 58010A to deliver pressurized gas (e.g., air), which leads to pressurisation of the other micro-chambers 58010B-G based on the sequence of interconnection of the micro-chambers 58010A-G.

Figure 59:
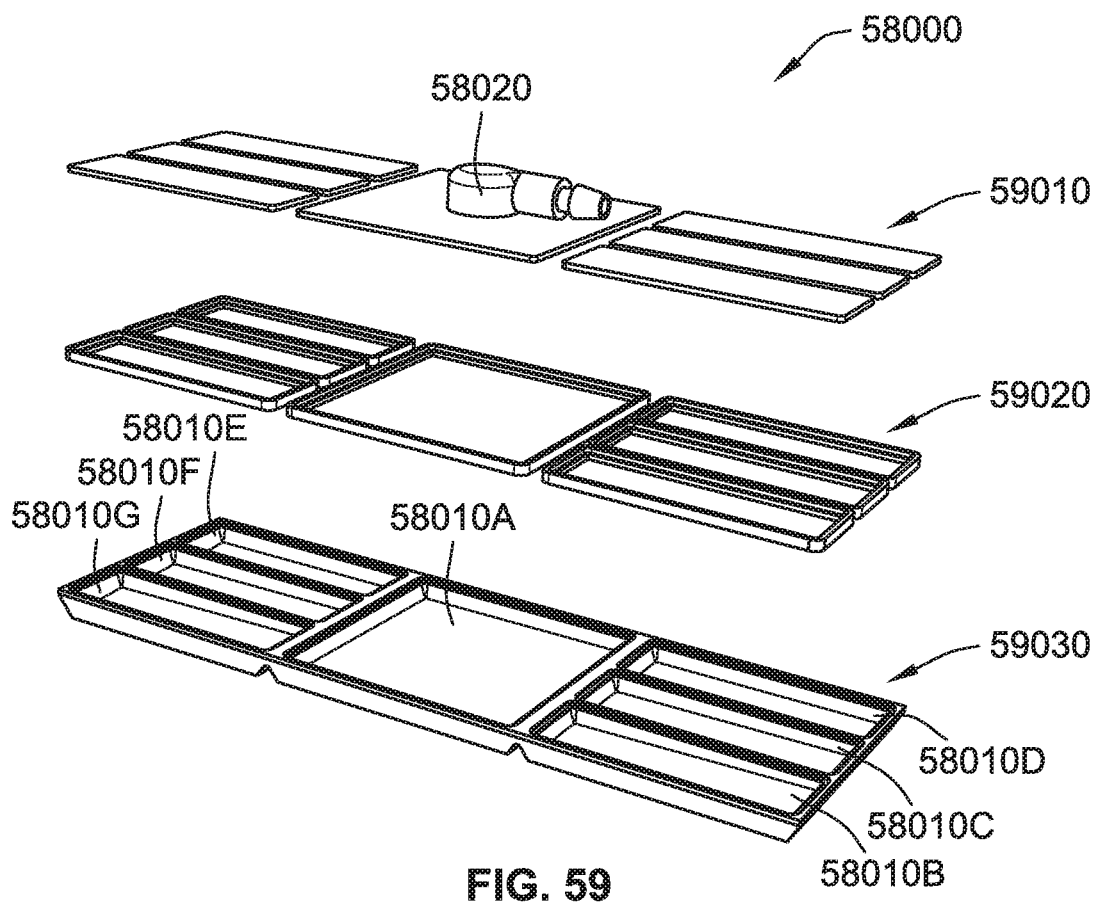
FIG. 59 is an exploded perspective view of the toroidal chamber of FIG. 58.
Figure 60:
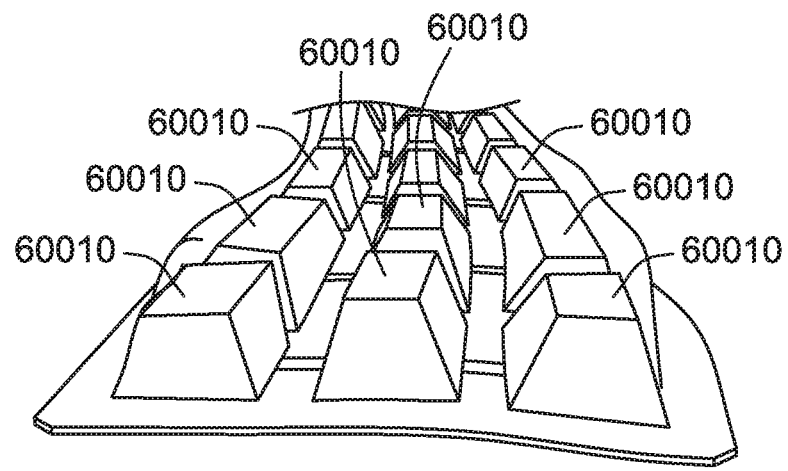
FIG. 60 is a perspective view of thermoformed micro-chambers of a chamber.

Referring to FIG. 59, an exploded view of the toroidal chamber 58000 is shown, which illustrates how the toroidal chamber 58000 is made up of three layers 59010, 59020, and 59030. The backing (outer surface) 59010 may be made from a rigid material. The micro-chambers 58010A-G are formed by an inner layer 59030 that may be moulded or formed from an elastic material (e.g. silicone, TPE, airtight textile). This allows for compressive forces to be directed inwards towards the surface of the skin. The micro-chambers 58010A-G can be moulded or formed into the final air-filled shape, allowing for a lightweight set of micro-chambers 58010A-G that are designed to be form-fitting and provide uniform compression. Moulding the inner layer 59030 from a tacky or sticky substance such as silicone increases the stretching effect of the micro-massage provided by the toroidal chamber 58000. The choice of materials and manufacturing process used to form the inner layer 59030 can introduce a third or depth dimension to the micro-massage. One example of this could be to thermoform the micro-chambers 58010A-G to create different directions during inflation. An example of this is illustrated in FIG. 60, where the micro-chambers 60010 are thermoformed to inflate in a generally trapezoidal manner, as indicated by the generally trapezoidal shape. In FIG. 60, the micro-chambers 60010 are approximately 12.5 mm square. Various other dimensions for the micro-chambers 60010 are contemplated, such as, for example, approximately 5 mm square, approximately 7 mm square, approximately 10 mm square, approximately 20 mm square, approximately 25 mm square, etc., or any combination thereof (e.g., portions of the micro-chambers 60010 can have the same or different dimensions).

Another method for producing a third dimension of a micro-massage can involve having different knitting patterns in the textile to dictate the properties of the direction in which the material inflates and thereby have a three-dimensional effect. The third dimension may also be implemented via differing rates of inflation of the micro-chambers of a chamber, which in turn may be implemented via micro-conduits of different resistances to flow (e.g. different minimum diameters of the micro-conduits).

Referring back to FIG. 59, the middle layer 59020 of the toroidal chamber 58000 forms a seal for each of the micro-chambers 58010A-G. In some implementations, the middle layer 59020 contains micro-conduits that fluidly interconnect the micro-chambers 58010A-G. The configuration of the micro-conduits in the middle layer 59020 controls the sequence in which the micro-chambers 58010A-G are pressurised after the pressurisation of the first micro-chamber 58010A. In one example, the arrows 58050 shown in FIG. 58 illustrate a predetermined pressurisation sequence (e.g., counterclockwise) of the micro-chambers 58010A-G. Each of the arrows 58050 corresponds to a micro-conduit between the adjacent pair of micro-chambers interconnected by the arrow 58050. The diameter of each micro-conduit can be selected/formed to control a rate of inflation of the corresponding micro-chamber(s). Appropriate configuration of the micro-conduits in the middle layer 59020 therefore can lend a third dimension to the micro-massage implemented by the pressurisation of the toroidal chamber 58000.

The configuration of the micro-conduits, and therefore the character of the resulting micro-massage, may be personalized for a particular patient. As described above, an ICG scan of the affected areas of a user/patient could provide information on how to personalize the micro-massage for a particular user/patient, such that the direction of the micro-massage matches the natural flow of the lymphatic system (as determined from the scan). Alternatively, as mentioned above, information enabling personalization may be obtained from the patient's clinical history, e.g. the pattern of swelling.

Micro-chambers may also be partitioned from non-toroidal chambers which do not necessarily wrap around a limb. Such chambers could be localised chambers taking any shape, used to target specific areas of the body. One example is an anatomically-shaped chamber such as the bicep zone 19410 in FIG. 19.

In some implementations, micro-chambers may be coated and/or have a surface finish applied to at least a portion thereof, so as to produce a textured surface to enhance skin stretching, improve comfort, and regulate skin environment. Silicone dot protrusions (e.g., generally circular dot protrusions) may present one particularly suitable option given silicone's natural high-friction surface properties. Alternatively, the micro-chamber surface may be brushed to create the same, or similar, effect.

6.10.1 Cyclic Pressurisation

A more intricate control system for the micro-chambers may involve
 a. Pre-inflating the micro-chambers to a pre-set therapy pressure.
 b. Cycling the micro-chambers repeatedly between a (higher) target therapy pressure and (lower) pre-set therapy pressure.
 c. (Optionally) Altering the target therapy pressure and/or the duty cycle of the cyclic pressurisation (possibly in response to sensor data).

Cyclic pressurisation is similar to the oscillatory pressurisation waveforms described above in relation to FIG. 56A. Micro-chambers are particularly suitable for cyclic pressurisation because their small volume allows high frequency cycling (e.g. up to 10 Hz) between substantially different pressures without overloading the CPG device 1002. Cyclic pressurisation emulates manual massage so as to break up gel-like tissue that forms at a more advanced stage of lymphedema.

7. GLOSSARY

For the purposes of the present disclosure, in certain forms of the present technology, one or more of the following definitions may apply. In other forms of the present disclosure, alternative definitions may apply.

7.1 Aspects of CPG Devices

Blower or flow generator: a device that produces a flow of air at a pressure above ambient pressure. Such a device may be reversed (e.g., by reversing a motor direction) to draw (vacuum) a flow of air at a negative pressure below ambient pressure.

Controller: a device or portion of a device that adjusts an output based on an input. For example, one form of controller has a variable that is under control—the control variable—that constitutes the input to the device. The output of the device is a function of the current value of the control variable, and a set point for the variable. A CPG device (e.g., CPG device 1002) may include a controller that has pressure as an input, a target pressure as the set point, a level of pressure as an output, or any combination thereof. Another form of input may be a flow rate from a flow sensor. The set point of the controller may be one or more of fixed, variable or learned. A pressure controller may be configured to control a blower or pump to deliver air at a particular pressure. A valve controller may be configured to open or close one or more valves selectively according to a programmed protocol such as in response to a measure such as time and/or any of the signals provided by one or more sensors. A controller may include or be one or more microcontrollers, one or more microprocessors, one or more processors, or any combination thereof.

Therapy: therapy in the present context may be one or more of compression therapy, such as static compression therapy, sequential compression therapy, including massage therapy, as well as the therapies described in more detail herein, or any combination thereof.

Motor: a device for converting electrical energy into rotary movement of a member. In the present context the rotating member can include an impeller, which rotates in place around a fixed axis so as to impart a pressure increase or decrease to air moving along the axis of rotation.

Transducers: a device for converting one form of energy or signal into another. A transducer may be a sensor or detector for converting mechanical energy (such as movement) into an electrical signal. Examples of transducers include pressure sensors, flow sensors, and temperature sensors.

Volute: the casing of the centrifugal pump that directs the air being pumped by the impeller, such as slowing down the flow rate of air and increasing the pressure. The cross-section of the volute increases in area towards the discharge port.

7.2 CPG Device Parameters

Flow rate: the instantaneous volume (or mass) of air delivered or drawn per unit time. In some cases, a reference to flow rate will be a reference to a scalar quantity, namely a quantity having magnitude only. In other cases, a reference to flow rate will be a reference to a vector quantity, namely a quantity having both magnitude and direction (e.g., out of the CPG device or into the CPG device). Flow rate is given the symbol Q.

Pressure: force per unit area. Pressure may be measured in a range of units, including $cmH_2O$, $g-f/cm^2$, and hectopascals. One (1) $cmH_2O$ is equal to 1 $g-f/cm^2$ and is approximately 0.98 hectopascal. In this specification, unless otherwise stated, pressure is given in units of $cmH_2O$.

8. OTHER REMARKS

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

What is claimed is:

1. A garment for providing circulatory system disorder therapy, the garment comprising:
   a skin contacting layer with a plurality of recessed portions;
   a backing layer coupled to the skin contacting layer such that the skin contacting layer and the backing layer form a plurality of toroidal chambers, a first one of the plurality of toroidal chambers being partitioned into a plurality of micro-chambers formed by the plurality of recessed portions of the skin contacting layer, each of the plurality of micro-chambers being in direct fluid communication with at least one other of the plurality of micro-chambers;
   a middle layer in cooperation with the plurality of recessed portions and extending between the skin contacting layer and the backing layer to form side walls for each of the plurality of micro-chambers and to form a plurality of micro-conduits acting as passive valves between the plurality of micro-chambers, the middle layer being a different layer from the skin contacting layer and the backing layer; and
   a coupling coupled to the backing layer and being configured to supply pressurized air directly into the first toroidal chamber such that the pressurized air is delivered to a first one of the plurality of micro-chambers of the first toroidal chamber.

2. The garment of claim 1, wherein each of the plurality of toroidal chambers has a length, a width, and a depth, the length being between about 20 millimeters and about 120 millimeters, the width being between about 10 millimeters and about 80 millimeters, the depth being between about 1 millimeter and about 10 millimeters.

3. The garment of claim 1, wherein each of the plurality of micro-chambers has a micro-length, a micro-width, and a micro-depth, the micro-length being between about 6 millimeters and about 50 millimeters, the width being between about 6 millimeters and about 50 millimeters, the micro-depth being between about 0.25 millimeters and about 12.5 millimeters.

4. The garment of claim 3, wherein the micro-length, the micro-width, and the micro-depth are selected to aid in providing a massage to a user of the garment.

5. The garment of claim 1, wherein each of the plurality of micro-chambers is in direct fluid communication with at least one other of the plurality of micro-chambers via the plurality of micro-conduits, each of the plurality of micro-conduits having a minimum diameter, the minimum diameter being between about 25 microns and about 6 millimeters, wherein the minimum diameter is selected to aid in providing a massage to a user of the garment.

6. The garment of claim 1, wherein each of the plurality of toroidal chambers forms a row of the garment when the garment is worn by a user.

7. The garment of claim 1, wherein the coupling is configured to supply the pressurized air directly into the first toroidal chamber such that the plurality of micro-chambers are pressurized in a predetermined sequence.

8. The garment of claim 7, wherein the predetermined sequence follows a generally circular path about a limb of a user of the garment.

9. The garment of claim 7, wherein the pressurization of the plurality of micro-chambers in the predetermined sequence provides a massage to a user wearing the garment on a body part of the user.

10. The garment of claim 7, further comprising a controller that is configured to cycle the pressurization of the plurality of micro-chambers between at least two different pressure levels to provide a massage to a user wearing the garment on a body part of the user.

11. The garment of claim 1, wherein a first one of the plurality of micro-conduits has a first minimum diameter and a second one of the plurality of micro-conduits has a second minimum diameter that is different from the first minimum diameter such that the pressurized air moves through the first micro-conduit and the second micro-conduit at different rates.

12. The garment of claim 1, wherein the skin contacting layer includes an elastic material and the backing layer includes a rigid material.

13. The garment of claim 7, wherein the skin contacting layer includes a first material having a first Young's modulus and the backing layer includes a second material having a second Young's modulus that is different from the first Young's modulus.

14. The garment of claim 13, wherein the second Young's modulus is greater than the first Young's modulus.

15. The garment of claim 13, wherein the second Young's modulus is between two and ten times greater than the first Young's modulus.

16. The garment of claim 1, wherein the skin contacting layer is continuous.

17. The garment of claim 16, wherein the plurality of toroidal chambers are fluidly independent.

18. A garment for providing circulatory system disorder therapy, the garment comprising:
   a skin contacting layer with a plurality of recessed portions;
   a backing layer coupled to the skin contacting layer such that the skin contacting layer and the backing layer form a plurality of macro-chambers, a first one of the plurality of macro-chambers being partitioned into a plurality of micro-chambers formed by the plurality of recessed portions of the skin contacting layer, each of the plurality of micro-chambers being in direct fluid communication with at least one other of the plurality of micro-chambers; and
   a coupling coupled to the backing layer and being configured to supply pressurized air directly into the first macro-chamber such that the pressurized air is delivered to a first one of the plurality of micro-chambers of the first macro-chamber;

a middle layer in cooperation with the plurality of recessed portions and extending between the skin contacting layer and the backing layer to form side walls for each of the plurality of micro-chambers, the middle layer being a different layer from the skin contacting layer and the backing layer;

wherein the middle layer forms a plurality of micro-conduits acting as passive valves between the plurality of micro-chambers of the first macro-chamber such that pressurized air in the first micro-chamber is able to move via a first one of the plurality of micro-conduits into at least one other one of the plurality of micro-chambers.

19. The garment of claim 18, wherein the first micro-conduit has a first minimum diameter and a second one of the plurality of micro-conduits has a second minimum diameter that is different from the first minimum diameter such that the pressurized air moves through the first micro-conduit and the second micro-conduit at different flow rates.

20. The garment of claim 18, wherein at least a portion of the plurality of micro-chambers has a generally trapezoidal profile shape when pressurized.

21. The garment of claim 18, wherein the coupling is configured to supply the pressurized air directly into the first macro-chamber such that the plurality of micro-chambers are pressurized in a predetermined sequence.

22. The garment of claim 18, further comprising a controller that is configured to cycle the pressurization of the plurality of micro-chambers between at least two different pressure levels to provide a massage to a user wearing the garment on a body part of the user.

23. The garment of claim 18, wherein the skin contacting layer includes a first material having a first Young's modulus and the hacking layer includes a second material having a second Young's modulus between two and ten times greater than the first Young's modulus.

24. The garment of claim 18, wherein the skin contacting layer is continuous.

25. The garment of claim 24, wherein the plurality of macro-chambers are fluidly independent.

* * * * *